US009315566B2

(12) United States Patent
Macary et al.

(10) Patent No.: US 9,315,566 B2
(45) Date of Patent: Apr. 19, 2016

(54) PATHOGENIC MYCOBACTERIA-DERIVED MANNOSE-CAPPED LIPOARABINOMANNAN ANTIGEN BINDING PROTEINS

(75) Inventors: Paul Anthony Macary, Singapore (SG); Conrad En Zuo Chan, Singapore (SG); Brendon John Hanson, Singapore (SG); Markus R. Wenk, Singapore (SG)

(73) Assignees: National University of Singapore, Singapore (SG); DSO National Laboratories, Singapore (SG)

( * ) Notice: Subject to any disclaimer, the term of this patent is extended or adjusted under 35 U.S.C. 154(b) by 0 days.

(21) Appl. No.: 13/981,442

(22) PCT Filed: Jan. 25, 2012

(86) PCT No.: PCT/SG2012/000022
§ 371 (c)(1),
(2), (4) Date: Jul. 24, 2013

(87) PCT Pub. No.: WO2012/102679
PCT Pub. Date: Aug. 2, 2012

(65) Prior Publication Data
US 2013/0309237 A1 Nov. 21, 2013

Related U.S. Application Data

(60) Provisional application No. 61/435,396, filed on Jan. 24, 2011.

(51) Int. Cl.
C07K 16/12 (2006.01)
C07K 16/00 (2006.01)
C12Q 1/00 (2006.01)
A61K 39/395 (2006.01)
G01N 33/569 (2006.01)

(52) U.S. Cl.
CPC ........ *C07K 16/1289* (2013.01); *G01N 33/5695* (2013.01); *C07K 2317/21* (2013.01); *C07K 2317/24* (2013.01); *C07K 2317/33* (2013.01); *C07K 2317/52* (2013.01); *C07K 2317/522* (2013.01); *C07K 2317/55* (2013.01); *C07K 2317/92* (2013.01); *G01N 2400/00* (2013.01)

(58) Field of Classification Search
CPC ... A61K 6/00; A61K 2039/505; A61K 39/04; A61K 39/395; A61K 35/74; A61K 39/40; A61K 39/02; G01N 33/5695; G01N 2333/35; G01N 2469/20; G01N 33/56911
USPC .......... 424/137.1, 184.1, 130.1, 248.1, 139.1, 424/164.1, 190.1; 435/7.1, 7.32, 4, 70.21; 530/388.1, 387.9, 300
See application file for complete search history.

(56) References Cited

U.S. PATENT DOCUMENTS

| 6,168,790 | B1 | 1/2001 | Ulevitch et al. |
| 6,245,331 | B1 | 6/2001 | Laal et al. |
| 6,458,367 | B1 | 10/2002 | Verschoor et al. |
| 6,599,691 | B1 | 7/2003 | Ralls et al. |
| 6,733,983 | B1 | 5/2004 | Houthoff et al. |
| 6,841,159 | B2 | 1/2005 | Simonson |
| 7,615,222 | B2 | 11/2009 | Koulchin et al. |
| 2002/0034763 | A1 | 3/2002 | Glatman-Freedman et al. |
| 2005/0281828 | A1 | 12/2005 | Bowdish et al. |
| 2007/0154979 | A1 | 7/2007 | Tanaka et al. |
| 2007/0292447 | A1 | 12/2007 | Bercovier et al. |
| 2008/0015344 | A1 | 1/2008 | Fraser-Reid et al. |
| 2008/0025913 | A1 | 1/2008 | Bowdish et al. |
| 2009/0017061 | A1 | 1/2009 | Appelmelk et al. |
| 2009/0117661 | A1 | 5/2009 | Tanaka et al. |
| 2010/0075441 | A1 | 3/2010 | Badwan et al. |

FOREIGN PATENT DOCUMENTS

| CN | 101382548 A | 3/2009 |
| CN | 101429238 A | 5/2009 |
| WO | WO 92/14155 A1 | 8/1992 |
| WO | WO 97/34149 A1 | 9/1997 |
| WO | WO 98/31387 A1 | 7/1998 |
| WO | WO 2005/010151 A2 | 2/2005 |
| WO | WO 2005010151 A2 * | 2/2005 |
| WO | 2006078164 A2 | 7/2006 |
| WO | WO 2007/047189 A2 | 4/2007 |
| WO | WO 2009/094551 A1 | 7/2009 |

OTHER PUBLICATIONS

Driessen et al. 2009 (Role of phosphatidylinositol mannosides in the interaction between mycobacteria and DC-SIGN; Infection and Immunity 77(10):4538-4547).*
Driessen et al. 2009 (Role of Phosphatidylinositol Mannosides in the Interaction between Mycobacteria and DC-SIGN; Infection and Immunity; 77(10): 4538-4547).*
Greenspan et al. 1999 (Defining epitopes: It's not as easy as it seems; Nature Biotechnology, 17:936-937).*

(Continued)

*Primary Examiner* — Gary Nickol
*Assistant Examiner* — Mary Lyons
(74) *Attorney, Agent, or Firm* — Kilpatrick Townsend & Stockton LLP

(57) ABSTRACT

Described herein are antigen binding proteins that bind to pathogenic mycobacteria-derived Mannose-Capped Lipoarabinomannan (ManLAM) and methods and kits for using and making the antigen binding proteins. Also described herein are antigen binding proteins that bind to the alpha 1-2 linkage mannose caps of ManLAM, antigen binding proteins that bind to a mannose cap with up to three alpha 1-2 linked mannose residues, and antigen binding proteins that bind to LAM with a mannose sugar capping motif.

13 Claims, 9 Drawing Sheets

(56) References Cited

OTHER PUBLICATIONS

Adams, E.W. et al., "Oligosaccharide and Glycoprotein Microarrays as Tools in HIV Glycobiology: Glycan-Dependent gp120/Protein Interactions," *Chemistry & Biology*, Jun. 2004, pp. 875-881, vol. 11.
Appelmelk, B.J. et al., "The mannose cap of mycobacterial lipoarabinomannan does not dominate the *Mycobacterium*-host interaction," *Cellular Microbiology*, 2008, pp. 930-944, vol. 10, No. 4.
Araj, G.F. et al., "Improved Detection of Mycobacterial Antigens in Clinical Specimens by Combined Enzyme-Linked Immunosorbent Assays," *Diagn, Microbiol. Infect. Dis.*, 1993, pp. 19-27, vol. 17, No. 2.
Baba, K. et al., "Rapid and specific diagnosis of Tuberculous Pleuritis With Immunohistochemistry by Detecting *Mycobacterium Tuberculosis* Complex Specific Antigen MPT64 in Patients From a HIV Endemic Area," *Applied Immunohistochem Molecular Morphology*, Dec. 2008, pp. 554-561, vol. 16, No. 6.
Ben-Selma, W. et al., "Rapid detection of Mycobacterium tuberculosis in sputum by Patho-TB kit in comparison with direct microscopy and culture," *Diagnostic Microbiology and Infectious Disease*, 2009, pp. 232-235, vol. 65, No. 3.
Boehme, C. et al., "Detection of *mycobacterial lipoarabinomannan* with an antigencapture ELISA in unprocessed urine of Tanzanian patients with suspected tuberculosis," *Transactions of the Royal Society of Tropical Medicine and Hygiene*, 2005, pp. 893-900, vol. 99, No. 12.
Bothamley, G.H., "Epitope-Specific Antibody Levels Demonstrate Recognition of New Epitopes and Changes in Titer but Not Affinity during Treatment of Tuberculosis," *Clinical and Diagnostic Laboratory Immunology*, Sep. 2004, pp. 942-951, vol. 11, No. 5.
Bua, A. et al., "Phages specific for *mycobacterial lipoarabinomannan* help serodiagnosis of tuberculosis," *New Microbiologica*, 2009, pp. 293-296, vol. 32.
Chakraborty, N. et al., "A rapid immunochromatographic assay for the detection of *Mycobacterium tuberculosis* antigens in pulmonary samples from HIV seropositive patients and its comparison with conventional methods," *Journal of Microbiological Methods*, 2009, pp. 12-17, vol. 76, No. 1.
Chan, E.D. et al., "Diagnosis of Tuberculosis by a Visually Detectable Immunoassay for Lipoarabinomannan," *American Journal of Respiratory and Critical Care Medicine*, 2000, pp. 1713-1719, vol. 161, No. 5.
Chatterjee, D. et al., "Lipoarabinomannan of *Mycobacterium tuberculosis*," *The Journal of Biological Chemistry*, 1992, pp. 6234-6239, vol. 267, No. 9.
Chatterjee, D., "The mycobacterial cell wall: structure, biosynthesis and sites of drug action," *Current Opininion in Chemical Biology*, 1997, pp. 579-588, vol. 1, No. 4.
Cho, S.N. et al., "Production of Monoclonal Antibodies to Lipoarabinomannan-B and Use in the Detection of Mycobacterial Antigens in Sputum," *Yonsei Medical Journal*, 1990, pp. 333-338, vol. 31, No. 4.
De Haard, H.J.W., "Construction of Large Naïve Fab Libraries," *Methods in Molecular Biology*, 2001, pp. 87-100, vol. 178.
Dheda, K. et al., "Clinical Utility of a Commercial LAM-ELISA Assay for TB Diagnosis in HIV-Infected Patients Using Urine and Sputum Samples," *PLoS One*, 2010, p. e9848, vol. 5, No. 3.
Elliott, A.M. et al., "Negative sputum smear results in HIV-positive patients with pulmonary tuberculosis in Lusaka, Zambia," *Tubercle Lung Disease*, 1993, pp. 191-194, vol. 74, No. 3.
Fujiwara, N. et al., "Production and partial characterization of anti-cord factor (trehalose-6, 6'-dimycolate) IgG antibody in rabbits recognizing mycolic acid subclasses of *Mycobacterium tuberculosis* or *Mycobacterium avium*," *FEMS Immunology Medical Microbiology*, 1999, pp. 141-149, vol. 24, No. 2.
Geijtenbeek, T.B. et al., "Mycobacteria Target DC-SIGN to Suppress Dendritic Cell Function," *The Journal Experimental Medicine*, 2003, pp. 7-17, vol. 197, No. 1.

Gevorkian, G. et al., "Peptide mimotope of *Mycobacterium tuberculosis* carbohydrate immunodeterminants," *Biochemical Journal*, 2005, pp. 411-417, vol. 387.
Glatman-Freedman, A., "The role of antibody-mediated immunity in defense against *Mycobacterium tuberculosis*: Advances toward a novel vaccine strategy," *Tuberculosis*, 2006, pp. 191-197, vol. 86, Nos. 3-4.
Hamasur, B. et al., "A mycobacterial lipoarabinomannan specific monoclonal antibody and its F(ab') fragment prolong survival of mice infected with *Mycobacterium tuberculosis*," *Clinical and Experimental Immunology*, 2004, pp. 30-38, vol. 138, No. 1.
Hamasur, B. et al., "*Mycobacterium tuberculosis* arabinomannan-protein conjugates protect against tuberculosis," *Vaccine*, 2003, pp. 4081-4093, vol. 21, Nos. 25-26.
Hamasur, B. et al., "Rapid diagnosis of tuberculosis by detection of mycobacterial lipoarabinomannan in urine," *Journal of Microbiological Methods*, 2001, pp. 41-52, vol. 45, No. 1.
Hölemann, A. et al., "Synthesis of a Core Arabinomannan Oligosaccharide of *Mycobacterium tuberculosis*," *Journal of Organic Chemistry*, 2006, pp. 8071-8088, vol. 71.
Hoogenboom, H.R., "Selecting and screening recombinant antibody libraries," *Nature Biotechnology*, 2005, pp. 1105-1116, vol. 23, No. 9.
Kambashi, B. et al., "Utility of nucleic acid amplification techniques for the diagnosis of pulmonary tuberculosis in sub-Saharan Africa," *Int J Tuberc Lung Dis*, 2001, pp. 364-369, vol. 5, No. 4.
Kang, P.B. et al., "The human macrophage mannose receptor directs *Mycobacterium tuberculosis* lipoarabinomannan-mediated phagosome biogenesis," *Journal of Experimental Medicine* 2005, pp. 987-999, vol. 202, No. 7.
Lawn, S.D. et al., "Urine lipoarabinomannan assay for tuberculosis screening before antiretroviral therapy diagnostic yield and association with immune reconstitution disease," *AIDS*, 2009, pp. 1875-1880, vol. 23, No. 14.
Malik, Z.A. et al., "Cutting edge: *Mycobacterium tuberculosis* Blocks $Ca^{2+}$ Signaling and Phagosome Maturation in Human Macrophages via Specific Inhibition of Sphingosine Kinase," *Journal of Immunology*, 2003, pp. 2811-2815, vol. 170, No. 6.
Mason, P.R. et al., "The use of monoclonal antibodies to identify mycobacteria grown in culture in Zimbabwe," *Tubercle and Lung Disease*, 1993, pp. 195-199, vol. 74, No. 3.
Mehta, P.K. et al., "Protective immunity to experimental tuberculosis by mannophosphoinositides of mycobacteria," *Med Microbiol Immunol*, 1988, pp. 265-284, vol. 177, No. 5.
Murase, T. et al., "Structural insights into antibody recognition of mycobacterial polysaccharides," *Journal of Molecular Biology*, 2009, pp. 381-392, vol. 392, No. 2.
Nigou, J. et al., "Lipoarabinomannans: from structure to biosynthesis," *Biochimie*, 2003, pp. 153-166, vol. 85, Nos. 1-2.
Pai, M. et al., "Nucleic acid amplification tests in the diagnosis of tuberculous pleuritis: a systematic review and meta-analysis," *BMC Infectious Disease*, 2004, p. 6, vol. 4.
Pai, M. et al., "Systematic review: T-cell-based assays for the diagnosis of latent tuberculosis infection: an update," *Annals of Internal Medicine*, 2008, pp. 177-184, vol. 149, No. 3.
Pathak, S.K. et al., "*Mycobacterium tuberculosis* lipoarabinomannan-mediated IRAK-M induction negatively regulates Toll-like receptor-dependent interleukin-12 p40 production in macrophages," *Journal of Biological Chemistry*, 2005, pp. 42794-42800, vol. 280, No. 52.
Patil, S.A. et al., "Lipoarabinomannan antigen and anti-lipoarabinomannan antibody profile in the serum of patients with mycobacterial infections and their significance in disease process," *Serodiagnosis and Immunotherapy in Infectious Disease*, 1995, pp. 59-63, vol. 7, No. 2.
Patil, S.A., "Enhanced antibody activity in serum depleted of antigen," *Journal of Immunoassay and Immunochemistry*, 2001, pp. 407-411, vol. 22, No. 4.
PCT International Search Report and Written Opinion, PCT Application No. PCT/SG2012/000022, Dec. 13, 2012, twelve pages.

(56) References Cited

OTHER PUBLICATIONS

Pereira Arias-Bouda, L.M. et al., "Development of Antigen Detection Assay for Diagnosis of Tuberculosis Using Sputum Samples," *Journal of Clinical Microbiology*, Jun. 2000, pp. 2278-2283, vol. 38, No. 6.

Purohit, M.R. et al., "Immunohistochemical diagnosis of abdominal and lymph node tuberculosis by detecting *Mycobacterium tuberculosis* complex specific antigen MPT64," *Diagnostic Pathology*, 2007, vol. 2, nine pages.

Ratner, D.M. et al., "A Linear Synthesis of Branched High-Mannose Oligosaccharides from the HIV-1 Viral Surface Envelope Glycoprotein gp120," *European Journal of Organic Chemistry*, 2002, pp. 826-833.

Reither, K. et al., "Low sensitivity of a urine LAM-ELISA in the diagnosis of pulmonary tuberculosis," *BMC Infectious Diseases*, 2009, p. 141, vol. 9.

Schlesinger, L.S. et al., "Binding of the Terminal Mannosyl Units of Lipoarabinomannan from a Virulent Strain of *Mycobacterium tuberculosis* to Human Macrophages," *J Immunol*, 1994, pp. 4070-4079, vol. 152, No. 8.

Shah, M. et al., "Diagnostic Accuracy of a Urine Lipoarabinomannan Test for Tuberculosis in Hospitalized Patients in a High HIV Prevalence Setting," *J Acquir Immune Defic Syndr*, 2009, pp. 145-151, vol. 52, No. 2.

Sharma, A. et al., "Specific and Randomly Derived Immunoactive Peptide Mimotopes of Mycobacterial Antigens," *Clinical and Vaccine Immunology*, 2006, pp. 1143-1154, vol. 13, No. 10.

Steingart, K.R. et al., "Commercial Serological Antibody Detection Tests for the Diagnosis of Pulmonary Tuberculosis: A Systematic Review," *PLoS Med*, 2007, p. e202, vol. 4, No. 6.

Steingart, K.R. et al., "Sputum processing methods to improve the sensitivity of smear microscopy for tuberculosis: a systematic review," *Lancet Infect Dis*, 2006, pp. 664-674, vol. 6, No. 10.

Tessema, T.A. et al., "Diagnostic Evaluation of Urinary Lipoarabinomannan at an Ethiopian Tuberculosis Centre," *Scand J Infect Dis*, 2001, p. 279-284, vol. 33, No. 4.

Thompson, C.R. et al., "Sphingosine Kinase 1 (SKI) is Recruited to Nascent Phagosomes in Human Macrophages: Inhibition of SKJ Translocation by *Mycobacterium tuberculosis*," *Journal of Immunology*, 2005, pp. 3551-3561, vol. 174, No. 6.

Torrelles, J.B. et al., "Identification of *Mycobacterium tuberculosis* Clinical Isolates with Altered Phagocytosis by Human Macrophages Due to a Truncated Lipoarabinomannan," *Journal of Biological Chemistry*, 2008, pp. 31417-31428, vol. 283, No. 46.

Vergne, I. et al., "Tuberculosis Toxin Blocking Phagosome Maturation Inhibits a Novel $Ca^{2+}$/Calmodulin-P/3K hVPS34 Cascade," *Journal of Experimental Medicine*, 2003, pp. 653-659, vol. 198, No. 4.

Welin, A. et al., "Incorporation of *Mycobacterium tuberculosis* Lipoarabinomannan into Macrophage Membrane Rafts Is a Prerequisite for the Phagosomal Maturation Block," *Infection and Immunity*, 2008, pp. 2882-2887, vol. 76, No. 7.

World Health Organization, "Diagnostics for Tuberculosis: Global demand and market potential," Special Programme for Research & Training in Tropical Diseases (TDR) sponsored by UNICEF/UNDP/World Bank/WHO, 2006, two hundred five pages.

World Health Organization, "Global Tuberculosis Control 2009: Epidemiology, Strategy, Financing," WHO Report 2009, three hundred fourteen pages.

Brown et al., "Tolerance to single, but not multiple, amino acid replacements in antibody V-H CDR2: A means of minimizing B cell wastage from somatic hypermutation?", *The Journal of Immunology*, The American Association of Immunologists, vol. 156, No. 9, Jan. 1, 1996, pp. 3285-3291.

EP12739329.6 , "Extended European Search Report", mailed May 11, 2015, 9 pages.

Wark et al., "Latest technologies for the enhancement of antibody affinity", *Advanced Drug Delivery Reviews*, Elsevier, Amsterdam, NL, vol. 58, No. 5-6, Aug. 7, 2006, pp. 657-670.

\* cited by examiner

Mannose  Galactose  Fuc  Lactose  Di-Arabinan

Maltotriose  Rhamnose  Branched Trimannose

Hexa-Mannan

Hexa-Arabinan

PATHOGENIC MYCOBACTERIA-DERIVED MANNOSE-CAPPED LIPOARABINOMANNAN ANTIGEN BINDING PROTEINS

CROSS REFERENCE TO RELATED APPLICATIONS

This application claims the benefit of U.S. Provisional Application No. 61/435,396, filed Jan. 24, 2011, which is hereby incorporated by reference in its entirety for all purposes.

SEQUENCE LISTING

The instant application contains a Sequence Listing which has been submitted in ASCII format via EFS-Web and is hereby incorporated by reference in its entirety. Said ASCII copy, created on Jul. 31, 2013, is named 20160US_CRF_Sequencelisting.txt and is 68,626 bytes in size.

BACKGROUND

Tuberculosis (TB) is a major human disease of significant public health importance with an estimated 9.27 million new cases and 1.77 million deaths in 2007 alone [1]. Current methods for the diagnosis of tuberculosis are either costly, e.g. PCR or IFN release assays, or slow, e.g., sputum culture, or insensitive, e.g., X-rays, sputum smears. However, immunoassays such as ELISA and immunofluorescence (IF) offer a rapid, sensitive and specific means of diagnosis. However, such assays require a suitable antigen expressed by *M. Tuberculosis* for detection plus the generation of high affinity monoclonal antibodies of suitable specificity.

Lipoarabinomannan (LAM) is a membrane bound glycolipid that has been found to be present in the urine of TB patients [2, 3]. Structural studies on mycobacterial lipoarabinomannan have shown that LAM secreted by pathogenic mycobacteria such as *M. avium*, *M. leprae*, *M. bovis* and *M. tuberculosis* all have a mannose sugar capping motif (hence the term ManLAM) while other non-pathogenic mycobacteria have different capping motifs such as phosphoinositide for *M. smegmatis* (PILAM) and no caps for *M. chelonae* (AraLAM) [4]. LAM has a core structure consisting of a mannosyl-phosphatidyl-myo-inositol lipid anchor attached to a highly branched polysaccharide [4]. The core lipid anchor has up to four fatty acid chains which are thought to anchor the LAM in the plasma membrane of the bacterium. LAM can be extracted from crude cell wall fraction using ethanol solvent or boiling with SDS, indicating that it is tightly integrated but not covalently bound to the cell wall [24]. The branched polysaccharide consists of a repeating α1-6 mannose backbone with α1-5 arabinose branches which are decorated with secondary arabinose branches with α1-3,5 and β1-2 linkages. These secondary branches terminate with capping motifs that vary between different groups of mycobacteria. At least three different capping motifs have been described: a phosphoinositide cap in fast growing mycobacteria such as *M. fortuitum* and *M. smegmatis*, a mannose cap with up to three α1-2 linked mannose residues in slow-growing mycobacteria, which include all major pathogenic species such as *M. tuberculosis*, *M. bovis*, *M. leprae* and *M. avium*. In addition, the fast growing mycobacterial species *M. chelonae* has been found to have no sugar caps on its secondary arabinose branches [4].

Antibodies are useful diagnostic and therapeutic tools and various techniques such as animal immunization, monoclonal hybridomas and antibody phage display have been developed and applied to produce a wide range of antibodies with excellent specificities. Phage display is a more recent development of recombinant technology that allows for the generation of specific monoclonal antibodies without the need for an in vivo immune system response. It involves the display of a diverse antibody collection, either synthetically generated or obtained either from naturally-derived naïve or immune antibody repertoires, on filamentous phages which package the genetic sequence of their individual antibodies. Repeated selection on the desired target results in enrichment for specific antibody-phage clones from which the coding sequences can be recovered and use to produce recombinant antibodies. Another advantage of this system is that selection of specific antibodies with particular characteristics such as slow off-rates or fast on-rates or binding at extremes of pH or temperature, which is not possible in an in vivo immunization, can be carried out [38].

Thus, there is a need for antibodies with specificity for the mannose caps of ManLAM that have high diagnostic specificity as well as the ability to block the immunomodulatory activity of mannose caps.

SUMMARY

Disclosed herein is an isolated antigen binding protein or fragment thereof (ABP) that specifically binds to an alpha 1-2 linkage mannose cap of Mannose-Capped Lipoarabinomannan (ManLAM). In some aspects, the ABP comprises CDR1, CDR2, and CDR3 of a polypeptide comprising amino acid sequences at least 90% identical to the amino acid sequences represented by SEQ ID NOS: 7, 8, and 9, respectively, and/or SEQ ID NOS: 27, 28, and 29, respectively, wherein the ABP exhibits an equilibrium dissociation constant (Kd) of between 2.268e-10 M and 5.133e-9 M for the alpha 1-2 linkage mannose cap of ManLAM, and wherein the ABP binds to the region of ManLAM recognized by a my2F12 monoclonal antibody. In some aspects, the ABP comprises the amino acid sequences shown in SEQ ID NO:15 and SEQ ID NO:18.

Also described herein is an isolated antigen binding protein or fragment thereof, comprising CDR1, CDR2, and CDR3 of a polypeptide comprising amino acid sequences at least 90% identical to the amino acid sequences represented by SEQ ID NOS: 7, 8, and 9, respectively, or SEQ ID NOS: 27, 28, and 29, respectively.

Also described herein is an isolated antigen binding protein or fragment thereof that specifically binds to an alpha 1-2 linkage mannose cap of ManLAM wherein the antigen binding protein is produced from a my2F12 antibody expressing cell.

Also described herein is an isolated antigen binding protein or fragment thereof that binds to a region of ManLAM, wherein the ABP binds to the region recognized by a my2F12 monoclonal antibody.

Also described herein is an isolated antigen binding protein or a portion thereof having binding specificity for an alpha 1-2 linkage mannose cap of ManLAM, wherein the antigen binding protein or the portion thereof exhibits a Kd of between about 2.268e-10 M and 5.133e-9 M.

In some aspects, the ABP has a Kd as shown in Table 2. In some aspects, the ABP has a Kd between about 2.268e-10 M and 5.133e-9 M. In some aspects, the antigen binding protein does not substantially bind a mannose oligosaccharide, a phosphoinositol mannoside (PIM), hexose, a pentose monomer, maltotriose, fucose, rhamnose, lactose, galactose, di-arabinan, hexa-arabinan, and/or *Nocardia cyriacigeorgica*.

In some aspects, the cap comprises a plurality of alpha 1-2 linkages. In some aspects, the cap comprises two or more alpha 1-2 linkages. In some aspects, the cap comprises three or more alpha 1-2 linkages.

In some aspects, the ABP binds to an epitope within the alpha 1-2 linkage mannose cap. In some aspects, the ABP binds to an epitope within the alpha 1-2 linkage mannose cap, wherein the epitope comprises a region within the alpha 1-2 linkage mannose cap. In some aspects, the ABP binds to an epitope within the alpha 1-2 linkage mannose cap, wherein the epitope consists of a region within the alpha 1-2 linkage mannose cap. In some aspects, the ABP binds to an epitope within the alpha 1-2 linkage mannose cap, wherein the epitope comprises a plurality of regions within the alpha 1-2 linkage mannose cap. In some aspects, the ABP binds to an epitope within the alpha 1-2 linkage mannose cap, wherein the epitope consists of a plurality of regions within the alpha 1-2 linkage mannose cap. In some aspects, the ABP binds to an epitope comprising the alpha 1-2 linkage mannose cap. In some aspects, the ABP binds to an epitope comprising one alpha 1-2 linkage mannose cap. In some aspects, the ABP binds to an epitope comprising a plurality of alpha 1-2 linkage mannose caps. In some aspects, the ABP binds to an epitope comprising the alpha 1-2 linkage mannose cap and one or more additional alpha 1-2 linkage mannose caps. In some aspects, the ABP binds to an epitope comprising the alpha 1-2 linkage mannose cap and two or more additional alpha 1-2 linkage mannose caps. In some aspects, the ABP binds to an epitope comprising the alpha 1-2 linkage mannose cap and three or more additional alpha 1-2 linkage mannose caps. In some aspects, the ABP binds to an epitope consisting of the alpha 1-2 linkage mannose cap.

In some aspects, the antigen binding protein is an antibody. In some aspects, the antigen binding protein is a monoclonal antibody. In some aspects, the antigen binding protein is a chimeric, humanized, veneered, or human antibody. In some aspects, the antigen binding protein is a humanized antibody. In some aspects, the antigen binding protein is a human antibody. In some aspects, the antigen binding protein is a monoclonal antibody. In some aspects, the antigen binding protein is a chimeric antibody. In some aspects, the antigen binding protein is a CDR-grafted antibody. In some aspects, the antigen binding protein is a variable region fragment. In some aspects, the antigen binding protein is a single domain antibody. In some aspects, the antigen binding protein is a single-chain Fv antibody. In some aspects, the antigen binding protein is a Fab antibody. In some aspects, the antigen binding protein is Fab' antibody. In some aspects, the antigen binding protein is a $(Fab')_2$ antibody. In some aspects, the antibody isotype is IgG1. In some aspects, the antigen binding protein is an antibody comprising at least one mutation in the constant region. In some aspects, the antibody isotype is IgG2 or IgG3.

In some aspects, the antigen binding protein comprises a polypeptide comprising an amino acid sequence at least 90% identical to the amino acid sequence represented by SEQ ID NO:7. In some aspects, the antigen binding protein comprises a polypeptide comprising an amino acid sequence at least 90% identical to the amino acid sequence represented by SEQ ID NO:8. In some aspects, the antigen binding protein comprises a polypeptide comprising an amino acid sequence at least 90% identical to the amino acid sequence represented by SEQ ID NO:9. In some aspects, the antigen binding protein comprises a polypeptide comprising an amino acid sequence at least 90% identical to the amino acid sequence represented by SEQ ID NO:10. In some aspects, the antigen binding protein comprises a polypeptide comprising an amino acid sequence at least 90% identical to the amino acid sequence represented by SEQ ID NO:11. In some aspects, the antigen binding protein comprises a polypeptide comprising an amino acid sequence at least 90% identical to the amino acid sequence represented by SEQ ID NO:12. In some aspects, the antigen binding protein comprises a polypeptide comprising an amino acid sequence at least 90% identical to the amino acid sequence represented by SEQ ID NO:13. In some aspects, the antigen binding protein comprises a polypeptide comprising an amino acid sequence at least 90% identical to the amino acid sequence represented by SEQ ID NO:14. In some aspects, the antigen binding protein comprises a polypeptide comprising an amino acid sequence at least 90% identical to the amino acid sequence represented by SEQ ID NO:15. In some aspects, the antigen binding protein comprises a polypeptide comprising an amino acid sequence at least 90% identical to the amino acid sequence represented by SEQ ID NO:16. In some aspects, the antigen binding protein comprises a polypeptide comprising an amino acid sequence at least 90% identical to the amino acid sequence represented by SEQ ID NO:17. In some aspects, the antigen binding protein comprises a polypeptide comprising an amino acid sequence at least 90% identical to the amino acid sequence represented by SEQ ID NO:18. In some aspects, the antigen binding protein comprises a polypeptide encoded by a nucleotide sequence at least 90% identical to the nucleotide sequence represented by SEQ ID NO:19. In some aspects, the antigen binding protein comprises a polypeptide encoded by a nucleotide sequence at least 90% identical to the nucleotide sequence represented by SEQ ID NO:20. In some aspects, the antigen binding protein comprises a polypeptide encoded by a nucleotide sequence at least 90% identical to the nucleotide sequence represented by SEQ ID NO:21. In some aspects, the antigen binding protein comprises a polypeptide encoded by a nucleotide sequence at least 90% identical to the nucleotide sequence represented by SEQ ID NO:22. In some aspects, the antigen binding protein comprises a polypeptide encoded by a nucleotide sequence at least 90% identical to the nucleotide sequence represented by SEQ ID NO:23. In some aspects, the antigen binding protein comprises a polypeptide encoded by a nucleotide sequence at least 90% identical to the nucleotide sequence represented by SEQ ID NO:24. In some aspects, the antigen binding protein comprises a polypeptide encoded by a nucleotide sequence at least 90% identical to the nucleotide sequence represented by SEQ ID NO:25. In some aspects, the antigen binding protein comprises a polypeptide encoded by a nucleotide sequence at least 90% identical to the nucleotide sequence represented by SEQ ID NO:26. In some aspects, the antigen binding protein comprises a polypeptide comprising an amino acid sequence at least 90% identical to the amino acid sequence represented by SEQ ID NO:27. In some aspects, the antigen binding protein comprises a polypeptide comprising an amino acid sequence at least 90% identical to the amino acid sequence represented by SEQ ID NO:28. In some aspects, the antigen binding protein comprises a polypeptide comprising an amino acid sequence at least 90% identical to the amino acid sequence represented by SEQ ID NO:29. In some aspects, the antigen binding protein comprises a polypeptide encoded by a nucleotide sequence at least 90% identical to the nucleotide sequence represented by SEQ ID NO:30. In some aspects, the antigen binding protein comprises a polypeptide comprising an amino acid sequence at least 90% identical to the amino acid sequence represented by SEQ ID NO:31. In some aspects, the antigen binding protein comprises a polypeptide encoded by a nucleotide sequence at least 90% identical to the nucleotide sequence represented by SEQ ID NO:32. In some aspects, the antigen binding protein comprises a polypeptide comprising an amino acid sequence at least 90% identical to the amino acid sequence represented by SEQ ID NO:33. In some aspects, the antigen binding protein comprises a polypeptide encoded by a nucleotide sequence at least 90% identical to the nucleotide sequence represented by SEQ ID NO:34. In some aspects, the antigen binding protein comprises a polypeptide comprising an amino acid sequence at least 90% identical to the amino acid sequence represented by SEQ ID NO:35. In some aspects, the antigen binding protein comprises a polypeptide encoded by a nucleotide sequence at least 90% identical to the nucleotide sequence represented by SEQ ID NO:36. In some aspects, the antigen binding protein comprises a polypeptide comprising an amino acid sequence at least 90% identical to the amino acid sequence represented by SEQ ID NO:37. In some aspects, the antigen binding protein comprises a polypeptide encoded by a nucleotide sequence at least 90% identical to the nucleotide sequence represented by SEQ ID NO:38. In some aspects, the antigen binding protein comprises a polypeptide comprising an amino acid sequence at least 90% identical to the amino acid sequence represented by SEQ ID NO:39. In some aspects, the antigen binding protein comprises a polypeptide encoded by a nucleotide sequence at least 90% identical to the nucleotide sequence represented by SEQ ID NO:40. In some aspects, the antigen binding protein comprises a polypeptide comprising an amino acid sequence at least 90% identical to the amino acid sequence represented by SEQ ID NO:41. In some aspects, the antigen binding protein comprises a polypeptide encoded by a nucleotide sequence at least 90% identical to the nucleotide sequence represented by SEQ ID NO:42. In some aspects, the antigen binding protein comprises a polypeptide comprising an amino acid sequence at least 90% identical to the amino acid sequence represented by SEQ ID NO:43. In some aspects, the antigen binding protein comprises a polypeptide encoded by a nucleotide sequence at least 90% identical to the nucleotide sequence represented by SEQ ID NO:44. In some aspects, the antigen binding protein comprises a polypeptide comprising an amino acid sequence at least 90% identical to the amino acid sequence represented by SEQ ID NO:45.

Also described herein is a pharmaceutical composition comprising at least one antigen binding protein disclosed herein and a pharmaceutically acceptable excipient.

Also disclosed herein is a nucleic acid molecule encoding at least one antigen binding protein disclosed herein.

Also disclosed herein is a recombinant expression vector comprising at least one nucleic acid molecule disclosed herein.

Also disclosed herein is a host cell transformed with at least one recombinant expression vector disclosed herein and/or at least one nucleic acid molecule disclosed herein.

Also disclosed herein is a method of making an antigen binding protein or fragment thereof that specifically binds to an alpha 1-2 linkage mannose cap of ManLAM, comprising: providing a host cell comprising a nucleic acid sequence that encodes the antigen binding protein; and maintaining the host cell under conditions in which the antigen binding protein is expressed. In some aspects, the ABP is an ABP disclosed herein.

Also disclosed herein is a method of making an ABP, comprising: obtaining a host cell comprising nucleic acids that encode an ABP that specifically binds to an alpha 1-2 linkage mannose cap of ManLAM; and maintaining the host cell under conditions in which the ABP is expressed. In some aspects, the ABP is an ABP disclosed herein. In some aspects, the method further includes collecting the ABP.

Also disclosed herein is a method of producing an ABP, comprising: culturing cells transformed with nucleic acids encoding the heavy and light chains of an ABP that specifically binds to an alpha 1-2 linkage mannose cap of ManLAM in a cell culture media, so that the cells secrete the ABP into the cell culture media; and purifying the ABP from the cell culture media. In some aspects, the ABP is an ABP disclosed herein.

Also disclosed herein is a method of producing a cell line producing an ABP, comprising: introducing a vector encoding heavy and light chains of the ABP and a selectable marker into cells; propagating the cells under conditions to select for one or more cells having increased copy number of the vector; isolating single cells from the one or more selected cells; and banking cells cloned from a single cell selected based on yield of ABP. In some aspects, the ABP is an ABP disclosed herein.

Also disclosed herein is a method for treating or preventing a condition associated with a pathogenic mycobacteria infection, comprising administering to a patient in need thereof an effective amount of an isolated antigen binding protein or fragment thereof that specifically binds to an alpha 1-2 linkage mannose cap of ManLAM. In some aspects, the ABP is an ABP disclosed herein.

Also disclosed herein is a method of reducing or eliminating a pathogenic mycobacteria infection, comprising administering to a subject in need thereof an effective amount of an ABP disclosed herein.

Also disclosed herein is an immunoassay for determining the presence or amount of a pathogenic mycobacteria infection in a sample, comprising: providing a reagent comprising an ABP that specifically binds to an alpha 1-2 linkage mannose cap of ManLAM; combining the ABP with the sample for a time sufficient for the ABP to bind to any pathogenic mycobacteria in the sample; and determining the presence or amount of pathogenic mycobacteria present in the sample based on specific binding of the ABP to the alpha 1-2 linkage mannose cap of ManLAM. In some aspects, the ABP is an ABP disclosed herein.

Also disclosed herein is an immunoassay device for detecting the presence or absence of a pathogenic mycobacteria in a sample, the device comprising: an ABP disclosed herein immobilized on a solid support.

Also disclosed herein is a method of determining the presence or absence of a pathogenic mycobacteria in a sample comprising contacting the sample suspected of comprising pathogenic mycobacteria with an effective amount of an antigen binding protein or fragment thereof that specifically binds to an alpha 1-2 linkage mannose cap of ManLAM, wherein binding of the antigen binding protein or fragment thereof indicates the presence of pathogenic mycobacteria. In some aspects, the method further includes detecting the binding of the antigen binding protein to ManLAM. In some aspects, the ABP is an ABP disclosed herein.

Also disclosed herein is a method of detecting the presence of a pathogenic mycobacteria in a sample, the method comprising contacting the sample with an ABP disclosed herein.

Also disclosed herein is a method for determining the presence or absence of a pathogenic mycobacteria in a subject, comprising: obtaining a sample from the subject; contacting the sample with an ABP that specifically binds to an alpha 1-2 linkage mannose cap of ManLAM; generating a complex between the ABP and the alpha 1-2 linkage mannose cap of ManLAM; detecting the complex to obtain a first dataset associated with the sample, wherein the first dataset comprises quantitative expression data for the alpha 1-2 linkage mannose cap of ManLAM; and analyzing the first dataset to determine the expression level of the alpha 1-2 linkage mannose cap of ManLAM, wherein the expression level of the alpha 1-2 linkage mannose cap of ManLAM positively correlates with an increased likelihood the subject is infected with pathogenic mycobacteria. In some aspects, the ABP is an ABP disclosed herein.

Also disclosed herein is a kit for detecting a pathogenic mycobacteria infection in a sample, the kit comprising an isolated antigen binding protein or fragment thereof that specifically binds to an alpha 1-2 linkage mannose cap of ManLAM in an amount effective to diagnose the infection. In some aspects, the kit includes a container containing the antigen binding protein in a formulation and instructions for use. In some aspects, the ABP is an ABP disclosed herein. In some aspects, the formulation is present in a vial or an injectable syringe. In some aspects, the antigen binding protein is bound to an array. In some aspects, the antigen binding protein is bound to a lateral-flow type test. In some aspects, the kit is used in an enzyme-linked immunosorbent assay (ELISA). In some aspects, the kit comprises instructions for determining whether the sample contains pathogenic mycobacteria. In some aspects, the kit comprises an agent suitable for detecting the binding between the antigen binding protein and ManLAM. In some aspects, the ABP is immobilized on a solid support. In some aspects, the kit comprises a detectable label.

BRIEF DESCRIPTION OF THE SEVERAL VIEWS OF THE DRAWINGS

These and other features, aspects, and advantages of the present invention will become better understood with regard to the following description, and accompanying drawings, where.

DETAILED DESCRIPTION

Antigen binding proteins (such as antibodies and functional binding fragments thereof) that bind to ManLAM are disclosed herein. In some embodiments, the antigen binding proteins (ABPs) bind to ManLAM and prevent ManLAM from functioning in various ways. In some embodiments, the antigen binding proteins block or reduce the ability of ManLAM to interact with other substances. In some embodiments, the antigen binding proteins are human monoclonal antibodies. In some embodiments, the antigen binding proteins are chimeric antibodies.

As will be appreciated by one of skill in the art, antigen binding proteins to ManLAM can be used in various methods and compositions for treating and/or diagnosing subjects with infection, such as pathogenic mycobacterial infections.

It is to be understood that both the foregoing general description and the following detailed description are exemplary and explanatory only and are not restrictive of the invention as claimed. In this application, the use of the singular includes the plural unless specifically stated otherwise. In this application, the use of "or" means "and/or" unless stated otherwise. Furthermore, the use of the term "including", as well as other forms, such as "includes" and "included", is not limiting. Also, terms such as "element" or "component" encompass both elements and components comprising one unit and elements and components that comprise more than one subunit unless specifically stated otherwise. Also, the use of the term "portion" can include part of a moiety or the entire moiety.

The section headings used herein are for organizational purposes only and are not to be construed as limiting the subject matter described. All documents, or portions of documents, cited in this application, including but not limited to patents, patent applications, articles, books, and treatises, are hereby expressly incorporated by reference in their entirety for any purpose. As utilized in accordance with the present disclosure, the following terms, unless otherwise indicated, shall be understood to have the following meanings:

The term "ManLAM activity" includes any biological effect of ManLAM.

Figure 2:
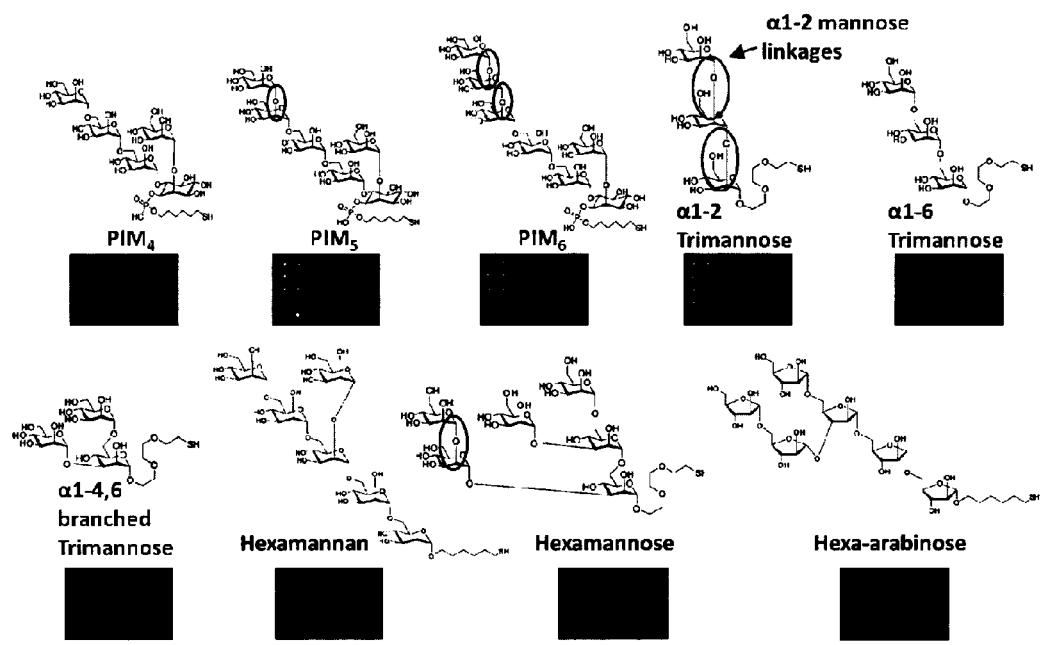
FIG. 2 shows carbohydrate microarray showing my2F12 specifically binding to oligosaccharides containing α1-2 mannose linkage. α1-2 mannose linkages are circled.
Figure 3:
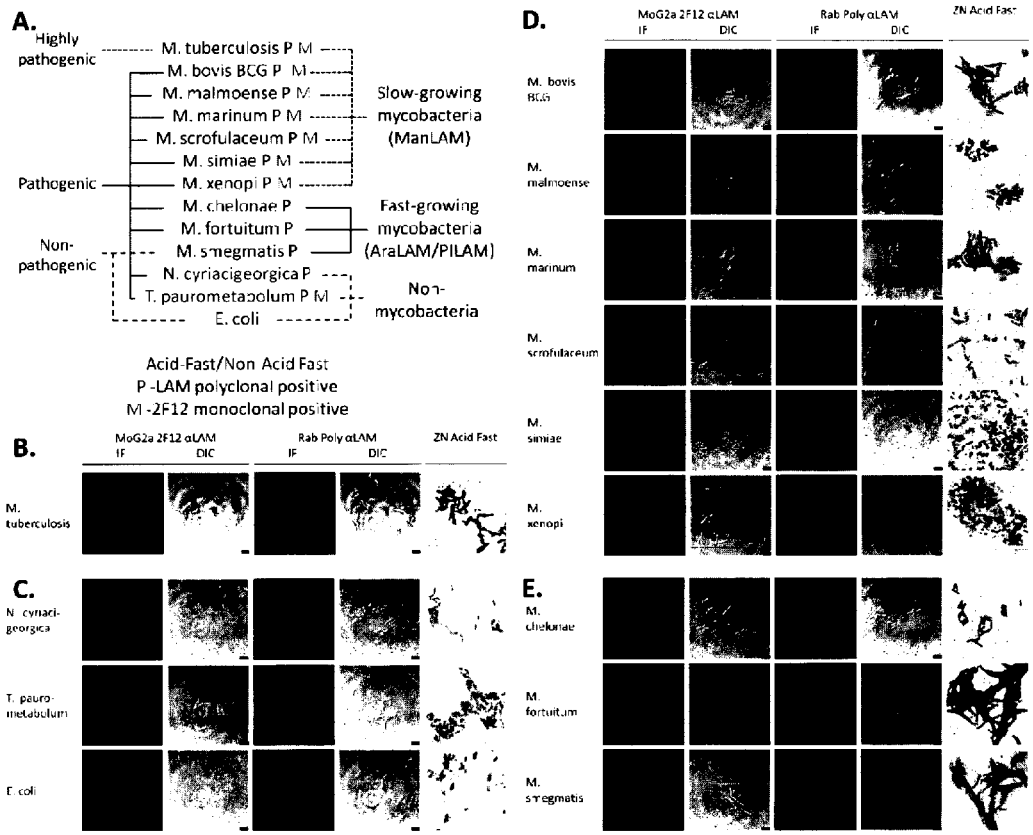
FIG. 3 shows (A) Tree diagram showing classification of mycobacterial and non-mycobacterial species and their pathogenicity, antibody specificity and acid-fast staining. (B-D) Immunofluorescence with my2F12 mouse chimeric antibody (MoG2a 2F12 αLAM) and polyclonal αLAM (Rab Poly αLAM) on confocal with corresponding differential interference contrast (DIC) microscopy images and acid-fast staining for slow-growing mycobacteria (B), fastgrowing mycobacteria (C) and non-mycobacterial (D) species.
Figure 5:
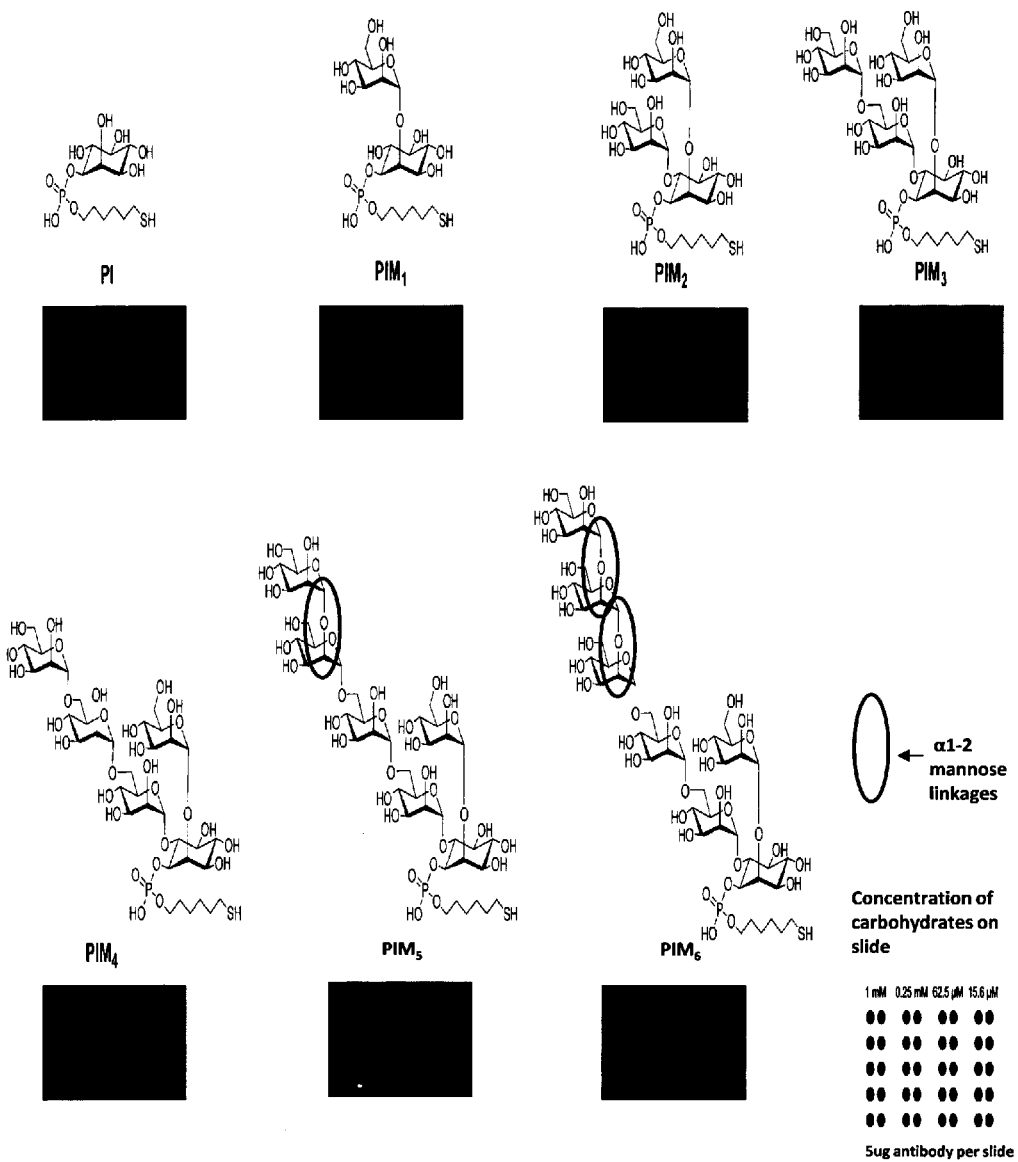
FIG. 5 shows detection of carbohydrate moieties on LAM recognized by antibody my2F12. α1-2 linkages are circled.
Figure 5:
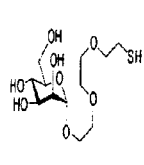
Figure 5:
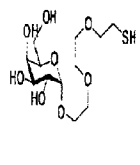
Figure 5:
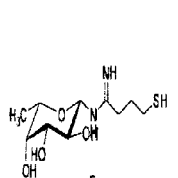
Figure 5:
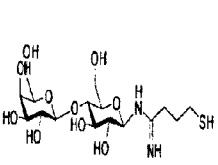
Figure 5:
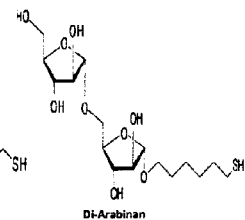
Figure 5:
Figure 5:
Figure 5:
Figure 5:
Figure 5:
Figure 5:
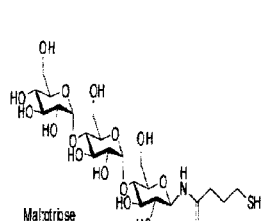
Figure 5:
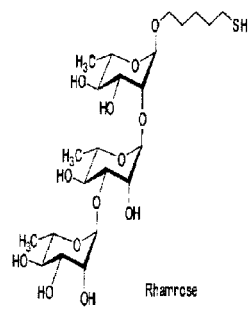
Figure 5:
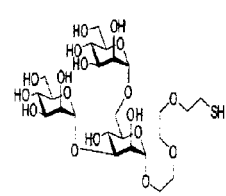
Figure 5:
Figure 5:
Figure 5:
Figure 5:
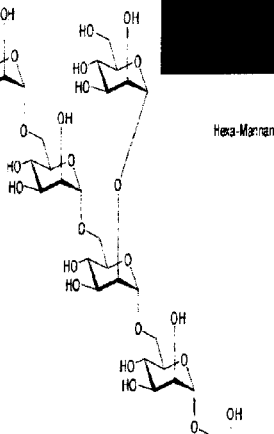
Figure 5:
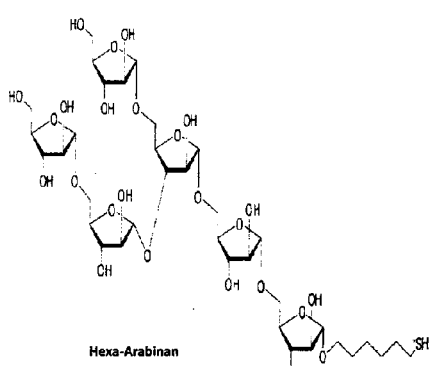
Figure 5:
Figure 5:
Figure 5:
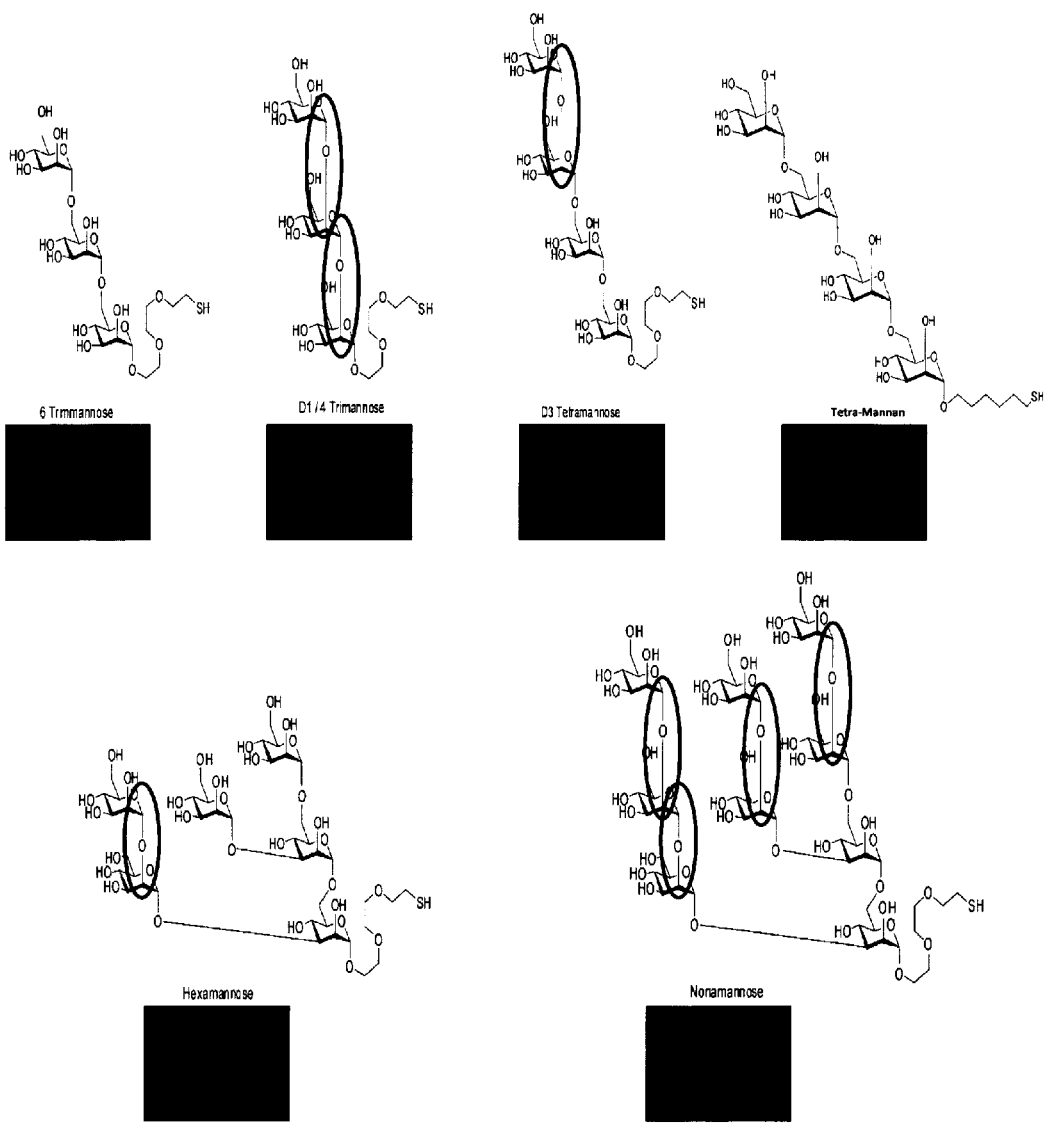
Figure 6:
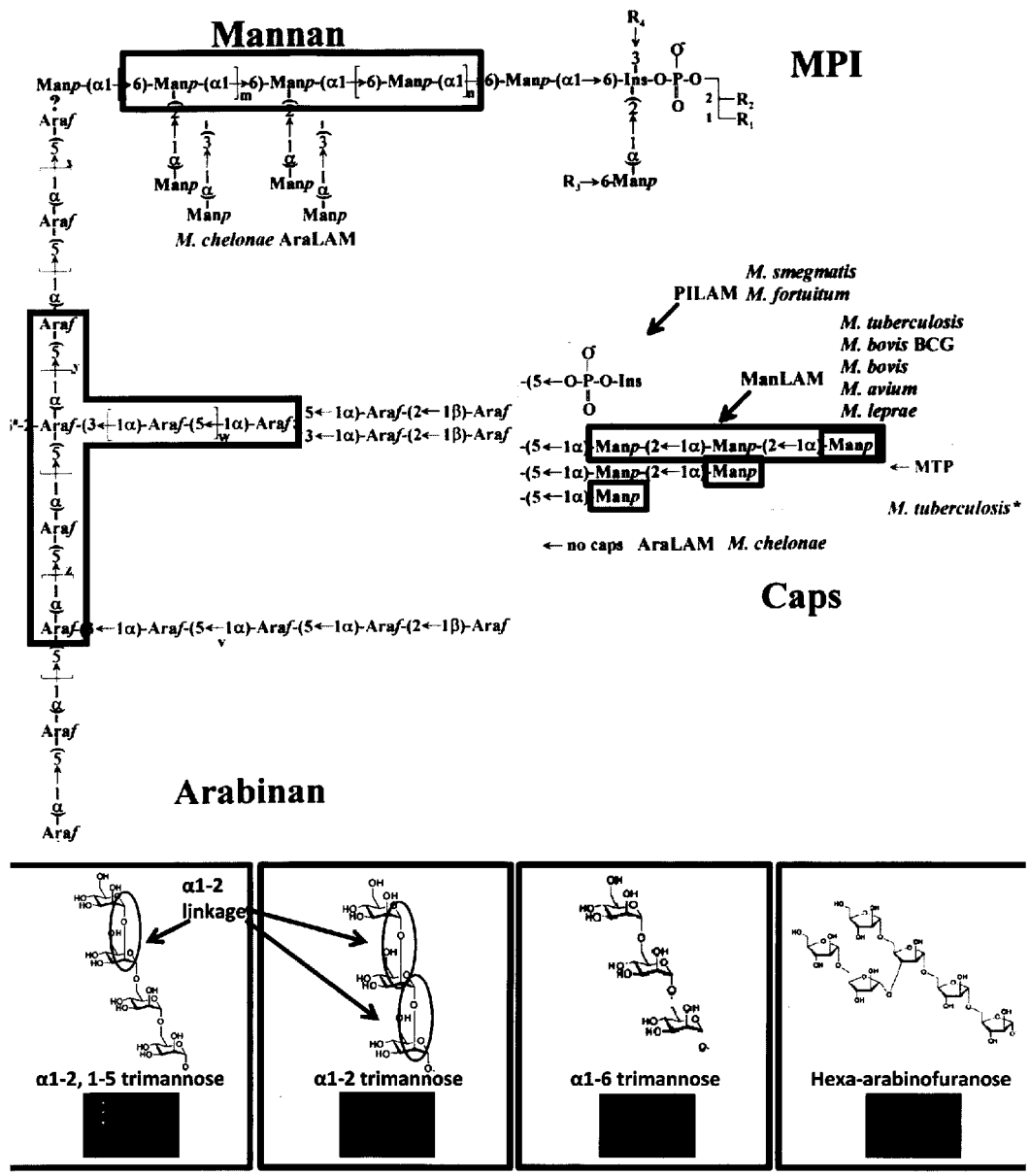
FIG. 6 shows the location of the my2F12 epitope (α1-2 mannose linkage and capping motif) on ManLAM and the structure of lipoarabinomannan (See Nigou, J., M. Gilleron, and G. Puzo, *Lipoarabinomannans: from structure to biosynthesis*. Biochimie, 2003. 85(1-2): p. 153-66; herein incorporated by reference in its entirety for all purposes). Also shown are synthetic carbohydrate analogues representing various regions of the lipoarabinomannan molecule (indicated by 4 lower boxes) and specific binding of my2F12 to the terminal α1-2 mannose capping motif as indicated by carbohydrate microarray (4 black boxes within the 4 lower boxes). α1-2 linkages are circled in the lower, left 2 boxes. See also FIG. 5.
Figure 7:
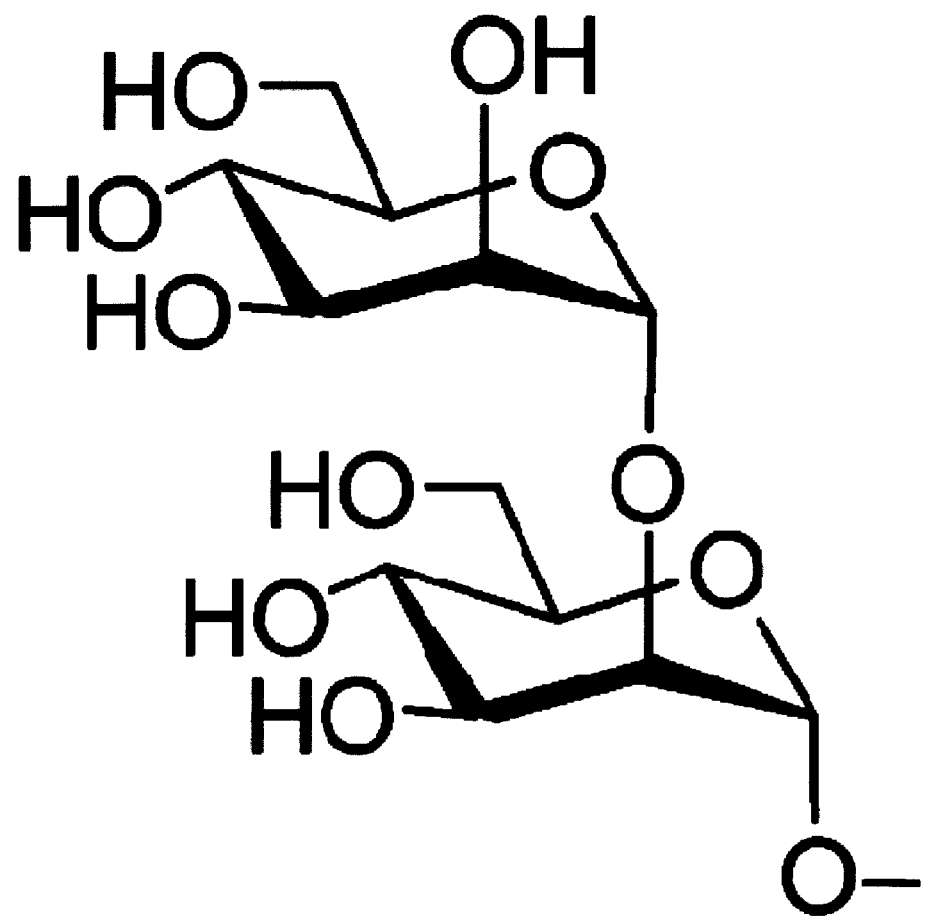
FIG. 7 shows the structure of a terminal α1-2 linkage mannose cap of ManLAM with a single α1-2 linkage.

The term "alpha 1-2 linkage mannose cap of Mannose-Capped Lipoarabinomannan (ManLAM)" refers to the location of the my2F12 epitope (the α1-2 mannose linkage and capping motif) on ManLAM. The structure of lipoarabinomannan is shown in FIG. 6. See Nigou, J., M. Gilleron, and G. Puzo, *Lipoarabinomannans: from structure to biosynthesis*. Biochimie, 2003. 85(1-2): p. 153-66; herein incorporated by reference in its entirety for all purposes. The structure of a terminal α1-2 linkage mannose cap of ManLAM with a single α1-2 linkage is shown in FIG. 7. Examples of synthetic carbohydrate analogues representing various regions of the lipoarabinomannan molecule are shown in FIGS. 5-6. α1-2 linkages are circled in FIGS. 2 and 5-6. Thus, the epitope of an antigen binding protein disclosed herein can include a region of an alpha 1-2 linkage mannose cap of ManLAM, an alpha 1-2 linkage mannose cap of ManLAM, or a plurality of alpha 1-2 linkage mannose caps of ManLAM. Other examples of ABP epitopes related to an alpha 1-2 linkage mannose cap of ManLAM are described herein.

The term "polynucleotide" or "nucleic acid" includes both single-stranded and double-stranded nucleotide polymers. The nucleotides comprising the polynucleotide can be ribonucleotides or deoxyribonucleotides or a modified form of either type of nucleotide. The modifications include base modifications such as bromouridine and inosine derivatives, ribose modifications such as 2',3'-dideoxyribose, and internucleotide linkage modifications such as phosphorothioate, phosphorodithioate, phosphoroselenoate, phosphorodiselenoate, phosphoroanilothioate, phoshoraniladate and phosphoroamidate.

The term "oligonucleotide" means a polynucleotide comprising 200 or fewer nucleotides. In some embodiments, oligonucleotides are 10 to 60 bases in length. In other embodiments, oligonucleotides are 12, 13, 14, 15, 16, 17, 18, 19, or 20 to 40 nucleotides in length. Oligonucleotides can be single stranded or double stranded, e.g., for use in the construction of a mutant gene. Oligonucleotides can be sense or antisense oligonucleotides. An oligonucleotide can include a label, including a radiolabel, a fluorescent label, a hapten or an antigenic label, for detection assays. Oligonucleotides can be used, for example, as PCR primers, cloning primers or hybridization probes.

An "isolated nucleic acid molecule" means a DNA or RNA of genomic, mRNA, cDNA, or synthetic origin or some combination thereof which is not associated with all or a portion of a polynucleotide in which the isolated polynucleotide is found in nature, or is linked to a polynucleotide to which it is not linked in nature. For purposes of this disclosure, it should be understood that "a nucleic acid molecule comprising" a particular nucleotide sequence does not encompass intact chromosomes. Isolated nucleic acid molecules "comprising" specified nucleic acid sequences can include, in addition to the specified sequences, coding sequences for up to ten or even up to twenty other proteins or portions thereof, or can include operably linked regulatory sequences that control expression of the coding region of the recited nucleic acid sequences, and/or can include vector sequences.

Unless specified otherwise, the left-hand end of any single-stranded polynucleotide sequence discussed herein is the 5' end; the left-hand direction of double-stranded polynucleotide sequences is referred to as the 5' direction. The direction of 5' to 3' addition of nascent RNA transcripts is referred to as the transcription direction; sequence regions on the DNA strand having the same sequence as the RNA transcript that are 5' to the 5' end of the RNA transcript are referred to as "upstream sequences;" sequence regions on the DNA strand having the same sequence as the RNA transcript that are 3' to the 3' end of the RNA transcript are referred to as "downstream sequences."

The term "control sequence" refers to a polynucleotide sequence that can affect the expression and processing of coding sequences to which it is ligated. The nature of such control sequences can depend upon the host organism. In particular embodiments, control sequences for prokaryotes can include a promoter, a ribosomal binding site, and a transcription termination sequence. For example, control sequences for eukaryotes can include promoters comprising one or a plurality of recognition sites for transcription factors, transcription enhancer sequences, and transcription termination sequence. "Control sequences" can include leader sequences and/or fusion partner sequences.

The term "vector" means any molecule or entity (e.g., nucleic acid, plasmid, bacteriophage or virus) used to transfer protein coding information into a host cell.

The term "expression vector" or "expression construct" refers to a vector that is suitable for transformation of a host cell and contains nucleic acid sequences that direct and/or control (in conjunction with the host cell) expression of one or more heterologous coding regions operatively linked thereto. An expression construct can include, but is not limited to, sequences that affect or control transcription, translation, and, if introns are present, affect RNA splicing of a coding region operably linked thereto.

As used herein, "operably linked" means that the components to which the term is applied are in a relationship that allows them to carry out their inherent functions under suitable conditions. For example, a control sequence in a vector that is "operably linked" to a protein coding sequence is ligated thereto so that expression of the protein coding sequence is achieved under conditions compatible with the transcriptional activity of the control sequences.

The term "host cell" means a cell that has been transformed, or is capable of being transformed, with a nucleic acid sequence and thereby expresses a gene of interest. The term includes the progeny of the parent cell, whether or not the progeny is identical in morphology or in genetic make-up to the original parent cell, so long as the gene of interest is present.

The term "transfection" means the uptake of foreign or exogenous DNA by a cell, and a cell has been "transfected" when the exogenous DNA has been introduced inside the cell membrane. A number of transfection techniques are well known in the art and are disclosed herein. See, e.g., Graham et al., 1973, Virology 52:456; Sambrook et al., 2001, Molecular Cloning: A Laboratory Manual, supra; Davis et al., 1986, Basic Methods in Molecular Biology, Elsevier; Chu et al., 1981, Gene 13:197. Such techniques can be used to introduce one or more exogenous DNA moieties into suitable host cells.

The term "transformation" refers to a change in a cell's genetic characteristics, and a cell has been transformed when it has been modified to contain new DNA or RNA. For example, a cell is transformed where it is genetically modified from its native state by introducing new genetic material via transfection, transduction, or other techniques. Following transfection or transduction, the transforming DNA can recombine with that of the cell by physically integrating into a chromosome of the cell, or can be maintained transiently as an episomal element without being replicated, or can replicate independently as a plasmid. A cell is considered to have been "stably transformed" when the transforming DNA is replicated with the division of the cell.

The terms "polypeptide" or "protein" means a macromolecule having the amino acid sequence of a native protein, that is, a protein produced by a naturally-occurring and non-recombinant cell; or it is produced by a genetically-engineered or recombinant cell, and comprise molecules having the amino acid sequence of the native protein, or molecules having deletions from, additions to, and/or substitutions of one or more amino acids of the native sequence. The term also includes amino acid polymers in which one or more amino acids are chemical analogs of a corresponding naturally-occurring amino acid and polymers. The terms "polypeptide" and "protein" specifically encompass ManLAM antigen binding proteins, antibodies, or sequences that have deletions from, additions to, and/or substitutions of one or more amino acid of antigen-binding protein. The term "polypeptide fragment" refers to a polypeptide that has an amino-terminal deletion, a carboxyl-terminal deletion, and/or an internal deletion as compared with the full-length native protein. Such fragments can also contain modified amino acids as compared with the native protein. In certain embodiments, fragments are about five to 500 amino acids long. For example, fragments can be at least 5, 6, 8, 10, 14, 20, 50, 70, 100, 110, 150, 200, 250, 300, 350, 400, or 450 amino acids long. Useful polypeptide fragments include immunologically functional fragments of antibodies, including binding domains. In the case of a ManLAM-binding antibody, useful fragments include but are not limited to a CDR region, a variable domain of a heavy and/or light chain, a portion of an antibody chain or just its variable region including two CDRs, and the like.

The term "isolated protein" referred means that a subject protein (1) is free of at least some other proteins with which it would normally be found, (2) is essentially free of other proteins from the same source, e.g., from the same species, (3) is expressed by a cell from a different species, (4) has been separated from at least about 50 percent of polynucleotides, lipids, carbohydrates, or other materials with which it is associated in nature, (5) is operably associated (by covalent or noncovalent interaction) with a polypeptide with which it is not associated in nature, or (6) does not occur in nature. Typically, an "isolated protein" constitutes at least about 5%, at least about 10%, at least about 25%, or at least about 50% of a given sample. Genomic DNA, cDNA, mRNA or other RNA, of synthetic origin, or any combination thereof can encode such an isolated protein. Preferably, the isolated protein is substantially free from proteins or polypeptides or other contaminants that are found in its natural environment that would interfere with its therapeutic, diagnostic, prophylactic, research or other use.

The term "amino acid" includes its normal meaning in the art.

A "variant" of a polypeptide (e.g., an antigen binding protein, or an antibody) comprises an amino acid sequence wherein one or more amino acid residues are inserted into, deleted from and/or substituted into the amino acid sequence relative to another polypeptide sequence. Variants include fusion proteins.

The term "identity" refers to a relationship between the sequences of two or more polypeptide molecules or two or more nucleic acid molecules, as determined by aligning and comparing the sequences. "Percent identity" means the percent of identical residues between the amino acids or nucleotides in the compared molecules and is calculated based on the size of the smallest of the molecules being compared. For these calculations, gaps in alignments (if any) are preferably addressed by a particular mathematical model or computer program (i.e., an "algorithm"). Methods that can be used to calculate the identity of the aligned nucleic acids or polypeptides include those described in Computational Molecular Biology, (Lesk, A. M., ed.), 1988, New York: Oxford University Press; Biocomputing Informatics and Genome Projects, (Smith, D. W., ed.), 1993, New York: Academic Press; Computer Analysis of Sequence Data, Part I, (Griffin, A. M., and Griffin, H. G., eds.), 1994, New Jersey: Humana Press; von Heinje, G., 1987, Sequence Analysis in Molecular Biology, New York: Academic Press; Sequence Analysis Primer, (Gribskov, M. and Devereux, J., eds.), 1991, New York: M. Stockton Press; and Carillo et al., 1988, SIAM J. Applied Math. 48:1073.

In calculating percent identity, the sequences being compared are typically aligned in a way that gives the largest match between the sequences. One example of a computer program that can be used to determine percent identity is the GCG program package, which includes GAP (Devereux et al., 1984, Nucl. Acid Res. 12:387; Genetics Computer Group, University of Wisconsin, Madison, Wis.). The computer algorithm GAP is used to align the two polypeptides or polynucleotides for which the percent sequence identity is to be determined. The sequences are aligned for optimal matching of their respective amino acid or nucleotide (the "matched span", as determined by the algorithm). A gap opening penalty (which is calculated as 3× the average diagonal, wherein the "average diagonal" is the average of the diagonal of the comparison matrix being used; the "diagonal" is the score or number assigned to each perfect amino acid match by the particular comparison matrix) and a gap extension penalty (which is usually $\frac{1}{10}$ times the gap opening penalty), as well as a comparison matrix such as PAM 250 or BLOSUM 62 are used in conjunction with the algorithm. In certain embodiments, a standard comparison matrix (see, Dayhoff et al., 1978, Atlas of Protein Sequence and Structure 5:345-352 for the PAM 250 comparison matrix; Henikoff et al., 1992, Proc. Natl. Acad. Sci. U.S.A. 89:10915-10919 for the BLOSUM 62 comparison matrix) is also used by the algorithm.

Examples of parameters that can be employed in determining percent identity for polypeptides or nucleotide sequences using the GAP program are the following: Algorithm: Needleman et al., 1970, J. Mol. Biol. 48:443-453; Comparison matrix: BLOSUM 62 from Henikoff et al., 1992, supra; Gap Penalty: 12 (but with no penalty for end gaps); Gap Length Penalty: 4; Threshold of Similarity: 0.

Certain alignment schemes for aligning two amino acid sequences may result in matching of only a short region of the two sequences, and this small aligned region may have very high sequence identity even though there is no significant relationship between the two full-length sequences. Accordingly; the selected alignment method (GAP program) can be adjusted if so desired to result in an alignment that spans at least 50 or other number of contiguous amino acids of the target polypeptide.

As used herein, the twenty conventional (e.g., naturally occurring) amino acids and their abbreviations follow conventional usage. See Immunology—A Synthesis (2nd Edition, E. S. Golub and D. R. Gren, Eds., Sinauer Associates, Sunderland, Mass. (1991)), which is incorporated herein by reference for any purpose. Stereoisomers (e.g., D-amino acids) of the twenty conventional amino acids, unnatural amino acids such as αα-disubstituted amino acids, N-alkyl amino acids, lactic acid, and other unconventional amino acids can also be suitable components for polypeptides of the present invention. Examples of unconventional amino acids include: 4-hydroxyproline, gamma-carboxyglutamate, epsilon-N,N,N-trimethyllysine, .epsilon.-N-acetyllysine, O-phosphoserine, N-acetylserine, N-formylmethionine, 3-methylhistidine, 5-hydroxylysine, sigma-N-methylarginine, and other similar amino acids and imino acids (e.g., 4-hydroxyproline). In the polypeptide notation used herein, the left-hand direction is the amino terminal direction and the right-hand direction is the carboxy-terminal direction, in accordance with standard usage and convention.

Conservative amino acid substitutions can encompass non-naturally occurring amino acid residues, which are typically incorporated by chemical peptide synthesis rather than by synthesis in biological systems. These include peptidomimetics and other reversed or inverted forms of amino acid moieties.

Naturally occurring residues can be divided into classes based on common side chain properties: 1) hydrophobic: norleucine, Met, Ala, Val, Leu, Ile; 2) neutral hydrophilic: Cys, Ser, Thr, Asn, Gln; 3) acidic: Asp, Glu; 4) basic: His, Lys, Arg; 5) residues that influence chain orientation: Gly, Pro; and 6) aromatic: Trp, Tyr, Phe. For example, non-conservative substitutions can involve the exchange of a member of one of these classes for a member from another class. Such substituted residues can be introduced, for example, into regions of a human antibody that are homologous with non-human antibodies, or into the non-homologous regions of the molecule.

In making changes to the antigen binding protein or the MANLAM protein, according to certain embodiments, the hydropathic index of amino acids can be considered. Each amino acid has been assigned a hydropathic index on the basis of its hydrophobicity and charge characteristics. They are: isoleucine (+4.5); valine (+4.2); leucine (+3.8); phenylalanine (+2.8); cysteine/cystine (+2.5); methionine (+1.9); alanine (+1.8); glycine (−0.4); threonine (−0.7); serine (−0.8); tryptophan (−0.9); tyrosine (−1.3); proline (−1.6); histidine (−3.2); glutamate (−3.5); glutamine (−3.5); aspartate (−3.5); asparagine (−3.5); lysine (−3.9); and arginine (−4.5).

The importance of the hydropathic amino acid index in conferring interactive biological function on a protein is understood in the art. Kyte et al., J. Mol. Biol., 157:105-131 (1982). It is known that certain amino acids can be substituted for other amino acids having a similar hydropathic index or score and still retain a similar biological activity. In making changes based upon the hydropathic index, in certain embodiments, the substitution of amino acids whose hydropathic indices are within +/−2 is included. In certain embodiments, those which are within +/−1 are included, and in certain embodiments, those within +/−0.5 are included.

It is also understood in the art that the substitution of like amino acids can be made effectively on the basis of hydrophilicity, particularly where the biologically functional protein or peptide thereby created is intended for use in immunological embodiments, as in the present case. In certain embodiments, the greatest local average hydrophilicity of a protein, as governed by the hydrophilicity of its adjacent amino acids, correlates with its immunogenicity and antigenicity, i.e., with a biological property of the protein.

The following hydrophilicity values have been assigned to these amino acid residues: arginine (+3.0); lysine (+3.0); aspartate (+3.0.+−0.1); glutamate (+3.0.+−0.1); serine (+0.3); asparagine (+0.2); glutamine (+0.2); glycine (0); threonine (−0.4); proline (−0.5.+−0.1); alanine (−0.5); histidine (−0.5); cysteine (−1.0); methionine (−1.3); valine (−1.5); leucine (−1.8); isoleucine (−1.8); tyrosine (−2.3); phenylalanine (−2.5) and tryptophan (−3.4). In making changes based upon similar hydrophilicity values, in certain embodiments, the substitution of amino acids whose hydrophilicity values are within +/−2 is included, in certain embodiments, those which are within +/−1 are included, and in certain embodiments, those within +/−0.5 are included. One can also identify epitopes from primary amino acid sequences on the basis of hydrophilicity. These regions are also referred to as "epitopic core regions."

The term "derivative" refers to a molecule that includes a chemical modification other than an insertion, deletion, or substitution of amino acids (or nucleic acids). In certain embodiments, derivatives comprise covalent modifications, including, but not limited to, chemical bonding with polymers, lipids, or other organic or inorganic moieties. In certain embodiments, a chemically modified antigen binding protein can have a greater circulating half-life than an antigen binding protein that is not chemically modified. In certain embodiments, a chemically modified antigen binding protein can have improved targeting capacity for desired cells, tissues, and/or organs. In some embodiments, a derivative antigen binding protein is covalently modified to include one or more water soluble polymer attachments, including, but not limited to, polyethylene glycol, polyoxyethylene glycol, or polypropylene glycol. See, e.g., U.S. Pat. Nos. 4,640,835, 4,496,689, 4,301,144, 4,670,417, 4,791,192 and 4,179,337. In certain embodiments, a derivative antigen binding protein comprises one or more polymer, including, but not limited to, monomethoxy-polyethylene glycol, dextran, cellulose, or other carbohydrate based polymers, poly-(N-vinyl pyrrolidone)-polyethylene glycol, propylene glycol homopolymers, a polypropylene oxide/ethylene oxide co-polymer, polyoxyethylated polyols (e.g., glycerol) and polyvinyl alcohol, as well as mixtures of such polymers.

In certain embodiments, a derivative is covalently modified with polyethylene glycol (PEG) subunits. In certain embodiments, one or more water-soluble polymer is bonded at one or more specific position, for example at the amino terminus, of a derivative. In certain embodiments, one or more water-soluble polymer is randomly attached to one or more side chains of a derivative. In certain embodiments, PEG is used to improve the therapeutic capacity for an antigen binding protein. In certain embodiments, PEG is used to improve the therapeutic capacity for a humanized antibody. Certain such methods are discussed, for example, in U.S. Pat. No. 6,133,426, which is hereby incorporated by reference for any purpose.

Peptide analogs are commonly used in the pharmaceutical industry as non-peptide drugs with properties analogous to those of the template peptide. These types of non-peptide compound are termed "peptide mimetics" or "peptidomimetics." Fauchere, J., Adv. Drug Res., 15:29 (1986); Veber & Freidinger, TINS, p. 392 (1985); and Evans et al., J. Med. Chem., 30:1229 (1987), which are incorporated herein by reference for any purpose. Such compounds are often developed with the aid of computerized molecular modeling. Peptide mimetics that are structurally similar to therapeutically useful peptides can be used to produce a similar therapeutic or prophylactic effect. Generally, peptidomimetics are structurally similar to a paradigm polypeptide (i.e., a polypeptide that has a biochemical property or pharmacological activity), such as human antibody, but have one or more peptide linkages optionally replaced by a linkage selected from: —CH2 NH—, —CH2 S—, —CH2-CH2-, —CH.dbd.CH-(cis and trans), —COCH2-, —CH(OH)CH2-, and —CH2 SO—, by methods well known in the art. Systematic substitution of one or more amino acids of a consensus sequence with a D-amino acid of the same type (e.g., D-lysine in place of L-lysine) can be used in certain embodiments to generate more stable peptides. In addition, constrained peptides comprising a consensus sequence or a substantially identical consensus sequence variation can be generated by methods known in the art (Rizo and Gierasch, Ann. Rev. Biochem., 61:387 (1992), incorporated herein by reference for any purpose); for example, by adding internal cysteine residues capable of forming intramolecular disulfide bridges which cyclize the peptide.

The term "naturally occurring" as used throughout the specification in connection with biological materials such as polypeptides, nucleic acids, host cells, and the like, refers to materials which are found in nature or a form of the materials that is found in nature.

An "antigen binding protein" ("ABP") as used herein means any protein that binds a specified target antigen. In the instant application, the specified target antigen is the Man- LAM antigen or fragment thereof. "Antigen binding protein" includes but is not limited to antibodies and binding parts thereof, such as immunologically functional fragments. Peptibodies are another example of antigen binding proteins. The term "immunologically functional fragment" (or simply "fragment") of an antibody or immunoglobulin chain (heavy or light chain) antigen binding protein, as used herein, is a species of antigen binding protein comprising a portion (regardless of how that portion is obtained or synthesized) of an antibody that lacks at least some of the amino acids present in a full-length chain but which is still capable of specifically binding to an antigen. Such fragments are biologically active in that they bind to the target antigen and can compete with other antigen binding proteins, including intact antibodies, for binding to a given epitope. In some embodiments, the fragments are neutralizing fragments. These biologically active fragments can be produced by recombinant DNA techniques, or can be produced by enzymatic or chemical cleavage of antigen binding proteins, including intact antibodies. Immunologically functional immunoglobulin fragments include, but are not limited to, Fab, a diabody (heavy chain variable domain on the same polypeptide as a light chain variable domain, connected via a short peptide linker that is too short to permit pairing between the two domains on the same chain), Fab', F(ab')2, Fv, domain antibodies and single-chain antibodies, and can be derived from any mammalian source, including but not limited to human, mouse, rat, camelid or rabbit. It is further contemplated that a functional portion of the antigen binding proteins disclosed herein, for example, one or more CDRs, could be covalently bound to a second protein or to a small molecule to create a therapeutic agent directed to a particular target in the body, possessing bifunctional therapeutic properties, or having a prolonged serum half-life. As will be appreciated by one of skill in the art, an antigen binding protein can include nonprotein components.

Certain antigen binding proteins described herein are antibodies or are derived from antibodies. In certain embodiments, the polypeptide structure of the antigen binding proteins is based on antibodies, including, but not limited to, monoclonal antibodies, bispecific antibodies, minibodies, domain antibodies, synthetic antibodies (sometimes referred to herein as "antibody mimetics"), chimeric antibodies, humanized antibodies, human antibodies, antibody fusions (sometimes referred to herein as "antibody conjugates"), and fragments thereof, respectively. In some embodiments, the ABP comprises or consists of avimers (tightly binding peptide). These various antigen binding proteins are further described herein.

An "Fc" region comprises two heavy chain fragments comprising the CH1 and CH2 domains of an antibody. The two heavy chain fragments are held together by two or more disulfide bonds and by hydrophobic interactions of the CH3 domains.

A "Fab fragment" comprises one light chain and the CH1 and variable regions of one heavy chain. The heavy chain of a Fab molecule cannot form a disulfide bond with another heavy chain molecule.

A "Fab' fragment" comprises one light chain and a portion of one heavy chain that contains the VH domain and the CH1 domain and also the region between the CH1 and CH2 domains, such that an interchain disulfide bond can be formed between the two heavy chains of two Fab' fragments to form an F(ab')2 molecule.

A "F(ab')2 fragment" contains two light chains and two heavy chains containing a portion of the constant region between the CH1 and CH2 domains, such that an interchain disulfide bond is formed between the two heavy chains. A F(ab')2 fragment thus is composed of two Fab' fragments that are held together by a disulfide bond between the two heavy chains.

The "Fv region" comprises the variable regions from both the heavy and light chains, but lacks the constant regions.

"Single-chain antibodies" are Fv molecules in which the heavy and light chain variable regions have been connected by a flexible linker to form a single polypeptide chain, which forms an antigen binding region. Single chain antibodies are discussed in detail in International Patent Application Publication No. WO 88/01649 and U.S. Pat. No. 4,946,778 and U.S. Pat. No. 5,260,203, the disclosures of which are incorporated by reference.

A "domain antibody" is an immunologically functional immunoglobulin fragment containing only the variable region of a heavy chain or the variable region of a light chain. In some instances, two or more VH regions are covalently joined with a peptide linker to create a bivalent domain antibody. The two VH regions of a bivalent domain antibody can target the same or different antigens.

A "bivalent antigen binding protein" or "bivalent antibody" comprises two antigen binding sites. In some instances, the two binding sites have the same antigen specificities. Bivalent antigen binding proteins and bivalent antibodies can be bispecific, see, infra A bivalent antibody other than a "multispecific" or "multifunctional" antibody, in certain embodiments, typically is understood to have each of its binding sites identical.

A "multispecific antigen binding protein" or "multispecific antibody" is one that targets more than one antigen or epitope.

A "bispecific," "dual-specific" or "bifunctional" antigen binding protein or antibody is a hybrid antigen binding protein or antibody, respectively, having two different antigen binding sites. Bispecific antigen binding proteins and antibodies are a species of multispecific antigen binding protein antibody and can be produced by a variety of methods including, but not limited to, fusion of hybridomas or linking of Fab' fragments. See, e.g., Songsivilai and Lachmann, 1990, Clin. Exp. Immunol. 79:315-321; Kostelny et al., 1992, J. Immunol. 148:1547-1553. The two binding sites of a bispecific antigen binding protein or antibody will bind to two different epitopes, which can reside on the same or different protein targets.

An antigen binding protein is said to "specifically bind" its target antigen when the dissociation constant (Kd) is $\leq 10^{-8}$ M. The ABP specifically binds antigen with "high affinity" when the Kd is $\leq 5 \times 10^{-9}$ M, and with "very high affinity" when the Kd is $\leq 5 \times 10^{-10}$ M. In one embodiment, the ABP has a Kd of $\leq 10^{-9}$ M. In one embodiment, the off-rate is $\leq 1 \times 10^{-5}$. In other embodiments, the ABPs will bind to ManLAM with a Kd of between about $10^{-9}$ M and about $10^{-13}$ M, and in yet another embodiment the ABPs will bind with a Kd$\leq 5 \times 10^{-10}$. In some embodiments, the ABP will bind to ManLAM with a Kd as shown in Table 2. As will be appreciated by one of skill in the art, in some embodiments, any or all of the antigen binding fragments can specifically bind to ManLAM.

An antigen binding protein is "selective" when it binds to one target more tightly than it binds to a second target.

"Antigen binding region" means a protein, or a portion of a protein, that specifically binds a specified antigen (e.g., a paratope). For example, that portion of an antigen binding protein that contains the amino acid residues that interact with an antigen and confer on the antigen binding protein its specificity and affinity for the antigen is referred to as "antigen binding region." An antigen binding region typically includes one or more "complementary binding regions" ("CDRs").

Certain antigen binding regions also include one or more "framework" regions. A "CDR" is an amino acid sequence that contributes to antigen binding specificity and affinity. "Framework" regions can aid in maintaining the proper conformation of the CDRs to promote binding between the antigen binding region and an antigen. Structurally, framework regions can be located in antibodies between CDRs.

In certain aspects, recombinant antigen binding proteins that bind ManLAM are provided. In this context, a "recombinant antigen binding protein" is a protein made using recombinant techniques, i.e., through the expression of a recombinant nucleic acid as described herein. Methods and techniques for the production of recombinant proteins are well known in the art.

The term "antibody" refers to an intact immunoglobulin of any isotype, or a fragment thereof that can compete with the intact antibody for specific binding to the target antigen, and includes, for instance, chimeric, humanized, fully human, and bispecific antibodies. An "antibody" is a species of an antigen binding protein. An intact antibody will generally comprise at least two full-length heavy chains and two full-length light chains, but in some instances can include fewer chains such as antibodies naturally occurring in camelids which can comprise only heavy chains. Antibodies can be derived solely from a single source, or can be "chimeric," that is, different portions of the antibody can be derived from two different antibodies as described further below. The antigen binding proteins, antibodies, or binding fragments can be produced in hybridomas, by recombinant DNA techniques, or by enzymatic or chemical cleavage of intact antibodies. Unless otherwise indicated, the term "antibody" includes, in addition to antibodies comprising two full-length heavy chains and two full-length light chains, derivatives, variants, fragments, and muteins thereof, examples of which are described below. Furthermore, unless explicitly excluded, antibodies include monoclonal antibodies, bispecific antibodies, minibodies, domain antibodies, synthetic antibodies (sometimes referred to herein as "antibody mimetics"), chimeric antibodies, humanized antibodies, human antibodies, antibody fusions (sometimes referred to herein as "antibody conjugates"), and fragments thereof, respectively. In some embodiments, the term also encompasses peptibodies.

Naturally occurring antibody structural units typically comprise a tetramer. Each such tetramer typically is composed of two identical pairs of polypeptide chains, each pair having one full-length "light" (in certain embodiments, about 25 kDa) and one full-length "heavy" chain (in certain embodiments, about 50-70 kDa). The amino-terminal portion of each chain typically includes a variable region of about 100 to 10 or more amino acids that typically is responsible for antigen recognition. The carboxy-terminal portion of each chain typically defines a constant region that can be responsible for effector function. Human light chains are typically classified as kappa and lambda light chains. Heavy chains are typically classified as mu, delta, gamma, alpha, or epsilon, and define the antibody's isotype as IgM, IgD, IgG, IgA, and IgE, respectively. IgG has several subclasses, including, but not limited to, IgG1, IgG2, IgG3, and IgG4. IgM has subclasses including, but not limited to, IgM1 and IgM2. IgA is similarly subdivided into subclasses including, but not limited to, IgA1 and IgA2. Within full-length light and heavy chains, typically, the variable and constant regions are joined by a "J" region of about 12 or more amino acids, with the heavy chain also including a "D" region of about 10 more amino acids. See, e.g., Fundamental Immunology, Ch. 7 (Paul, W., ed., 2nd ed. Raven Press, N.Y. (1989)) (incorporated by reference in its entirety for all purposes). The variable regions of each light/heavy chain pair typically form the antigen binding site.

The variable regions typically exhibit the same general structure of relatively conserved framework regions (FR) joined by three hyper variable regions, also called complementarity determining regions or CDRs. The CDRs from the two chains of each pair typically are aligned by the framework regions, which can enable binding to a specific epitope. From N-terminal to C-terminal, both light and heavy chain variable regions typically comprise the domains FR1, CDR1, FR2, CDR2, FR3, CDR3 and FR4. The assignment of amino acids to each domain is typically in accordance with the definitions of Kabat Sequences of Proteins of Immunological Interest (National Institutes of Health, Bethesda, Md. (1987 and 1991)), or Chothia & Lesk, J. Mol. Biol., 196:901-917 (1987); Chothia et al., Nature, 342:878-883 (1989).

In certain embodiments, an antibody heavy chain binds to an antigen in the absence of an antibody light chain. In certain embodiments, an antibody light chain binds to an antigen in the absence of an antibody heavy chain. In certain embodiments, an antibody binding region binds to an antigen in the absence of an antibody light chain. In certain embodiments, an antibody binding region binds to an antigen in the absence of an antibody heavy chain. In certain embodiments, an individual variable region specifically binds to an antigen in the absence of other variable regions.

In certain embodiments, definitive delineation of a CDR and identification of residues comprising the binding site of an antibody is accomplished by solving the structure of the antibody and/or solving the structure of the antibody-ligand complex. In certain embodiments, that can be accomplished by any of a variety of techniques known to those skilled in the art, such as X-ray crystallography. In certain embodiments, various methods of analysis can be employed to identify or approximate the CDR regions. Examples of such methods include, but are not limited to, the Kabat definition, the Chothia definition, the AbM definition and the contact definition.

The Kabat definition is a standard for numbering the residues in an antibody and is typically used to identify CDR regions. See, e.g., Johnson & Wu, Nucleic Acids Res., 28: 214-8 (2000). The Chothia definition is similar to the Kabat definition, but the Chothia definition takes into account positions of certain structural loop regions. See, e.g., Chothia et al., J. Mol. Biol., 196: 901-17 (1986); Chothia et al., Nature, 342: 877-83 (1989). The AbM definition uses an integrated suite of computer programs produced by Oxford Molecular Group that model antibody structure. See, e.g., Martin et al., Proc Natl Acad Sci (USA), 86:9268-9272 (1989); "AbM™, A Computer Program for Modeling Variable Regions of Antibodies," Oxford, UK; Oxford Molecular, Ltd. The AbM definition models the tertiary structure of an antibody from primary sequence using a combination of knowledge databases and ab initio methods, such as those described by Samudrala et al., "Ab Initio Protein Structure Prediction Using a Combined Hierarchical Approach," in PROTEINS, Structure, Function and Genetics Suppl., 3:194-198 (1999). The contact definition is based on an analysis of the available complex crystal structures. See, e.g., MacCallum et al., J. Mol. Biol., 5:732-45 (1996).

By convention, the CDR regions in the heavy chain are typically referred to as H1, H2, and H3 and are numbered sequentially in the direction from the amino terminus to the carboxy terminus. The CDR regions in the light chain are typically referred to as L1, L2, and L3 and are numbered sequentially in the direction from the amino terminus to the carboxy terminus.

The term "light chain" includes a full-length light chain and fragments thereof having sufficient variable region sequence to confer binding specificity. A full-length light chain includes a variable region domain, VL, and a constant region domain, CL. The variable region domain of the light chain is at the amino-terminus of the polypeptide. Light chains include kappa chains and lambda chains.

The term "heavy chain" includes a full-length heavy chain and fragments thereof having sufficient variable region sequence to confer binding specificity. A full-length heavy chain includes a variable region domain, VH, and three constant region domains, CH1, CH2, and CH3. The VH domain is at the amino-terminus of the polypeptide, and the CH domains are at the carboxyl-terminus, with the CH3 being closest to the carboxy-terminus of the polypeptide. Heavy chains can be of any isotype, including IgG (including IgG1, IgG2, IgG3 and IgG4 subtypes), IgA (including IgA1 and IgA2 subtypes), IgM and IgE.

A bispecific or bifunctional antibody typically is an artificial hybrid antibody having two different heavy/light chain pairs and two different binding sites. Bispecific antibodies can be produced by a variety of methods including, but not limited to, fusion of hybridomas or linking of Fab' fragments. See, e.g., Songsivilai et al., Clin. Exp. Immunol., 79: 315-321 (1990); Kostelny et al., J. Immunol., 148:1547-1553 (1992).

Some species of mammals also produce antibodies having only a single heavy chain.

Each individual immunoglobulin chain is typically composed of several "immunoglobulin domains," each consisting of roughly 90 to 110 amino acids and having a characteristic folding pattern. These domains are the basic units of which antibody polypeptides are composed. In humans, the IgA and IgD isotypes contain four heavy chains and four light chains; the IgG and IgE isotypes contain two heavy chains and two light chains; and the IgM isotype contains five heavy chains and five light chains. The heavy chain C region typically comprises one or more domains that can be responsible for effector function. The number of heavy chain constant region domains will depend on the isotype. IgG heavy chains, for example, contain three C region domains known as CH1, CH2 and CH3. The antibodies that are provided can have any of these isotypes and subtypes. In certain embodiments of the present invention, an anti-ManLAM antibody is of the IgG1 subtype.

The term "variable region" or "variable domain" refers to a portion of the light and/or heavy chains of an antibody, typically including approximately the amino-terminal 120 to 130 amino acids in the heavy chain and about 100 to 110 amino terminal amino acids in the light chain. In certain embodiments, variable regions of different antibodies differ extensively in amino acid sequence even among antibodies of the same species. The variable region of an antibody typically determines specificity of a particular antibody for its target The term "neutralizing antigen binding protein" or "neutralizing antibody" refers to an antigen binding protein or antibody, respectively, that binds to a ligand and prevents or reduces the biological effect of that ligand. This can be done, for example, by directly blocking a binding site on the ligand or by binding to the ligand and altering the ligand's ability to bind through indirect means (such as structural or energetic alterations in the ligand). In some embodiments, the term can also denote an antigen binding protein that prevents the protein to which it is bound from performing a biological function. In assessing the binding and/or specificity of an antigen binding protein, e.g., an antibody or immunologically functional fragment thereof, an antibody or fragment can substantially inhibit binding of a ligand to its binding partner when an excess of antibody reduces the quantity of binding partner bound to the ligand by at least about 1-20, 20-30%, 30-40%, 40-50%, 50-60%, 60-70%, 70-80%, 80-85%, 85-90%, 90-95%, 95-97%, 97-98%, 98-99% or more (as measured in an in vitro competitive binding assay). In some embodiments, the neutralizing ability is characterized and/or described via a competition assay. In some embodiments, the neutralizing ability is described in terms of an IC50 or EC50 value.

The term "target" refers to a molecule or a portion of a molecule capable of being bound by an antigen binding protein. In certain embodiments, a target is an antigen. The use of "antigen" in the phrase "antigen binding protein" simply denotes that the moiety that comprises the antigen can be bound by an antibody.

The term "compete" when used in the context of antigen binding proteins (e.g., neutralizing antigen binding proteins or neutralizing antibodies) that compete for the same epitope means competition between antigen binding proteins as determined by an assay in which the antigen binding protein (e.g., antibody or immunologically functional fragment thereof) being tested prevents or inhibits (e.g., reduces) specific binding of a reference antigen binding protein (e.g., a ligand, or a reference antibody) to a common antigen (e.g., ManLAM or a fragment thereof). Numerous types of competitive binding assays can be used to determine if one antigen binding protein competes with another, for example: solid phase direct or indirect radioimmunoassay (RIA), solid phase direct or indirect enzyme immunoassay (EIA), sandwich competition assay (see, e.g., Stahli et al., 1983, Methods in Enzymology 9:242-253); solid phase direct biotin-avidin EIA (see, e.g., Kirkland et al., 1986, J. Immunol. 137:3614-3619) solid phase direct labeled assay, solid phase direct labeled sandwich assay (see, e.g., Harlow and Lane, 1988, Antibodies, A Laboratory Manual, Cold Spring Harbor Press); solid phase direct label RIA using 1-125 label (see, e.g., Morel et al., 1988, Molec. Immunol. 25:7-15); solid phase direct biotin-avidin EIA (see, e.g., Cheung, et al., 1990, Virology 176:546-552); and direct labeled RIA (Moldenhauer et al., 1990, Scand. J. Immunol. 32:77-82). Typically, such an assay involves the use of purified antigen bound to a solid surface or cells bearing either of these, an unlabelled test antigen binding protein and a labeled reference antigen binding protein. Competitive inhibition is measured by determining the amount of label bound to the solid surface or cells in the presence of the test antigen binding protein. Usually the test antigen binding protein is present in excess. Antigen binding proteins identified by competition assay (competing antigen binding proteins) include antigen binding proteins binding to the same epitope as the reference antigen binding proteins and antigen binding proteins binding to an adjacent epitope sufficiently proximal to the epitope bound by the reference antigen binding protein for steric hindrance to occur. Additional details regarding methods for determining competitive binding are provided in the examples herein. Usually, when a competing antigen binding protein is present in excess, it will inhibit (e.g., reduce) specific binding of a reference antigen binding protein to a common antigen by at least 40-45%, 45-50%, 50-55%, 55-60%, 60-65%, 65-70%, 70-75% or 75% or more. In some instances, binding is inhibited by at least 80-85%, 85-90%, 90-95%, 95-97%, or 97% or more.

The term "antigen" refers to a molecule or a portion of a molecule capable of being bound by a selective binding agent, such as an antigen binding protein (including, e.g., an antibody or immunological functional fragment thereof). In some embodiments, the antigen is capable of being used in an animal to produce antibodies capable of binding to that antigen.

The term "epitope" includes any determinant capable being bound by an antigen binding protein, such as an antibody or to a T-cell receptor. An epitope is a region of an antigen that is bound by an antigen binding protein that targets that antigen. Epitope determinants can include chemically active surface groupings of molecules such as amino acids, sugar side chains, phosphoryl or sulfonyl groups, and can have specific three dimensional structural characteristics, and/or specific charge characteristics. Generally, antibodies specific for a particular target antigen will preferentially recognize an epitope on the target antigen in a complex mixture of proteins and/or macromolecules.

As used herein, "substantially pure" means that the described species of molecule is the predominant species present, that is, on a molar basis it is more abundant than any other individual species in the same mixture. In certain embodiments, a substantially pure molecule is a composition wherein the object species comprises at least 50% (on a molar basis) of all macromolecular species present. In other embodiments, a substantially pure composition will comprise at least 80%, 85%, 90%, 95%, or 99% of all macromolecular species present in the composition. In other embodiments, the object species is purified to essential homogeneity wherein contaminating species cannot be detected in the composition by conventional detection methods and thus the composition consists of a single detectable macromolecular species.

The term "agent" is used herein to denote a chemical compound, a mixture of chemical compounds, a biological macromolecule, or an extract made from biological materials.

As used herein, the terms "label" or "labeled" refers to incorporation of a detectable marker, e.g., by incorporation of a radiolabeled amino acid or attachment to a polypeptide of biotin moieties that can be detected by marked avidin (e.g., streptavidin containing a fluorescent marker or enzymatic activity that can be detected by optical or colorimetric methods). In certain embodiments, the label or marker can also be therapeutic. Various methods of labeling polypeptides and glycoproteins are known in the art and can be used. Examples of labels for Examples of labels for polypeptides include, but are not limited to, the following: radioisotopes or radionuclides (e.g. $^3$H, $^{14}$C, $^{15}$N, $^{35}$S, $^{90}$Y, $^{99}$Tc, $^{111}$In, $^{125}$I, $^{131}$I), fluorescent labels (e.g., FITC, rhodamine, lanthanide phosphors), enzymatic labels (e.g., horseradish peroxidase, .beta.-galactosidase, luciferase, alkaline phosphatase), chemiluminescent, biotinyl groups, predetermined polypeptide epitopes recognized by a secondary reporter (e.g., leucine zipper pair sequences, binding sites for secondary antibodies, metal binding domains, epitope tags). In certain embodiments, labels are attached by spacer arms of various lengths to reduce potential steric hindrance.

The term "biological sample", as used herein, includes, but is not limited to, any quantity of a substance from a living thing or formerly living thing. Such living things include, but are not limited to, humans, mice, monkeys, rats, rabbits, and other animals. Such substances include, but are not limited to, blood, serum, urine, cells, organs, tissues, bone, bone marrow, lymph nodes, and skin.

The term "pharmaceutical agent composition" (or agent or drug) as used herein refers to a chemical compound, composition, agent or drug capable of inducing a desired therapeutic effect when properly administered to a patient. It does not necessarily require more than one type of ingredient.

The term "therapeutically effective amount" refers to the amount of a ManLAM antigen binding protein determined to produce a therapeutic response in a mammal. Such therapeutically effective amounts are readily ascertained by one of ordinary skill in the art.

The term "modulator," as used herein, is a compound that changes or alters the activity or function of a molecule. For example, a modulator can cause an increase or decrease in the magnitude of a certain activity or function of a molecule compared to the magnitude of the activity or function observed in the absence of the modulator. In certain embodiments, a modulator is an inhibitor, which decreases the magnitude of at least one activity or function of a molecule. Certain exemplary activities and functions of a molecule include, but are not limited to, binding affinity, enzymatic activity, and signal transduction. Certain exemplary inhibitors include, but are not limited to, proteins, peptides, antibodies, peptibodies, carbohydrates or small organic molecules. Peptibodies are described in, e.g., U.S. Pat. No. 6,660,843 (corresponding to PCT Application No. WO 01/83525).

The terms "patient" and "subject" are used interchangeably and include human and non-human animal subjects as well as those with formally diagnosed disorders, those without formally recognized disorders, those receiving medical attention, those at risk of developing the disorders, etc.

The term "treat" and "treatment" includes therapeutic treatments, prophylactic treatments, and applications in which one reduces the risk that a subject will develop a disorder or other risk factor. Treatment does not require the complete curing of a disorder and encompasses embodiments in which one reduces symptoms or underlying risk factors.

The term "prevent" does not require the 100% elimination of the possibility of an event. Rather, it denotes that the likelihood of the occurrence of the event has been reduced in the presence of the compound or method.

Standard techniques can be used for recombinant DNA, oligonucleotide synthesis, and tissue culture and transformation (e.g., electroporation, lipofection). Enzymatic reactions and purification techniques can be performed according to manufacturer's specifications or as commonly accomplished in the art or as described herein. The foregoing techniques and procedures can be generally performed according to conventional methods well known in the art and as described in various general and more specific references that are cited and discussed throughout the present specification. See, e.g., Sambrook et al., Molecular Cloning: A Laboratory Manual (2d ed., Cold Spring Harbor Laboratory Press, Cold Spring Harbor, N.Y. (1989)), which is incorporated herein by reference for any purpose. Unless specific definitions are provided, the nomenclatures utilized in connection with, and the laboratory procedures and techniques of, analytical chemistry, synthetic organic chemistry, and medicinal and pharmaceutical chemistry described herein are those well known and commonly used in the art. Standard techniques can be used for chemical syntheses, chemical analyses, pharmaceutical preparation, formulation, and delivery, and treatment of patients.

ManLAM Antigen Binding Proteins

Antigen binding proteins (ABPs) that bind ManLAM are provided herein. In some embodiments, the antigen binding proteins provided are polypeptides which comprise one or more complementary determining regions (CDRs), as described herein. In some antigen binding proteins, the CDRs are embedded into a "framework" region, which orients the CDR(s) such that the proper antigen binding properties of the CDR(s) is achieved.

In some embodiments, the antigen binding proteins provided herein are capable of inhibiting ManLAM-associated activity (including binding). In some embodiments, antigen binding proteins binding to these epitopes inhibit, inter alia, physiological effects mediated by ManLAM. In some embodiments, the antigen binding proteins are human, such as fully human antibodies to ManLAM.

In some embodiments, the ABP binds to the alpha 1-2 linkage mannose caps of ManLAM. In some embodiments, the ABP binds to a mannose cap with up to three alpha 1-2 linked mannose residues. In some embodiments, the ABP binds to LAM with a mannose sugar capping motif.

The antigen binding proteins that are disclosed herein have a variety of utilities. Some of the antigen binding proteins, for instance, are useful in specific binding assays, affinity purification of ManLAM, and in screening assays to identify other antagonists of ManLAM activity. Some of the antigen binding proteins are useful for inhibiting ManLAM-mediated activities.

The antigen binding proteins can be used in a variety of therapeutic applications, as explained herein. For example, in some embodiments the ManLAM antigen binding proteins are useful for treating conditions associated with ManLAM, such as pathogenic mycobacteria infection, as further described herein. Other uses for the antigen binding proteins include, for example, diagnosis of ManLAM-associated diseases or conditions and screening assays to determine the presence or absence of ManLAM. Some of the antigen binding proteins described herein are useful in treating consequences, symptoms, and/or the pathology associated with ManLAM activity and/or associated bacterial infection.

In some embodiments, the antigen binding proteins that are provided comprise one or more CDRs (e.g., 1, 2, 3, 4, 5 or 6 CDRs). In some embodiments, the antigen binding protein comprises (a) a polypeptide structure and (b) one or more CDRs that are inserted into and/or joined to the polypeptide structure. The polypeptide structure can take a variety of different forms. For example, it can be, or comprise, the framework of a naturally occurring antibody, or fragment or variant thereof, or can be completely synthetic in nature.

In certain embodiments, the polypeptide structure of the antigen binding proteins is an antibody or is derived from an antibody, including, but not limited to, monoclonal antibodies, bispecific antibodies, minibodies, domain antibodies, synthetic antibodies (sometimes referred to herein as "antibody mimetics"), chimeric antibodies, humanized antibodies, antibody fusions (sometimes referred to as "antibody conjugates"), and portions or fragments of each, respectively. In some instances, the antigen binding protein is an immunological fragment of an antibody (e.g., a Fab, a Fab', a F(ab')2, or a scFv).

In embodiments where the antigen binding protein is used for therapeutic applications, an antigen binding protein can inhibit, interfere with or modulate one or more biological activities of ManLAM. In one embodiment, an antigen binding protein binds specifically to ManLAM. Some of the antigen binding proteins that are provided herein are antibodies. In some embodiments, the ABP has a Kd of less (binding more tightly) than $10^{-7}$, $10^{-8}$, $10^{-9}$, $10^{-10}$, $10^{-11}$, $10^{-12}$, or $10^{-13}$ M (or any integer within these range of numbers). In some embodiments, the ABP has an $IC_{50}$ of less than 1 microM, 1000 nM to 100 nM, 100 mM to 10 nM, 1 nM to 1 nM, 1000 pM to 500 pM, 500 pM to 200 pM, less than 200 pM, 200 pM to 150 pM, 200 pM to 100 pM, 100 pM to 10 pM, 10 pM to 1 pM (or any integer within these range of numbers).

Variable regions of immunoglobulin chains generally exhibit the same overall structure, comprising relatively conserved framework regions (FR) joined by three hypervariable regions, more often called "complementarity determining regions" or CDRs. The CDRs from the two chains of each heavy chain/light chain pair mentioned above typically are aligned by the framework regions to form a structure that binds specifically with a specific epitope on the target (e.g., ManLAM). From N-terminal to C-terminal, naturally-occurring light and heavy chain variable regions both typically conform with the following order of these elements: FR1, CDR1, FR2, CDR2, FR3, CDR3 and FR4. A numbering system has been devised for assigning numbers to amino acids that occupy positions in each of these domains. This numbering system is defined in Kabat Sequences of Proteins of Immunological Interest (1987 and 1991, NIH, Bethesda, Md.), or Chothia & Lesk, 1987, J. Mol. Biol. 196:901-917; Chothia et al., 1989, Nature 342:878-883.

Human Antigen Binding Proteins (e.g., Antibodies)

As described herein, an antigen binding protein that binds to ManLAM can comprise a human (i.e., fully human) antibody and/or part thereof. In certain embodiments, nucleotide sequences encoding, and amino acid sequences comprising, heavy and light chain immunoglobulin molecules, particularly sequences corresponding to the variable regions are provided. In certain embodiments, sequences corresponding to complementarity determining regions (CDR's), specifically from CDR1 through CDR3, are provided. According to certain embodiments, a hybridoma cell line expressing such an immunoglobulin molecule is provided. According to certain embodiments, a hybridoma cell line expressing such a monoclonal antibody is provided. In certain embodiments, a purified human monoclonal antibody to ManLAM is provided. In certain embodiments, a purified chimeric antibody to ManLAM is provided.

One can engineer mouse strains deficient in mouse antibody production with large fragments of the human Ig loci in anticipation that such mice would produce human antibodies in the absence of mouse antibodies. Large human Ig fragments can preserve the large variable gene diversity as well as the proper regulation of antibody production and expression. By exploiting the mouse machinery for antibody diversification and selection and the lack of immunological tolerance to human proteins, the reproduced human antibody repertoire in these mouse strains can yield high affinity fully human antibodies against any antigen of interest, including human antigens. Using the hybridoma technology, antigen-specific human mAbs with the desired specificity can be produced and selected. Certain exemplary methods are described in WO 98/24893, U.S. Pat. No. 5,545,807, EP 546073, and EP 546073.

In certain embodiments, one can use constant regions from species other than human along with the human variable region(s).

The ability to clone and reconstruct megabase sized human loci in yeast artificial chromosomes (YACs) and to introduce them into the mouse germline provides an approach to elucidating the functional components of very large or crudely mapped loci as well as generating useful models of human disease. Furthermore, the utilization of such technology for substitution of mouse loci with their human equivalents could provide insights into the expression and regulation of human gene products during development, their communication with other systems, and their involvement in disease induction and progression.

Human antibodies avoid some of the problems associated with antibodies that possess murine or rat variable and/or constant regions. The presence of such murine or rat derived proteins can lead to the rapid clearance of the antibodies or can lead to the generation of an immune response against the antibody by a patient. In order to avoid the utilization of murine or rat derived antibodies, fully human antibodies can be generated through the introduction of functional human antibody loci into a rodent, other mammal or animal so that the rodent, other mammal or animal produces fully human antibodies.

Humanized antibodies are those antibodies that, while initially starting off containing antibody amino acid sequences that are not human, have had at least some of these nonhuman antibody amino acid sequences replaced with human antibody sequences. This is in contrast with human antibodies, in which the antibody is encoded (or capable of being encoded) by genes possessed a human.

Antigen Binding Protein Variants

Other antibodies that are provided are variants of the ABPs described in this application and comprise variable light and/or variable heavy chains that each have at least 50%, 50-60%, 60-70%, 70-80%, 80-85%, 85-90%, 90-95%, 95-97%, 97-99%, or above 99% identity to the amino acid sequences of ABPs described herein (either the entire sequence or a subpart of the sequence, e.g., one or more CDR). In some instances, such antibodies include at least one heavy chain and one light chain; whereas in other instances the variant forms contain two identical light chains and two identical heavy chains (or subparts thereof). For example, by comparing similar sequences, one can identify those sections (e.g., particular amino acids) that can be modified and how they can be modified while still retaining (or improving) the functionality of the ABP.

In some aspects, an ABP can comprise a polypeptide comprising an amino acid sequence at least 80%, 81%, 82%, 83%, 84%, 85%, 86%, 87%, 88%, 89%, 90%, 91%, 92%, 93%, 94%, 95%, 96%, 97%, 98%, 99%, or 100% identical to an amino acid sequence set forth in Table 1. In an aspect, an ABP can comprise a polypeptide comprising an amino acid sequence having at least 10, 15, 20, 25, 30, 35, 40, 45, 50, 55, 60, 65, 70, 75, 80, 85, 90, 95, 100, 200, 300, 400, or 500 (or any integer within these numbers) contiguous amino acids of the amino acid sequences set forth in Table 1.

In some aspects, an ABP can comprise a polypeptide encoded by a nucleotide sequence at least 80%, 81%, 82%, 83%, 84%, 85%, 86%, 87%, 88%, 89%, 90%, 91%, 92%, 93%, 94%, 95%, 96%, 97%, 98%, 99%, or 100% identical to a nucleotide sequence set forth in Table 1. In an aspect, an ABP can comprise a polypeptide encoded by a nucleotide sequence having at least 10, 15, 20, 25, 30, 35, 40, 45, 50, 55, 60, 65, 70, 75, 80, 85, 90, 95, 100, 200, 300, 400, or 500 (or any integer within these numbers) contiguous nucleotides of the nucleotide sequences set forth in Table 1.

In light of the present disclosure, a skilled artisan will be able to determine suitable variants of the ABPs as set forth herein using well-known techniques. In certain embodiments, one skilled in the art can identify suitable areas of the molecule that may be changed without destroying activity by targeting regions not believed to be important for activity. In certain embodiments, one can identify residues and portions of the molecules that are conserved among similar polypeptides. In certain embodiments, even areas that can be important for biological activity or for structure can be subject to conservative amino acid substitutions without destroying the biological activity or without adversely affecting the polypeptide structure.

Additionally, one skilled in the art can review structure-function studies identifying residues in similar polypeptides that are important for activity or structure. In view of such a comparison, one can predict the importance of amino acid residues in a protein that correspond to amino acid residues which are important for activity or structure in similar proteins. One skilled in the art can opt for chemically similar amino acid substitutions for such predicted important amino acid residues.

One skilled in the art can also analyze the three-dimensional structure and amino acid sequence in relation to that structure in similar ABPs. In view of such information, one skilled in the art can predict the alignment of amino acid residues of an antibody with respect to its three dimensional structure. In certain embodiments, one skilled in the art can choose not to make radical changes to amino acid residues predicted to be on the surface of the protein, since such residues can be involved in important interactions with other molecules. Moreover, one skilled in the art can generate test variants containing a single amino acid substitution at each desired amino acid residue. The variants can then be screened using activity assays known to those skilled in the art. Such variants can be used to gather information about suitable variants. For example, if one discovered that a change to a particular amino acid residue resulted in destroyed, undesirably reduced, or unsuitable activity, variants with such a change can be avoided. In other words, based on information gathered from such routine experiments, one skilled in the art can readily determine the amino acids where further substitutions should be avoided either alone or in combination with other mutations.

A number of scientific publications have been devoted to the prediction of secondary structure. See Moult J., Curr. Op. in Biotech., 7(4):422-427 (1996), Chou et al., Biochemistry, 13(2):222-245 (1974); Chou et al., Biochemistry, 113(2): 211-222 (1974); Chou et al., Adv. Enzymol. Relat. Areas Mol. Biol., 47:45-148 (1978); Chou et al., Ann. Rev. Biochem., 47:251-276 and Chou et al., Biophys. J., 26:367-384 (1979). Moreover, computer programs are currently available to assist with predicting secondary structure. One method of predicting secondary structure is based upon homology modeling. For example, two polypeptides or proteins which have a sequence identity of greater than 30%, or similarity greater than 40% often have similar structural topologies. The recent growth of the protein structural database (PDB) has provided enhanced predictability of secondary structure, including the potential number of folds within a polypeptide's or protein's structure. See Holm et al., Nucl. Acid. Res., 27(1):244-247 (1999). It has been suggested (Brenner et al., Curr. Op. Struct. Biol., 7(3):369-376 (1997)) that there are a limited number of folds in a given polypeptide or protein and that once a critical number of structures have been resolved, structural prediction will become dramatically more accurate.

Additional methods of predicting secondary structure include "threading" (Jones, D., Curr. Opin. Struct. Biol., 7(3): 377-87 (1997); Sippl et al., Structure, 4(1):15-19 (1996)), "profile analysis" (Bowie et al., Science, 253:164-170 (1991); Gribskov et al., Meth. Enzym., 183:146-159 (1990); Gribskov et al., Proc. Nat. Acad. Sci. USA, 84(13):4355-4358 (1987)), and "evolutionary linkage" (See Holm, supra (1999), and Brenner, supra (1997)).

In certain embodiments, antigen binding protein variants include glycosylation variants wherein the number and/or type of glycosylation site has been altered compared to the amino acid sequences of a parent polypeptide. In certain embodiments, protein variants comprise a greater or a lesser number of N-linked glycosylation sites than the native protein. An N-linked glycosylation site is characterized by the sequence: Asn-X-Ser or Asn-X-Thr, wherein the amino acid residue designated as X can be any amino acid residue except proline. The substitution of amino acid residues to create this sequence provides a potential new site for the addition of an N-linked carbohydrate chain. Alternatively, substitutions which eliminate this sequence will remove an existing N-linked carbohydrate chain. Also provided is a rearrangement of N-linked carbohydrate chains wherein one or more N-linked glycosylation sites (typically those that are naturally occurring) are eliminated and one or more new N-linked sites are created. Additional preferred antibody variants include cysteine variants wherein one or more cysteine residues are deleted from or substituted for another amino acid (e.g., serine) as compared to the parent amino acid sequence. Cysteine variants can be useful when antibodies must be refolded into a biologically active conformation such as after the isolation of insoluble inclusion bodies. Cysteine variants generally have fewer cysteine residues than the native protein, and typically have an even number to minimize interactions resulting from unpaired cysteines.

According to certain embodiments, amino acid substitutions are those which: (1) reduce susceptibility to proteolysis, (2) reduce susceptibility to oxidation, (3) alter binding affinity for forming protein complexes, (4) alter binding affinities, and/or (4) confer or modify other physiocochemical or functional properties on such polypeptides. According to certain embodiments, single or multiple amino acid substitutions (in certain embodiments, conservative amino acid substitutions) can be made in the naturally-occurring sequence (in certain embodiments, in the portion of the polypeptide outside the domain(s) forming intermolecular contacts). In certain embodiments, a conservative amino acid substitution typically may not substantially change the structural characteristics of the parent sequence (e.g., a replacement amino acid should not tend to break a helix that occurs in the parent sequence, or disrupt other types of secondary structure that characterizes the parent sequence). Examples of art-recognized polypeptide secondary and tertiary structures are described in Proteins, Structures and Molecular Principles (Creighton, Ed., W. H. Freeman and Company, New York (1984)); Introduction to Protein Structure (C. Branden & J. Tooze, eds., Garland Publishing, New York, N.Y. (1991)); and Thornton et al., Nature, 354:105 (1991), which are each incorporated herein by reference.

In some embodiments, the variants are variants of the nucleic acid sequences of the ABPs disclosed herein. One of skill in the art will appreciate that the above discussion can be used for identifying, evaluating, and/creating ABP protein variants and also for nucleic acid sequences that can encode for those protein variants. Thus, nucleic acid sequences encoding for those protein variants are contemplated. For example, an ABP variant can have at least 80, 80-85, 85-90, 90-95, 95-97, 97-99 or greater identity to at least one nucleic acid sequence described herein or at least one to six (and various combinations thereof) of the CDR(s) encoded by the nucleic acid sequences described herein.

In some embodiments, the antibody (or nucleic acid sequence encoding it) is a variant if the nucleic acid sequence that encodes the particular ABP (or the nucleic acid sequence itself) can selectively hybridize to any of the nucleic acid sequences that encode the proteins described herein under stringent conditions. In one embodiment, suitable moderately stringent conditions include prewashing in a solution of 5×SSC; 0.5% SDS, 1.0 mM EDTA (pH 8:0); hybridizing at 50 C, -65 C, 5×SSC, overnight or, in the event of cross-species homology, at 45 C with 0.5×SSC; followed by washing twice at 65 C for 20 minutes with each of 2×, 0.5×, and 0.2×SSC containing 0.1% SDS. Such hybridizing DNA sequences are also within the scope of this invention, as are nucleotide sequences that, due to code degeneracy, encode an antibody polypeptide that is encoded by a hybridizing DNA sequence and the amino acid sequences that are encoded by these nucleic acid sequences. In some embodiments, variants of CDRs include nucleic acid sequences and the amino acid sequences encoded by those sequences, that hybridize to one or more of the CDRs within the sequences noted above. The phrase "selectively hybridize" referred to in this context means to detectably and selectively bind. Polynucleotides, oligonucleotides and fragments thereof in accordance with the invention selectively hybridize to nucleic acid strands under hybridization and wash conditions that minimize appreciable amounts of detectable binding to nonspecific nucleic acids. High acids. High stringency conditions can be used to achieve selective hybridization conditions as known in the art and discussed herein. Generally, the nucleic acid sequence homology between the polynucleotides, oligonucleotides, and fragments of the invention and a nucleic acid sequence of interest will be at least 80%, and more typically with preferably increasing homologies of at least 85%, 90%, 95%, 99%, and 100%. Two amino acid sequences are homologous if there is a partial or complete identity between their sequences. For example, 85% homology means that 85% of the amino acids are identical when the two sequences are aligned for maximum matching. Gaps (in either of the two sequences being matched) are allowed in maximizing matching; gap lengths of 5 or less are preferred with 2 or less being more preferred. Alternatively and preferably, two protein sequences (or polypeptide sequences derived from them of at least 30 amino acids in length) are homologous, as this term is used herein, if they have an alignment score of at more than 5 (in standard deviation units) using the program ALIGN with the mutation data matrix and a gap penalty of 6 or greater. See Dayhoff, M. O., in Atlas of Protein Sequence and Structure, pp. 101-110 (Volume 5, National Biomedical Research Foundation (1972)) and Supplement 2 to this volume, pp. 1-10. The two sequences or parts thereof are more preferably homologous if their amino acids are greater than or equal to 50% identical when optimally aligned using the ALIGN program. The term "corresponds to" is used herein to mean that a polynucleotide sequence is homologous (i.e., is identical, not strictly evolutionarily related) to all or a portion of a reference polynucleotide sequence, or that a polypeptide sequence is identical to a reference polypeptide sequence. In contradistinction, the term "complementary to" is used herein to mean that the complementary sequence is homologous to all or a portion of a reference polynucleotide sequence. For illustration, the nucleotide sequence "TATAC" corresponds to a reference sequence "TATAC" and is complementary to a reference sequence "GTATA".

Preparation of Antigen Binding Proteins (e.g., Antibodies)

In certain embodiments, antigen binding proteins (such as antibodies) are produced by immunization with an antigen (e.g., ManLAM). In certain embodiments, antibodies can be produced by immunization with ManLAM or a fragment thereof. In certain embodiments, the antibodies of the invention can be polyclonal or monoclonal, and/or can be recombinant antibodies. In certain embodiments, antibodies of the invention are human antibodies prepared, for example, by immunization of transgenic animals capable of producing human antibodies (see, for example, PCT Published Application No. WO 93/12227).

In certain embodiments, certain strategies can be employed to manipulate inherent properties of an antibody, such as the affinity of an antibody for its target. Such strategies include, but are not limited to, the use of site-specific or random mutagenesis of the polynucleotide molecule encoding an antibody to generate an antibody variant. In certain embodiments, such generation is followed by screening for antibody variants that exhibit the desired change, e.g. increased or decreased affinity.

In certain embodiments, the amino acid residues targeted in mutagenic strategies are those in the CDRs. In certain embodiments, amino acids in the framework regions of the variable domains are targeted. In certain embodiments, such framework regions have been shown to contribute to the target binding properties of certain antibodies. See, e.g., Hudson, Curr. Opin. Biotech., 9:395-402 (1999) and references therein.

In certain embodiments, smaller and more effectively screened libraries of antibody variants are produced by restricting random or site-directed mutagenesis to hyper-mutation sites in the CDRs, which are sites that correspond to areas prone to mutation during the somatic affinity maturation process. See, e.g., Chowdhury & Pastan, Nature Biotech., 17: 568-572 (1999) and references therein. In certain embodiments, certain types of DNA elements can be used to identify hyper-mutation sites including, but not limited to, certain direct and inverted repeats, certain consensus sequences, certain secondary structures, and certain palindromes. For example, such DNA elements that can be used to identify hyper-mutation sites include, but are not limited to, a tetra-base sequence comprising a purine (A or G), followed by guainine (G), followed by a pyrimidine (C or T), followed by either adenosine or thymidine (A or T) (i.e., A/G-G-C/T-A/T). Another example of a DNA element that can be used to identify hyper-mutation sites is the serine codon, A-G-C/T.

Preparation of Fully Human ABPs (e.g., Antibodies)

In certain embodiments, a phage display technique is used to generate monoclonal antibodies. In certain embodiments, such techniques produce fully human monoclonal antibodies. In certain embodiments, a polynucleotide encoding a single Fab or Fv antibody fragment is expressed on the surface of a phage particle. See, e.g., Hoogenboom et al., J. Mol. Biol., 227: 381 (1991); Marks et al., J Mol Biol 222: 581 (1991); U.S. Pat. No. 5,885,793. In certain embodiments, phage are "screened" to identify those antibody fragments having affinity for target. Thus, certain such processes mimic immune selection through the display of antibody fragment repertoires on the surface of filamentous bacteriophage, and subsequent selection of phage by their binding to target. In certain such procedures, high affinity functional neutralizing antibody fragments are isolated. In certain such embodiments (discussed in more detail below), a complete repertoire of human antibody genes is created by cloning naturally rearranged human V genes from peripheral blood lymphocytes. See, e.g., Mullinax et al., Proc Natl Acad Sci (USA), 87: 8095-8099 (1990).

In some embodiments, ABPs are prepared using the phage display methods described in the examples section below.

According to certain embodiments, antibodies of the invention are prepared through the utilization of a transgenic mouse that has a substantial portion of the human antibody producing genome inserted but that is rendered deficient in the production of endogenous, murine antibodies. Such mice, then, are capable of producing human immunoglobulin molecules and antibodies and are deficient in the production of murine immunoglobulin molecules and antibodies. Technologies utilized for achieving this result are disclosed in the patents, applications and references disclosed in the specification, herein. In certain embodiments, one can employ methods such as those disclosed in PCT Published Application No. WO 98/24893 or in Mendez et al., Nature Genetics, 15:146-156 (1997), which are hereby incorporated by reference for any purpose.

Generally, fully human monoclonal ABPs (e.g., antibodies) specific for MANLAM can be produced as follows. Transgenic mice containing human immunoglobulin genes are immunized with the antigen of interest, e.g. ManLAM, lymphatic cells (such as B-cells) from the mice that express antibodies are obtained. Such recovered cells are fused with a myeloid-type cell line to prepare immortal hybridoma cell lines, and such hybridoma cell lines are screened and selected to identify hybridoma cell lines that produce antibodies specific to the antigen of interest. In certain embodiments, the production of a hybridoma cell line that produces antibodies specific to ManLAM is provided.

In certain embodiments, fully human antibodies are produced by exposing human splenocytes (B or T cells) to an antigen in vitro, and then reconstituting the exposed cells in an immunocompromised mouse, e.g. SCID or nod/SCID. See, e.g., Brams et al., J. Immunol. 160: 2051-2058 (1998); Carballido et al., Nat. Med., 6: 103-106 (2000). In certain such approaches, engraftment of human fetal tissue into SCID mice (SCID-hu) results in long-term hematopoiesis and human T-cell development. See, e.g., McCune et al., Science, 241:1532-1639 (1988); Ifversen et al., Sem. Immunol., 8:243-248 (1996). In certain instances, humoral immune response in such chimeric mice is dependent on co-development of human T-cells in the animals. See, e.g., Martensson et al., Immunol., 83:1271-179 (1994). In certain approaches, human peripheral blood lymphocytes are transplanted into SCID mice. See, e.g., Mosier et al., Nature, 335:256-259 (1988). In certain such embodiments, when such transplanted cells are treated either with a priming agent, such as Staphylococcal Enterotoxin A (SEA), or with anti-human CD40 monoclonal antibodies, higher levels of B cell production is detected. See, e.g., Martensson et al., Immunol., 84: 224-230 (1995); Murphy et al., Blood, 86:1946-1953 (1995).

Thus, in certain embodiments, fully human antibodies can be produced by the expression of recombinant DNA in host cells or by expression in hybridoma cells. In other embodiments, antibodies can be produced using the phage display techniques described herein.

The antibodies described herein were prepared through the utilization of the XenoMouse technology, as described herein. Such mice, then, are capable of producing human immunoglobulin molecules and antibodies and are deficient in the production of murine immunoglobulin molecules and antibodies. Technologies utilized for achieving the same are disclosed in the patents, applications, and references disclosed in the background section herein. In particular, however, a preferred embodiment of transgenic production of mice and antibodies therefrom is disclosed in U.S. patent application Ser. No. 08/759,620, filed Dec. 3, 1996 and International Patent Application Nos. WO 98/24893, published Jun. 11, 1998 and WO 00/76310, published Dec. 21, 2000, the disclosures of which are hereby incorporated by reference. See also Mendez et al., Nature Genetics, 15:146-156 (1997), the disclosure of which is hereby incorporated by reference.

Through the use of such technology, fully human monoclonal antibodies to a variety of antigens have been produced. Essentially, XenoMouse lines of mice are immunized with an antigen of interest (e.g. ManLAM), lymphatic cells (such as B-cells) are recovered from the hyper-immunized mice, and the recovered lymphocytes are fused with a myeloid-type cell line to prepare immortal hybridoma cell lines. These hybridoma cell lines are screened and selected to identify hybridoma cell lines that produced antibodies specific to the antigen of interest. Provided herein are methods for the production of multiple hybridoma cell lines that produce antibodies specific to ManLAM. Further, provided herein are characterization of the antibodies produced by such cell lines, including nucleotide and amino acid sequence analyses of the heavy and light chains of such antibodies.

The production of the XenoMouse strains of mice is further discussed and delineated in U.S. patent application Ser. No. 07/466,008, filed Jan. 12, 1990, Ser. No. 07/610,515, filed Nov. 8, 1990, Ser. No. 07/919,297, filed Jul. 24, 1992, Ser. No. 07/922,649, filed Jul. 30, 1992, Ser. No. 08/031,801, filed Mar. 15, 1993, Ser. No. 08/112,848, filed Aug. 27, 1993, Ser. No. 08/234,145, filed Apr. 28, 1994, Ser. No. 08/376,279, filed Jan. 20, 1995, Ser. No. 08/430,938, filed Apr. 27, 1995, Ser. No. 08/464,584, filed Jun. 5, 1995, Ser. No. 08/464,582, filed Jun. 5, 1995, Ser. No. 08/463,191, filed Jun. 5, 1995, Ser. No. 08/462,837, filed Jun. 5, 1995, Ser. No. 08/486,853, filed Jun. 5, 1995, Ser. No. 08/486,857, filed Jun. 5, 1995, Ser. No. 08/486,859, filed Jun. 5, 1995, Ser. No. 08/462,513, filed Jun. 5, 1995, Ser. No. 08/724,752, filed Oct. 2, 1996, Ser. No. 08/759,620, filed Dec. 3, 1996, U.S. Publication 2003/0093820, filed Nov. 30, 2001 and U.S. Pat. Nos. 6,162,963, 6,150,584, 6,114,598, 6,075,181, and 5,939,598 and Japanese Patent Nos. 3 068 180 B2, 3 068 506 B2, and 3 068 507 B2. See also European Patent No., EP 0 463 151 B1, grant published Jun. 12, 1996, International Patent Application No., WO 94/02602, published Feb. 3, 1994, International Patent Application No., WO 96/34096, published Oct. 31, 1996, WO 98/24893, published Jun. 11, 1998, WO 00/76310, published Dec. 21, 2000. The disclosures of each of the above-cited patents, applications, and references are hereby incorporated by reference in their entirety.

In an alternative approach, others, including GenPharm International, Inc., have utilized a "minilocus" approach. In the minilocus approach, an exogenous Ig locus is mimicked through the inclusion of pieces (individual genes) from the Ig locus. Thus, one or more VH genes, one or more DH genes, one or more JH genes, a mu constant region, and usually a second constant region (preferably a gamma constant region) are formed into a construct for insertion into an animal. This approach is described in U.S. Pat. No. 5,545,807 to Surani et al. and U.S. Pat. Nos. 5,545,806, 5,625,825, 5,625,126, 5,633,425, 5,661,016, 5,770,429, 5,789,650, 5,814,318, 5,877,397, 5,874,299, and 6,255,458 each to Lonberg & Kay, U.S. Pat. Nos. 5,591,669 and 6,023,010 to Krimpenfort & Berns, U.S. Pat. Nos. 5,612,205, 5,721,367, and 5,789,215 to Berns et al., and U.S. Pat. No. 5,643,763 to Choi & Dunn, and GenPharm International U.S. patent application Ser. No. 07/574,748, filed Aug. 29, 1990, Ser. No. 07/575,962, filed Aug. 31, 1990, Ser. No. 07/810,279, filed Dec. 17, 1991, Ser. No. 07/853,408, filed Mar. 18, 1992, Ser. No. 07/904,068, filed Jun. 23, 1992, Ser. No. 07/990,860, filed Dec. 16, 1992, Ser. No. 08/053,131, filed Apr. 26, 1993, Ser. No. 08/096,762, filed Jul. 22, 1993, Ser. No. 08/155,301, filed Nov. 18, 1993, Ser. No. 08/161,739, filed Dec. 3, 1993, Ser. No. 08/165,699, filed Dec. 10, 1993, Ser. No. 08/209,741, filed Mar. 9, 1994, the disclosures of which are hereby incorporated by reference. See also European Patent No. 0 546 073 B1, International Patent Application Nos. WO 92/03918, WO 92/22645, WO 92/22647, WO 92/22670, WO 93/12227, WO 94/00569, WO 94/25585, WO 96/14436, WO 97/13852, and WO 98/24884 and U.S. Pat. No. 5,981,175, the disclosures of which are hereby incorporated by reference in their entirety. See further Taylor et al., 1992, Chen et al., 1993, Tuaillon et al., 1993, Choi et al., 1993, Lonberg et al., (1994), Taylor et al., (1994), and Tuaillon et al., (1995), Fishwild et al., (1996), the disclosures of which are hereby incorporated by reference in their entirety.

Kirin has also demonstrated the generation of human antibodies from mice in which, through microcell fusion, large pieces of chromosomes, or entire chromosomes, have been introduced. See European Patent Application Nos. 773 288 and 843 961, the disclosures of which are hereby incorporated by reference. Additionally, KM mice, which are the result of cross-breeding of Kirin's Tc mice with Medarex's minilocus (Humab) mice have been generated. These mice possess the human IgH transchromosome of the Kirin mice and the kappa chain transgene of the Genpharm mice (Ishida et al., Cloning Stem Cells, (2002) 4:91-102).

Human antibodies can also be derived by in vitro methods. Suitable examples include but are not limited to phage display (CAT, Morphosys, Dyax, Biosite/Medarex, Xoma, Symphogen, Alexion (formerly Proliferon), Affimed) ribosome display (CAT), yeast display, and the like.

In some embodiments, the antibodies described herein possess human IgG4 heavy chains as well as IgG2 heavy chains. Antibodies can also be of other human isotypes, including IgG1. The antibodies possessed high affinities, typically possessing a Kd of from about $10^{-6}$ through about $10^{-13}$ M or below, when measured by various techniques.

As will be appreciated, antibodies can be expressed in cell lines other than hybridoma cell lines. Sequences encoding particular antibodies can be used to transform a suitable mammalian host cell. Transformation can be by any known method for introducing polynucleotides into a host cell, including, for example packaging the polynucleotide in a virus (or into a viral vector) and transducing a host cell with the virus (or vector) or by transfection procedures known in the art, as exemplified by U.S. Pat. Nos. 4,399,216, 4,912,040, 4,740,461, and 4,959,455 (which patents are hereby incorporated herein by reference). The transformation procedure used depends upon the host to be transformed. Methods for introducing heterologous polynucleotides into mammalian cells are well known in the art and include dextran-mediated transfection, calcium phosphate precipitation, polybrene mediated transfection, protoplast fusion, electroporation, encapsulation of the polynucleotide(s) in liposomes, and direct microinjection of the DNA into nuclei.

Mammalian cell lines available as hosts for expression are well known in the art and include many immortalized cell lines available from the American Type Culture Collection (ATCC), including but not limited to Chinese hamster ovary (CHO) cells, HeLa cells, baby hamster kidney (BHK) cells, monkey kidney cells (COS), human hepatocellular carcinoma cells (e.g., Hep G2), human epithelial kidney 293 cells, and a number of other cell lines. Cell lines of particular preference are selected through determining which cell lines have high expression levels and produce antibodies with constitutive ManLAM binding properties.

In certain embodiments, antigen binding proteins bind to ManLAM with a dissociation constant (KD) of less than approximately 1 nM, e.g., 1000 pM to 100 pM, 100 pM to 10 pM, 10 pM to 1 pM, and/or 1 pM to 0.1 pM or less.

In certain embodiments, antigen binding proteins comprise an immunoglobulin molecule of at least one of the IgG1, IgG2, IgG3, IgG4, IgE, IgA, IgD, and IgM isotype. In certain embodiments, antigen binding proteins comprise a human kappa light chain and/or a human heavy chain. In certain embodiments, the heavy chain is of the IgG1, IgG2, IgG3, IgG4, IgE, IgA, IgD, or IgM isotype. In certain embodiments, antigen binding proteins have been cloned for expression in mammalian cells. In certain embodiments, antigen binding proteins comprise a constant region other than any of the constant regions of the IgG1, IgG2, IgG3, IgG4, IgE, IgA, IgD, and IgM isotype.

In certain embodiments, antigen binding proteins comprise a human lambda light chain and a human IgG2 heavy chain.

In certain embodiments, antigen binding proteins comprise a human lambda light chain and a human IgG4 heavy chain. In certain embodiments, antigen binding proteins comprise a human lambda light chain and a human IgG1, IgG3, IgE, IgA, IgD or IgM heavy chain. In other embodiments, antigen binding proteins comprise a human kappa light chain and a human IgG2 heavy chain. In certain embodiments, antigen binding proteins comprise a human kappa light chain and a human IgG4 heavy chain. In certain embodiments, antigen binding proteins comprise a human kappa light chain and a human IgG1, IgG3, IgE, IgA, IgD or IgM heavy chain. In certain embodiments, antigen binding proteins comprise variable regions of antibodies ligated to a constant region that is neither the constant region for the IgG2 isotype, nor the constant region for the IgG4 isotype. In certain embodiments, antigen binding proteins have been cloned for expression in mammalian cells.

In certain embodiments, conservative modifications to the heavy and light chains of antibodies will produce antibodies to ManLAM having functional and chemical characteristics similar to those of the antibodies from the cell lines described herein. In contrast, in certain embodiments, substantial modifications in the functional and/or chemical characteristics of antibodies to ManLAM can be accomplished by selecting substitutions in the amino acid sequence of the heavy and light chains that differ significantly in their effect on maintaining (a) the structure of the molecular backbone in the area of the substitution, for example, as a sheet or helical conformation, (b) the charge or hydrophobicity of the molecule at the target site, or (c) the bulk of the side chain.

For example, a "conservative amino acid substitution" can involve a substitution of a native amino acid residue with a normative residue such that there is little or no effect on the polarity or charge of the amino acid residue at that position. Furthermore, any native residue in the polypeptide can also be substituted with alanine, as has been previously described for “alanine scanning mutagenesis.” Desired amino acid substitutions (whether conservative or non-conservative) can be determined by those skilled in the art at the time such substitutions are desired. In certain embodiments, amino acid substitutions can be used to identify important residues of antibodies to ManLAM, or to increase or decrease the affinity of the antibodies to ManLAM as described herein.

In certain embodiments, antibodies of the present invention can be expressed in cell lines other than hybridoma cell lines. In certain embodiments, sequences encoding particular antibodies can be used for transformation of a suitable mammalian host cell. According to certain embodiments, transformation can be by any known method for introducing polynucleotides into a host cell, including, for example packaging the polynucleotide in a virus (or into a viral vector) and transducing a host cell with the virus (or vector) or by transfection procedures known in the art, as exemplified by U.S. Pat. Nos. 4,399,216, 4,912,040, 4,740,461, and 4,959,455 (which patents are hereby incorporated herein by reference for any purpose). In certain embodiments, the transformation procedure used can depend upon the host to be transformed. Methods for introduction of heterologous polynucleotides into mammalian cells are well known in the art and include, but are not limited to, dextran-mediated transfection, calcium phosphate precipitation, polybrene mediated transfection, protoplast fusion, electroporation, encapsulation of the polynucleotide(s) in liposomes, and direct microinjection of the DNA into nuclei.

Mammalian cell lines available as hosts for expression are well known in the art and include, but are not limited to, many immortalized cell lines available from the American Type Culture Collection (ATCC), including but not limited to Chinese hamster ovary (CHO) cells, HeLa cells, baby hamster kidney (BHK) cells, monkey kidney cells (COS), human hepatocellular carcinoma cells (e.g., Hep G2), and a number of other cell lines. In certain embodiments, cell lines can be selected through determining which cell lines have high expression levels and produce antibodies with constitutive HGF binding properties. Appropriate expression vectors for mammalian host cells are well known.

In certain embodiments, antigen binding proteins comprise one or more polypeptides. In certain embodiments, any of a variety of expression vector/host systems can be utilized to express polynucleotide molecules encoding polypeptides comprising one or more ABP components or the ABP itself. Such systems include, but are not limited to, microorganisms, such as bacteria transformed with recombinant bacteriophage, plasmid, or cosmid DNA expression vectors; yeast transformed with yeast expression vectors; insect cell systems infected with virus expression vectors (e.g., baculovirus); plant cell systems transfected with virus expression vectors (e.g., cauliflower mosaic virus, CaMV, tobacco mosaic virus, TMV) or transformed with bacterial expression vectors (e.g., Ti or pBR322 plasmid); or animal cell systems.

In certain embodiments, a polypeptide comprising one or more ABP components or the ABP itself is recombinantly expressed in yeast. Certain such embodiments use commercially available expression systems, e.g., the Pichia Expression System (Invitrogen, San Diego, Calif.), following the manufacturer's instructions. In certain embodiments, such a system relies on the pre-pro-alpha sequence to direct secretion. In certain embodiments, transcription of the insert is driven by the alcohol oxidase (AOX1) promoter upon induction by methanol.

In certain embodiments, a secreted polypeptide comprising one or more ABP components or the ABP itself is purified from yeast growth medium. In certain embodiments, the methods used to purify a polypeptide from yeast growth medium is the same as those used to purify the polypeptide from bacterial and mammalian cell supernatants.

In certain embodiments, a nucleic acid encoding a polypeptide comprising one or more ABP components or the ABP itself is cloned into a baculovirus expression vector, such as pVL1393 (PharMingen, San Diego, Calif.). In certain embodiments, such a vector can be used according to the manufacturer's directions (PharMingen) to infect *Spodoptera frugiperda* cells in sF9 protein-free media and to produce recombinant polypeptide. In certain embodiments, a polypeptide is purified and concentrated from such media using a heparin-Sepharose column (Pharmacia).

In certain embodiments, a polypeptide comprising one or more ABP components or the ABP itself is expressed in an insect system. Certain insect systems for polypeptide expression are well known to those of skill in the art. In one such system, *Autographa californica* nuclear polyhedrosis virus (AcNPV) is used as a vector to express foreign genes in *Spodoptera frugiperda* cells or in *Trichoplusia larvae*. In certain embodiments, a nucleic acid molecule encoding a polypeptide can be inserted into a nonessential gene of the virus, for example, within the polyhedrin gene, and placed under control of the promoter for that gene. In certain embodiments, successful insertion of a nucleic acid molecule will render the nonessential gene inactive. In certain embodiments, that inactivation results in a detectable characteristic. For example, inactivation of the polyhedrin gene results in the production of virus lacking coat protein.

In certain embodiments, recombinant viruses can be used to infect *S. frugiperda* cells or *Trichoplusia larvae*. See, e.g., Smith et al., J. Virol., 46: 584 (1983); Engelhard et al., Proc. Nat. Acad. Sci. (USA), 91: 3224-7 (1994).

In certain embodiments, polypeptides comprising one or more ABP components or the ABP itself made in bacterial cells are produced as insoluble inclusion bodies in the bacteria. In certain embodiments, host cells comprising such inclusion bodies are collected by centrifugation; washed in 0.15 M NaCl, 10 mM Tris, pH 8, 1 mM EDTA; and treated with 0.1 mg/ml lysozyme (Sigma, St. Louis, Mo.) for 15 minutes at room temperature. In certain embodiments, the lysate is cleared by sonication, and cell debris is pelleted by centrifugation for 10 minutes at 12,000×g. In certain embodiments, the polypeptide-containing pellet is resuspended in 50 mM Tris, pH 8, and 10 mM EDTA; layered over 50% glycerol; and centrifuged for 30 minutes at 6000×g. In certain embodiments, that pellet can be resuspended in standard phosphate buffered saline solution (PBS) free of Mg++ and Ca++. In certain embodiments, the polypeptide is further purified by fractionating the resuspended pellet in a denaturing SDS polyacrylamide gel (See, e.g., Sambrook et al., supra). In certain embodiments, such a gel can be soaked in 0.4 M KCl to visualize the protein, which can be excised and electroeluted in gel-running buffer lacking SDS. According to certain embodiments, a Glutathione-S-Transferase (GST) fusion protein is produced in bacteria as a soluble protein. In certain embodiments, such GST fusion protein is purified using a GST Purification Module (Pharmacia).

In certain embodiments, it is desirable to "refold" certain polypeptides, e.g., polypeptides comprising one or more ABP components or the ABP itself. In certain embodiments, such polypeptides are produced using certain recombinant systems discussed herein. In certain embodiments, polypeptides are "refolded" and/or oxidized to form desired tertiary structure and/or to generate disulfide linkages. In certain embodiments, such structure and/or linkages are related to certain biological activity of a polypeptide. In certain embodiments, refolding is accomplished using any of a number of procedures known in the art. Exemplary methods include, but are not limited to, exposing the solubilized polypeptide agent to a pH typically above 7 in the presence of a chaotropic agent. An exemplary chaotropic agent is guanidine. In certain embodiments, the refolding/oxidation solution also contains a reducing agent and the oxidized form of that reducing agent. In certain embodiments, the reducing agent and its oxidized form are present in a ratio that will generate a particular redox potential that allows disulfide shuffling to occur. In certain embodiments, such shuffling allows the formation of cysteine bridges. Exemplary redox couples include, but are not limited to, cysteine/cystamine, glutathione/dithiobisGSH, cupric chloride, dithiothreitol DTT/dithiane DTT, and 2-mercaptoethanol (bME)/dithio-bME. In certain embodiments, a cosolvent is used to increase the efficiency of refolding. Exemplary cosolvents include, but are not limited to, glycerol, polyethylene glycol of various molecular weights, and arginine.

In certain embodiments, one substantially purifies a polypeptide comprising one or more ABP components or the ABP itself. Certain protein purification techniques are known to those of skill in the art. In certain embodiments, protein purification involves crude fractionation of polypeptide fractionations from non-polypeptide fractions. In certain embodiments, polypeptides are purified using chromatographic and/or electrophoretic techniques. Exemplary purification methods include, but are not limited to, precipitation with ammonium sulphate; precipitation with PEG; immunoprecipitation; heat denaturation followed by centrifugation; chromatography, including, but not limited to, affinity chromatography (e.g., Protein-A-Sepharose), ion exchange chromatography, exclusion chromatography, and reverse phase chromatography; gel filtration; hydroxyapatite chromatography; isoelectric focusing; polyacrylamide gel electrophoresis; and combinations of such and other techniques. In certain embodiments, a polypeptide is purified by fast protein liquid chromatography or by high pressure liquid chromatography (HPLC). In certain embodiments, purification steps can be changed or certain steps can be omitted and still result in a suitable method for the preparation of a substantially purified polypeptide.

In certain embodiments, one quantitates the degree of purification of a polypeptide preparation. Certain methods for quantifying the degree of purification are known to those of skill in the art. Certain exemplary methods include, but are not limited to, determining the specific binding activity of the preparation and assessing the amount of a polypeptide within a preparation by SDS/PAGE analysis. Certain exemplary methods for assessing the amount of purification of a polypeptide preparation comprise calculating the binding activity of a preparation and comparing it to the binding activity of an initial extract. In certain embodiments, the results of such a calculation are expressed as "fold purification." The units used to represent the amount of binding activity depend upon the particular assay performed.

In certain embodiments, a polypeptide comprising one or more ABP components or the ABP itself is partially purified. In certain embodiments, partial purification can be accomplished by using fewer purification steps or by utilizing different forms of the same general purification scheme. For example, in certain embodiments, cation-exchange column chromatography performed utilizing an HPLC apparatus will generally result in a greater "fold purification" than the same technique utilizing a low-pressure chromatography system. In certain embodiments, methods resulting in a lower degree of purification can have advantages in total recovery of polypeptide, or in maintaining binding activity of a polypeptide.

In certain instances, the electrophoretic migration of a polypeptide can vary, sometimes significantly, with different conditions of SDS/PAGE. See, e.g., Capaldi et al, Biochem. Biophys. Res. Comm., 76: 425 (1977). It will be appreciated that under different electrophoresis conditions, the apparent molecular weights of purified or partially purified polypeptide can be different.

Competing Antigen Binding Proteins

In another aspect, antigen binding proteins are provided that compete with one of the exemplified antibodies or functional fragments binding to the epitope described herein for specific binding to ManLAM. Such antigen binding proteins can also bind to the same epitope as one of the herein exemplified antigen binding proteins, or an overlapping epitope. Antigen binding proteins and fragments that compete with or bind to the same epitope as the exemplified antigen binding proteins are expected to show similar functional properties.

Certain Therapeutic Uses and Pharmaceutical Compositions

In certain embodiments, an antigen binding protein to ManLAM is administered alone. In certain embodiments, an antigen binding protein to ManLAM is administered prior to the administration of at least one other therapeutic agent. In certain embodiments, an antigen binding protein to ManLAM is administered concurrent with the administration of at least one other therapeutic agent. In certain embodiments, an antigen binding protein to ManLAM is administered subsequent to the administration of at least one other therapeutic agent. In other embodiments, an antigen binding protein to ManLAM is administered prior to the administration of at least one other therapeutic agent. As will be appreciated by one of skill in the art, in some embodiments, the ABP is combined with the other agent/compound. In some embodiments, the ABP and other agent are administered concurrently. In some embodiments, the ABP and other agent are not administered simultaneously, with the ABP being administered before or after the agent is administered. In some embodiments, the subject receives both the ABP and the other agent during a same period of prevention, occurrence of a disorder, and/or period of treatment.

Pharmaceutical compositions of the invention can be administered in combination therapy, i.e., combined with other agents. In certain embodiments, the combination therapy comprises an antigen binding protein capable of binding ManLAM, in combination with at least one other agent. Agents include, but are not limited to, in vitro synthetically prepared chemical compositions, antibodies, antigen binding regions, and combinations and conjugates thereof. In certain embodiments, an agent can act as an agonist, antagonist, allosteric modulator, or toxin.

In certain embodiments, the invention provides for pharmaceutical compositions comprising an antigen binding protein to ManLAM together with a pharmaceutically acceptable diluent, carrier, solubilizer, emulsifier, preservative and/or adjuvant.

In certain embodiments, the invention provides for pharmaceutical compositions comprising an antigen binding protein to ManLAM and a therapeutically effective amount of at least one additional therapeutic agent, together with a pharmaceutically acceptable diluent, carrier, solubilizer, emulsifier, preservative and/or adjuvant.

In certain embodiments, acceptable formulation materials preferably are nontoxic to recipients at the dosages and concentrations employed. In some embodiments, the formulation material(s) are for s.c. and/or I.V. administration. In certain embodiments, the pharmaceutical composition can contain formulation materials for modifying, maintaining or preserving, for example, the pH, osmolarity, viscosity, clarity, color, isotonicity, odor, sterility, stability, rate of dissolution or release, adsorption or penetration of the composition. In certain embodiments, suitable formulation materials include, but are not limited to, amino acids (such as glycine, glutamine, asparagine, arginine or lysine); antimicrobials; antioxidants (such as ascorbic acid, sodium sulfite or sodium hydrogen-sulfite); buffers (such as borate, bicarbonate, Tris-HCl, citrates, phosphates or other organic acids); bulking agents (such as mannitol or glycine); chelating agents (such as ethylenediamine tetraacetic acid (EDTA)); complexing agents (such as caffeine, polyvinylpyrrolidone, beta-cyclodextrin or hydroxypropyl-beta-cyclodextrin); fillers; monosaccharides; disaccharides; and other carbohydrates (such as glucose, mannose or dextrins); proteins (such as serum albumin, gelatin or immunoglobulins); coloring, flavoring and diluting agents; emulsifying agents; hydrophilic polymers (such as polyvinylpyrrolidone); low molecular weight polypeptides; salt-forming counterions (such as sodium); preservatives (such as benzalkonium chloride, benzoic acid, salicylic acid, thimerosal, phenethyl alcohol, methylparaben, propylparaben, chlorhexidine, sorbic acid or hydrogen peroxide); solvents (such as glycerin, propylene glycol or polyethylene glycol); sugar alcohols (such as mannitol or sorbitol); suspending agents; surfactants or wetting agents (such as pluronics, PEG, sorbitan esters, polysorbates such as polysorbate 20, polysorbate 80, triton, tromethamine, lecithin, cholesterol, tyloxapal); stability enhancing agents (such as sucrose or sorbitol); tonicity enhancing agents (such as alkali metal halides, preferably sodium or potassium chloride, mannitol sorbitol); delivery vehicles; diluents; excipients and/or pharmaceutical adjuvants. (Remington's Pharmaceutical Sciences, 18th Edition, A. R. Gennaro, ed., Mack Publishing Company (1995). In some embodiments, the formulation comprises PBS; 20 mM NaOAC, pH 5.2, 50 mM NaCl; and/or 10 mM NAOAC, pH 5.2, 9% Sucrose.

In certain embodiments, an antigen binding protein to ManLAM and/or a therapeutic molecule is linked to a half-life extending vehicle known in the art. Such vehicles include, but are not limited to, polyethylene glycol, glycogen (e.g., glycosylation of the ABP), and dextran. Such vehicles are described, e.g., in U.S. application Ser. No. 09/428,082, now U.S. Pat. No. 6,660,843 and published PCT Application No. WO 99/25044, which are hereby incorporated by reference for any purpose.

In certain embodiments, the optimal pharmaceutical composition will be determined by one skilled in the art depending upon, for example, the intended route of administration, delivery format and desired dosage. See, for example, Remington's Pharmaceutical Sciences, supra. In certain embodiments, such compositions may influence the physical state, stability, rate of in vivo release and rate of in vivo clearance of the antibodies of the invention.

In certain embodiments, the primary vehicle or carrier in a pharmaceutical composition can be either aqueous or non-aqueous in nature. For example, in certain embodiments, a suitable vehicle or carrier can be water for injection, physiological saline solution or artificial cerebrospinal fluid, possibly supplemented with other materials common in compositions for parenteral administration. In some embodiments, the saline comprises isotonic phosphate-buffered saline. In certain embodiments, neutral buffered saline or saline mixed with serum albumin are further exemplary vehicles. In certain embodiments, pharmaceutical compositions comprise Tris buffer of about pH 7.0-8.5, or acetate buffer of about pH 4.0-5.5, which can further include sorbitol or a suitable substitute therefore. In certain embodiments, a composition comprising an antigen binding protein to ManLAM, with or without at least one additional therapeutic agents, can be prepared for storage by mixing the selected composition having the desired degree of purity with optional formulation agents (Remington's Pharmaceutical Sciences, supra) in the form of a lyophilized cake or an aqueous solution. Further, in certain embodiments, a composition comprising an antigen binding protein to MANLAM, with or without at least one additional therapeutic agents, can be formulated as a lyophilizate using appropriate excipients such as sucrose.

In certain embodiments, the pharmaceutical composition can be selected for parenteral delivery. In certain embodiments, the compositions can be selected for inhalation or for delivery through the digestive tract, such as orally. The preparation of such pharmaceutically acceptable compositions is within the ability of one skilled in the art.

In certain embodiments, the formulation components are present in concentrations that are acceptable to the site of administration. In certain embodiments, buffers are used to maintain the composition at physiological pH or at a slightly lower pH, typically within a pH range of from about 5 to about 8.

In certain embodiments, when parenteral administration is contemplated, a therapeutic composition can be in the form of a pyrogen-free, parenterally acceptable aqueous solution comprising a desired antigen binding protein to ManLAM, with or without additional therapeutic agents, in a pharmaceutically acceptable vehicle. In certain embodiments, a vehicle for parenteral injection is sterile distilled water in which an antigen binding protein to ManLAM, with or without at least one additional therapeutic agent, is formulated as a sterile, isotonic solution, properly preserved. In certain embodiments, the preparation can involve the formulation of the desired molecule with an agent, such as injectable microspheres, bio-erodible particles, polymeric compounds (such as polylactic acid or polyglycolic acid), beads or liposomes, that can provide for the controlled or sustained release of the product which can then be delivered via a depot injection. In certain embodiments, hyaluronic acid can also be used, and can have the effect of promoting sustained duration in the circulation. In certain embodiments, implantable drug delivery devices can be used to introduce the desired molecule.

In certain embodiments, a pharmaceutical composition can be formulated for inhalation. In certain embodiments, an antigen binding protein to ManLAM, with or without at least one additional therapeutic agent, can be formulated as a dry powder for inhalation. In certain embodiments, an inhalation solution comprising an antigen binding protein to ManLAM, with or without at least one additional therapeutic agent, can be formulated with a propellant for aerosol delivery. In certain embodiments, solutions can be nebulized. Pulmonary administration is further described in PCT application no. PCT/US94/001875, which describes pulmonary delivery of chemically modified proteins.

In certain embodiments, it is contemplated that formulations can be administered orally. In certain embodiments, an antigen binding protein to ManLAM, with or without at least one additional therapeutic agents, that is administered in this fashion can be formulated with or without those carriers customarily used in the compounding of solid dosage forms such as tablets and capsules. In certain embodiments, a capsule can be designed to release the active portion of the formulation at the point in the gastrointestinal tract when bioavailability is maximized and pre-systemic degradation is minimized. In certain embodiments, at least one additional agent can be included to facilitate absorption of an antigen binding protein to ManLAM and/or any additional therapeutic agents. In certain embodiments, diluents, flavorings, low melting point waxes, vegetable oils, lubricants, suspending agents, tablet disintegrating agents, and binders can also be employed.

In certain embodiments, a pharmaceutical composition can involve an effective quantity of an antigen binding protein to ManLAM, with or without at least one additional therapeutic agents, in a mixture with non-toxic excipients which are suitable for the manufacture of tablets. In certain embodiments, by dissolving the tablets in sterile water, or another appropriate vehicle, solutions can be prepared in unit-dose form. In certain embodiments, suitable excipients include, but are not limited to, inert diluents, such as calcium carbonate, sodium carbonate or bicarbonate, lactose, or calcium phosphate; or binding agents, such as starch, gelatin, or acacia; or lubricating agents such as magnesium stearate, stearic acid, or talc.

Additional pharmaceutical compositions will be evident to those skilled in the art, including formulations involving antigen binding proteins to ManLAM, with or without at least one additional therapeutic agent(s), in sustained- or controlled-delivery formulations. In certain embodiments, techniques for formulating a variety of other sustained- or controlled-delivery means, such as liposome carriers, bio-erodible microparticles or porous beads and depot injections, are also known to those skilled in the art. See for example, PCT Application No. PCT/US93/00829 which describes the controlled release of porous polymeric microparticles for the delivery of pharmaceutical compositions. In certain embodiments, sustained-release preparations can include semipermeable polymer matrices in the form of shaped articles, e.g. films, or microcapsules. Sustained release matrices can include polyesters, hydrogels, polylactides (U.S. Pat. No. 3,773,919 and EP 058,481), copolymers of L-glutamic acid and gamma ethyl-L-glutamate (Sidman et al., Biopolymers, 22:547-556 (1983)), poly(2-hydroxyethyl-methacrylate) (Langer et al., J. Biomed. Mater. Res., 15:167-277 (1981) and Langer, Chem. Tech., 12:98-105 (1982)), ethylene vinyl acetate (Langer et al., supra) or poly-D(-)-3-hydroxybutyric acid (EP 133,988). In certain embodiments, sustained release compositions can also include liposomes, which can be prepared by any of several methods known in the art. See, e.g., Eppstein et al., Proc. Natl. Acad. Sci. USA, 82:3688-3692 (1985); EP 036,676; EP 088,046 and EP 143,949.

The pharmaceutical composition to be used for in vivo administration typically is sterile. In certain embodiments, this can be accomplished by filtration through sterile filtration membranes. In certain embodiments, where the composition is lyophilized, sterilization using this method can be conducted either prior to or following lyophilization and reconstitution. In certain embodiments, the composition for parenteral administration can be stored in lyophilized form or in a solution. In certain embodiments, parenteral compositions generally are placed into a container having a sterile access port, for example, an intravenous solution bag or vial having a stopper pierceable by a hypodermic injection needle.

In certain embodiments, once the pharmaceutical composition has been formulated, it can be stored in sterile vials as a solution, suspension, gel, emulsion, solid, or as a dehydrated or lyophilized powder. In certain embodiments, such formulations can be stored either in a ready-to-use form or in a form (e.g., lyophilized) that is reconstituted prior to administration.

In certain embodiments, kits are provided for producing a single-dose administration unit. In certain embodiments, the kit can contain both a first container having a dried protein and a second container having an aqueous formulation. In certain embodiments, kits containing single and multi-chambered pre-filled syringes (e.g., liquid syringes and lyosyringes) are included.

In certain embodiments, the effective amount of a pharmaceutical composition comprising an antigen binding protein to ManLAM, with or without at least one additional therapeutic agent, to be employed therapeutically will depend, for example, upon the therapeutic context and objectives. One skilled in the art will appreciate that the appropriate dosage levels for treatment, according to certain embodiments, will thus vary depending, in part, upon the molecule delivered, the indication for which an antigen binding protein to MAN-LAM, with or without at least one additional therapeutic agent, is being used, the route of administration, and the size (body weight, body surface or organ size) and/or condition (the age and general health) of the patient. In certain embodiments, the clinician can titer the dosage and modify the route of administration to obtain the optimal therapeutic effect. In certain embodiments, a typical dosage can range from about 0.1 µg/kg to up to about 100 mg/kg or more, depending on the factors mentioned above. In certain embodiments, the dosage can range from 0.1 µg/kg up to about 100 mg/kg; or 1 µg/kg up to about 100 mg/kg; or 5 µg/kg up to about 100 mg/kg.

In certain embodiments, the frequency of dosing will take into account the pharmacokinetic parameters of an antigen binding protein to ManLAM and/or any additional therapeutic agents in the formulation used. In certain embodiments, a clinician will administer the composition until a dosage is reached that achieves the desired effect. In certain embodiments, the composition can therefore be administered as a single dose, or as two or more doses (which may or may not contain the same amount of the desired molecule) over time, or as a continuous infusion via an implantation device or catheter. Further refinement of the appropriate dosage is routinely made by those of ordinary skill in the art and is within the ambit of tasks routinely performed by them. In certain embodiments, appropriate dosages can be ascertained through use of appropriate dose-response data.

In certain embodiments, the route of administration of the pharmaceutical composition is in accord with known methods, e.g. orally, through injection by intravenous, intraperitoneal, intracerebral (intra-parenchymal), intracerebroventricular, intramuscular, subcutaneously, intra-ocular, intraarterial, intraportal, or intralesional routes; by sustained release systems or by implantation devices. In certain embodiments, the compositions can be administered by bolus injection or continuously by infusion, or by implantation device.

In certain embodiments, the composition can be administered locally via implantation of a membrane, sponge or another appropriate material onto which the desired molecule has been absorbed or encapsulated. In certain embodiments, where an implantation device is used, the device can be implanted into any suitable tissue or organ, and delivery of the desired molecule can be via diffusion, timed-release bolus, or continuous administration.

In certain embodiments, it can be desirable to use a pharmaceutical composition comprising an antigen binding protein to ManLAM, with or without at least one additional therapeutic agent, in an ex vivo manner. In such instances, cells, tissues and/or organs that have been removed from the patient are exposed to a pharmaceutical composition comprising an antigen binding protein to ManLAM, with or without at least one additional therapeutic agent, after which the cells, tissues and/or organs are subsequently implanted back into the patient.

In certain embodiments, an antigen binding protein to ManLAM and/or any additional therapeutic agents can be delivered by implanting certain cells that have been genetically engineered, using methods such as those described herein, to express and secrete the polypeptides. In certain embodiments, such cells can be animal or human cells, and can be autologous, heterologous, or xenogeneic. In certain embodiments, the cells can be immortalized. In certain embodiments, in order to decrease the chance of an immunological response, the cells can be encapsulated to avoid infiltration of surrounding tissues. In certain embodiments, the encapsulation materials are typically biocompatible, semipermeable polymeric enclosures or membranes that allow the release of the protein product(s) but prevent the destruction of the cells by the patient's immune system or by other detrimental factors from the surrounding tissues.

Diagnostic Applications

In some embodiments, an ABP is used as a diagnostic tool. The ABP can be used to assay the amount of ManLAM present in a sample and/or subject. The ABP can be used to detect the presence or absence of ManLAM in a sample and/or subject.

In some embodiments, the ABPs disclosed herein are used or provided in an assay kit and/or method for the detection of ManLAM in mammalian tissues or cells in order to screen/ diagnose for a disease or disorder associated with changes in levels of ManLAM or the presence of ManLAM. The kit comprises an ABP that binds ManLAM and means for indicating the binding of the ABP with ManLAM, if present, and optionally ManLAM levels. Various means for indicating the presence of an ABP can be used. For example, fluorophores, other molecular probes, labels, or enzymes can be linked to the ABP and the presence of the ABP can be observed in a variety of ways. The method for screening for such disorders can involve the use of the kit, or simply the use of one of the disclosed ABPs and the determination of whether the ABP binds to ManLAM in a sample. As will be appreciated by one of skill in the art, high or elevated levels of ManLAM will result in larger amounts of the ABP binding to ManLAM in the sample. Thus, degree of ABP binding can be used to determine how much ManLAM is in a sample. Subjects or samples with an amount of ManLAM that is greater than a predetermined amount (e.g., an amount or range that a person without a MANLAM related disorder would have) can be characterized as having a ManLAM associated disorder.

Immunoassays

The ABPs, can also be used in immunoassays for diagnosing or prognosing pathogenic mycobacteria infection in a mammal. It will be understood that a target analyte in the immunoassays and related methods is a region of ManLAM, although two or more target analytes may include a second analyte that is not the same region of ManLAM or is not ManLAM. Immunoassays include such techniques commonly recognized in the art, including for example radioimmunoassay, Western blot assay, immunofluorescent assay, enzyme immunoassay, chemiluminescent assay, immunohistochemical assay, immunoprecipitation and the like. Standard techniques known in the art for ELISA are well-known and described for example in Methods in Immunodiagnosis, 2nd Edition, Rose and Bigazzi, eds., John Wiley and Sons, 1980 and Campbell et al., Methods of Immunology, W. A. Benjamin, Inc., 1964, both of which are incorporated herein by reference Immunoassays may be a direct, indirect, competitive, or noncompetitive immunoassay as described in the art (Oellerich, M. 1984. J. Clin. Chem. Clin. BioChem 22:895 904). Biological samples appropriate for such detection assays include, but are not limited to blood, plasma, serum, liver, saliva, lymphocytes or other mononuclear cells.

An immunoassay for determining the presence or amount of pathogenic mycobacteria and/or ManLAM in a sample may comprise, for example, providing a binding reagent comprising any one of the ABPs as described herein, combining the ABP with the sample for a time sufficient for the reagent to bind to any mycobacteria that may be present in the sample, and determining the presence or amount of mycobacteria present in the sample based on specific binding of the ABP to the ManLAM. The disclosure also encompasses an immunoassay device for detecting the presence or absence of pathogenic mycobacteria in a sample, wherein the device comprises any of the ABPs described herein immobilized on a solid support. The ABPs may be prepared in the form of a kit, alone, or in combinations with other reagents such as secondary antibodies, for use in immunoassays.

Methods of detecting the presence of an analyte such as ManLAM can comprise contacting the sample with at least one ABP, including a monoclonal antibody as described herein. Any suitable assay as is known in the art can be used in the method. Examples include, but are not limited to, immunoassay, such as sandwich immunoassay (e.g., monoclonal and/or polyclonal sandwich immunoassays or any variation thereof, including radioisotope detection (radioimmunoassay (RIA)) and enzyme detection (enzyme immunoassay (EIA) or enzyme-linked immunosorbent assay (ELISA) (e.g., Quantikine ELISA assays, R&D Systems, Minneapolis, Minn.)), competitive inhibition immunoassay (e.g., forward and reverse), fluorescence polarization immunoassay (FPIA), enzyme multiplied immunoassay technique (EMIT), bioluminescence resonance energy transfer (BRET), and homogeneous chemiluminescent assay, etc. In a SELDI-based immunoassay, a capture reagent that specifically binds an analyte of interest such as ManLAM (or a fragment thereof) is attached to the surface of a mass spectrometry probe, such as a pre-activated protein chip array. The analyte (or a fragment thereof) is then specifically captured on the biochip, and the captured analyte (or a fragment thereof) is detected by mass spectrometry. Alternatively, the analyte (or a fragment thereof) can be eluted from the capture reagent and detected by traditional MALDI (matrix-assisted laser desorption/ionization) or by SELDI. A chemiluminescent microparticle immunoassay is an example of an immunoassay.

Methods well-known in the art for collecting, handling and processing urine, blood, serum and plasma, and other body fluids, can be used in the practice of the present disclosure, for instance, when a ABP as described herein is employed as an immunodiagnostic reagent and/or in an analyte immunoassay kit. The test sample can comprise further moieties in addition to the analyte of interest, such as antibodies, antigens, haptens, hormones, drugs, enzymes, receptors, proteins, peptides, polypeptides, oligonucleotides and/or polynucleotides. For example, the sample can be a whole blood sample obtained from a subject. It can be necessary or desired that a test sample, particularly whole blood, be treated prior to immunoassay, e.g., with a pretreatment reagent. Even in cases where pretreatment is not necessary (e.g., most urine samples), pretreatment optionally can be done (e.g., as part of a regimen on a commercial platform). Other immunoassays, kits, and related aspects are described at paragraphs 186-274 of the published version of U.S. Pat. App. 20120009196, which is herein incorporated by reference in its entirety.

Kits

A kit for assaying a test sample for the presence, amount or concentration of ManLAM (or a fragment thereof) in a test sample is also provided. The kit comprises at least one component for assaying the test sample for ManLAM (or a fragment thereof) and instructions for assaying the test sample for the analyte (or a fragment thereof). The at least one component for assaying the test sample for the analyte (or a fragment thereof) can include a composition comprising an ABP (or a fragment, a variant, or a fragment of a variant thereof), which is optionally immobilized or capable of being immobilized on a solid phase.

The kit can comprise at least one component for assaying the test sample for ManLAM by immunoassay, e.g., chemiluminescent microparticle immunoassay, and instructions for assaying the test sample for an analyte by immunoassay, e.g., chemiluminescent microparticle immunoassay. For example, the kit can comprise at least one specific binding partner for an analyte, such as an anti-analyte, monoclonal/polyclonal antibody (or a fragment thereof that can bind to the analyte, a variant thereof that can bind to the analyte, or a fragment of a variant that can bind to the analyte) or an anti-analyte ABP (or a fragment, a variant, or a fragment of a variant thereof), either of which can be detectably labeled. Alternatively or additionally, the kit can comprise detectably labeled analyte (or a fragment thereof that can bind to an anti-analyte, monoclonal/polyclonal antibody or an anti-analyte ABP (or a fragment, a variant, or a fragment of a variant thereof)), which can compete with any analyte in a test sample for binding to an anti-analyte, monoclonal/polyclonal antibody (or a fragment thereof that can bind to the analyte, a variant thereof that can bind to the analyte, or a fragment of a variant that can bind to the analyte) or an anti-analyte ABP (or a fragment, a variant, or a fragment of a variant thereof), either of which can be immobilized on a solid support. The kit can comprise a calibrator or control, e.g., isolated or purified analyte. The kit can comprise at least one container (e.g., tube, microtiter plates or strips, which can be already coated with a first specific binding partner, for example) for conducting the assay, and/or a buffer, such as an assay buffer or a wash buffer, either one of which can be provided as a concentrated solution, a substrate solution for the detectable label (e.g., an enzymatic label), or a stop solution. In some aspects, the kit comprises all components, i.e., reagents, standards, buffers, diluents, etc., which are necessary to perform a desired assay. The instructions can be in paper form or computer-readable form, such as a disk, CD, DVD, or the like. Instructions can be displayed on a user interface such as a computer monitor.

Any ABPs, such as an anti-analyte antibody, or tracer can incorporate a detectable label as described herein, such as a fluorophore, a radioactive moiety, an enzyme, a biotin/avidin label, a chromophore, a chemiluminescent label, or the like, or the kit can include reagents for carrying out detectable labeling. The antibodies, calibrators and/or controls can be provided in separate containers or pre-dispensed into an appropriate assay format, for example, into microtiter plates.

In some aspects, the kit includes quality control components (for example, sensitivity panels, calibrators, and positive controls). Preparation of quality control reagents is well-known in the art and is described on insert sheets for a variety of immunodiagnostic products. Sensitivity panel members optionally are used to establish assay performance characteristics, and further optionally are useful indicators of the integrity of the immunoassay kit reagents, and the standardization of assays.

The kit can also optionally include other reagents required to conduct a diagnostic assay or facilitate quality control evaluations, such as buffers, salts, enzymes, enzyme co-factors, enzyme substrates, detection reagents, and the like. Other components, such as buffers and solutions for the isolation and/or treatment of a test sample (e.g., pretreatment reagents), also can be included in the kit. The kit can additionally include one or more other controls. One or more of the components of the kit can be lyophilized, in which case the kit can further comprise reagents suitable for the reconstitution of the lyophilized components.

The various components of the kit optionally are provided in suitable containers as necessary, e.g., a microtiter plate. The kit can further include containers for holding or storing a sample (e.g., a container or cartridge for a urine sample). Where appropriate, the kit optionally also can contain reaction vessels, mixing vessels, and other components that facilitate the preparation of reagents or the test sample. The kit can also include one or more instruments for assisting with obtaining a test sample, such as a syringe, pipette, forceps, measured spoon, or the like.

If the detectable label is at least one acridinium compound, the kit can comprise at least one acridinium-9-carboxamide, at least one acridinium-9-carboxylate aryl ester, or any combination thereof. If the detectable label is at least one acridinium compound, the kit also can comprise a source of hydrogen peroxide, such as a buffer, a solution, and/or at least one basic solution. If desired, the kit can contain a solid phase, such as a magnetic particle, bead, test tube, microtiter plate, cuvette, membrane, scaffolding molecule, film, filter paper, disc or chip.

The kit (or components thereof), as well as the method of determining the presence, amount or concentration of an analyte in a test sample by an assay, such as an immunoassay as described herein, can be adapted for use in a variety of automated and semi-automated systems (including those wherein the solid phase comprises a microparticle), as described, e.g., in U.S. Pat. Nos. 5,089,424 and 5,006,309.

EXAMPLES

Below are examples of specific embodiments for carrying out the present invention. The examples are offered for illustrative purposes only, and are not intended to limit the scope of the present invention in any way. Efforts have been made to ensure accuracy with respect to numbers used (e.g., amounts, temperatures, etc.), but some experimental error and deviation should, of course, be allowed for.

The practice of the present invention will employ, unless otherwise indicated, conventional methods of protein chemistry, biochemistry, recombinant DNA techniques and pharmacology, within the skill of the art. Such techniques are explained fully in the literature. See, e.g., T. E. Creighton, *Proteins: Structures and Molecular Properties* (W.H. Freeman and Company, 1993); A. L. Lehninger, *Biochemistry* (Worth Publishers, Inc., current addition); Sambrook, et al., *Molecular Cloning: A Laboratory Manual* (2nd Edition, 1989); *Methods In Enzymology* (S. Colowick and N. Kaplan eds., Academic Press, Inc.); *Remington's Pharmaceutical Sciences,* 18th Edition (Easton, Pa.: Mack Publishing Company, 1990); Carey and Sundberg *Advanced Organic Chemistry* $3^{rd}$ *Ed.* (Plenum Press) Vols A and B (1992).

Methods

Phage Display Panning and Screening of Monoclonal Plume Antibodies

A non-immune human Fab-antibody phage display library (Humanyx Pte Ltd, Singapore) constructed by the method of Hans de Haard et al (1) was screened for anti-LAM antibodies after multiple rounds of selection on *Mycobacterium tuberculosis* mannose-capped LAM (ManLAM, Nacalai Tesque, Japan) coupled with negative depletion on *Mycobacterium smegmatis* phosphoinositide-capped LAM (PILAM, Invivogen, US). Briefly, cross-reactive LAM antibodies were first depleted from the library by preabsorbtion to 100 μg PILAM coated onto a Maxisorb immunotube (Nunc, Denmark). Remaining cross-reactive antibodies were blocked in solution by the addition of 100 μg of soluble PILAM. The phage library was then applied to a Maxisorb immunotube coated with 100 μg of ManLAM to pull out anti-ManLAM antibodies. Unbound phage were removed by repeated washing with 2% skim milk block in 1×PBS/0.05% Tween, followed by 1×PBS/0.05% Tween and 1×PBS washes. Bound phage was recovered by enzymatic elution with trypin at 37° C. for 30 min and re-infected into TG1 *E. coli* for the library recovery. Infected TG1 was further infected with M13KO7 helper phage (New England biolabs, US) and grown overnight at 30° C. on 2YT agar plates. Expressed phage was recovered the next day by PEG precipitation and used for the next round of selection. Solid surface pre-absorption was carried out only for the first two rounds of selection and a total of four rounds of selection was carried out. For selection without negative depletion, the steps of pre-absorption onto immunotubes and blocking in solution with PILAM were left out. Polyclonal phage ELISA was carried out as described below to assess for enrichment of ManLAM-specific antibodies.

Phage libraries enriched for anti-ManLAM antibodies were screened for positive clones by direct binding ELISA. Briefly, infected TG1 stock was plated out to obtain single colonies; approximately 400 clones were grown up in 2 ml 96-deep well plates and infected with M13KO7 helper phage. Monoclonal phage secreted into the culture supernatant was recovered and tested for binding to ManLAM as described below. Subsequently, antibody coding sequences were amplified by colony PCR with specific primers using Hotstar Taq (Qiagen, Germany) from 1 μl of bacterial culture and digested with BstN1. Clones with identical restriction digest patterns were considered to be identical and 2 to 3 clones representative of each unique pattern were then sequenced to confirm their identity.

Construction of Human-Mouse Chimerics

Human G1 and G3 CH1 sequences and Mouse G2a CH2 and CH3 (Fc) sequences were amplified with primers designed to permit a second overlapping PCR of the human CH1 and mouse Fc sequences as follows, human G1 CH1: SEQ1B 5'-CGGATCTCTAGCGAATTCC-3' (SEQ ID NO:1) & HuG1MoG2aRev 5'-CCACCCAAGAGGTTAG-GTGCTGGGCACGGTGGGCATGTG-3' (SEQ ID NO:2); human G3 CH1: SEQ and HuG3MoG2aRev 5'-CCAC-CCAAGAGGTTAGGTGCTGGGCAC-CGTGGGCATGGGGG-3' (SEQ ID NO:3); Mouse G2a: HuG1MoG2aFor 5'-CACATGCCCACCGTGCCCAGCAC-CTAACCTCTTGGGTGG-3' (SEQ ID NO:4) or HuG3MoG2aFor 5'-CCCCCATGCCCACGGTGCCCAG-CACCTAACCTCTTGGGTGG-3' (SEQ ID NO:5) with MoG2aRev 5'-ATCCAGCTTCTAGACTATTTACCCG-GAGTCCGGGAGAAG-3' (SEQ ID NO:6). PCR was carried out for 30 cycles at an annealing temperature of 56° C. for 30 s and extension at 72° C. for 1 min for CH1 sequences and an annealing at 62° C. for 30 s and extension at 72° C. for 2 min for Fc sequences. A second PCR to overlap the CH1 and Fc sequences was done with five cycles of PCR without primers at an annealing temperature of 62° C. for 30 s and extension at 72° C. for 2 min, followed by 25 rounds of PCR with SEQ1B and MoG2aRev primers added at an annealing temperature of 56° C. for 30 s to amplify the final chimeric sequence which was then cloned into the heavy chain expression vector described below.

Expression of Mammalian IgG and Production of Labeled Antibodies

Antibody light chain and variable heavy coding sequences were cloned into a cytomegalovirus promoter driven mammalian expression vector as separate constructs and co-transfected into HEK293 suspension cultures for expression of full length IgG. For the heavy chain constructs, the vector already contains the heavy constant coding sequence in frame with the variable region for expression of the full length heavy chain. Fully assembled IgG were secreted into the culture supernatant and purified either on Protein A or Protein G columns (Pierce Thermo Scientific, US) either by gravity flow for small scale purification or by HPLC on AKTA purifier (GE Healthcare, US) for large scale volumes, eluted with IgG elution buffer (Pierce Thermo Scientific, US) and buffer exchanged into 1×PBS. Purified antibodies were labeled with either Lightning Link-HRP labeling kit (Innova Biosciences, UK) at a HRP:antibody molar ratio of 4:1 or Alexa488 fluorescent dye (Invitrogen, US) according to manufacturer's instructions.

Sandwich and Direct Binding ELISA

For direct binding ELISAs with phage, 96-well Maxisorb ELISA plates (Nunc, Denmark) were coated with LAM antigen in 1×PBS at indicated concentrations overnight at 4° C. ELISA plates were then washed twice with 1×PBS and blocked with 380 μl per well of Casein block in PBS (Pierce Thermo Scientific, US) at room temperature for 2 hrs. The plates were washed twice and then polyclonal phage at 1:10 dilution or monoclonal phage at 1:2 dilution in casein block was added. Plates were washed four times with 1×PBS and then bound phage detected with HRP-conjugated anti-M13 polyclonal antibody (GE Healthcare, US) diluted 1:5000 in casein block. Plates were washed another four times with 1×PBS before colour development with TMB for 10 min. For serial dilutions of IgG and Kd estimation, incubations of primary and secondary antibody and TMB were done at 37° C. to ensure binding had reached equilibrium.

For sandwich ELISA, plates were coated with 5 µg/ml capture antibody in 1×PBS overnight at 4° C. and blocked and washed with 1×PBS as above before adding antigen. Antigen was prepared as follows: LAM was purchased from commercial sources and H37Rv LAM was provided by Colorado State University and spiked into 1×PBS or urine. Spiked urine samples were heated at 99° C. for 30 min and centrifuged at 16000 g for 15 min and supernatant recovered for use. Live mycobacterial culture was grown up to log-phase growth in Middlebrook 7H9 media (BD Diagnostics, US) at 37° C. (with 5% $CO_2$ for BCG). Bacteria was spun down and resuspended in 1×PBS to OD 0.5 and culture media supernatants were recovered and filter sterilized for use. Inactivated TB (H37Rv strain) was kindly provided by Dr Sylvie Alonso. After antigen binding, the plate was washed four times with 1×PBS and then detector antibody added at 2.5 µg/ml in casein block. The ELISA plate was washed four times with 1×PBS again and my2F12 binding was detected by secondary HRP labeled anti-human Fc or anti-mouse Fc antibody (Pierce Thermo Scientific, US) at 1:5000 dilution in casein block. Signal was developed using TMB incubated for 8 min and stopped with 1M sulphuric acid. ELISA with polyclonal αLAM was carried out using pre-coated plates and HRP-conjugated antibody from Clearview commercial LAM ELISA kit (Inverness Medical Innovations, UK) used according to manufacturer's instructions. All incubations are at 100 µl volume for 1 hr at room temperature unless otherwise indicated. ELISA with live mycobacteria was carried out in a Biological Safety Cabinet and washes done with a vacuum aspirator.

Immunofluorescence and Acid Fast Staining

Cover slips were rinsed with deionized water and 100% ethanol and then dried on a heating block at 60° C. Approximately $10^6$ cfu of mycobacteria resuspended in 30 µl of water was pipetted onto the cover slip and allowed to dry onto the cover slip on the heating block at 60° C. The cover slips were then transferred to a 24-well plate and fixed with 500 µl of 1:1 mix of methanol-acetone for 30 min at −20° C. for immunofluorescence or 5% phenol-70% ethanol solution for 15 min at room temperature for acid fast staining respectively. Cover slips were then taken out of the fixative and allowed to dry.

For immunofluorescence, fixed cover slips were washed once with 1×PBS and then blocked with 2% fetal calf serum in 1×PBS, washed again with 1×PBS and then incubated with primary antibody, either 5 µg/ml my2F12-MoG2a or 1:200 rabbit anti-LAM polyclonal (Acris Antibodies, Germany) in blocking solution. Cover slips were then washed with two 5-min incubations in 1×PBS/0.05% Tween and rinsed in PBS before incubation with secondary antibody, either anti-rabbit or anti-mouse polyclonal (Invitrogen, US) conjugated to Alexa Fluor 594 and 488 respectively, at 1:100 dilution in blocking solution. The cover slips were washed again as above, rinsed in deionized water before mounting with Mowoil on glass slides. All washes were done in 24-well plates and incubations done on parafilm with 50 µl of reagent for 30 min at room temperature. Mounted slides were viewed using a Confocal Laser Microscope system (Leica, Germany).

For acid fast staining, fixed slides were stained with TB Quickstain (BD Diagnostics, US) according to manufacturer's instructions in 24-well plates. Briefly, the slides were stained with carbolfushin for 5 min, rinsed liberally with deionized water then flooded with TB Quickstain Methylene Blue to counterstain for 3 min and then rinsed again with deionized water. Cover slips were allowed to dry and then fixed to glass slides and viewed under a light microscope (Leica, Germany).

Carbohydrate Microarrays

Carbohydrate microarrays were fabricated as described previously (2). In brief, GAPS II slides (Corning, US) were submerged in DMF containing 2% diisopropylethlyamine and 0.5 mg/mL maleimido-N-hydroxysuccinimide hexanoic acid for 14 h at room temperature. Functionalized slides were washed three times with methanol, dried and stored under an argon atmosphere. The functionalized oligosaccharides were synthesized as described previously (3, 4). The oligosaccharide compounds with one molar equivalent TCEP to reduce disulfides were dissolved to the desired concentration in PBS. Per spot, 1 nL of the solution was printed onto the maleimide functionalized slides using an automated printing robot in replicates of ten at four different concentrations (2 mM, 0.4 mM, 80 µM and 16 µM). Slides were incubated in a humid chamber to complete reaction for 24 h and stored in a dessicator until usage. Printed carbohydrate microarray slides were washed three times with water and quenched in 0.1% (v/v) β-mercaptoethanol in PBS for 1 h at room temperature. Afterwards, slides were washed three times with water and two times with ethanol. Slides were blocked by a solution of 2.5% BSA in Tris buffer with calcium (20 mM Tris, 150 mM NaCl, 1 mM $CaCl_2$, pH 7.4 for 1 h at room temperature, washed three times with Tris buffer with calcium and centrifuged. The antibody (50 µg/mL) was incubated on the slides in in 20 mM HEPES, 150 mM NaCl, 1 mM $CaCl_2$, pH 7.4, washed three times with the same Buffer and centrifuged. For inhibition, mannan, PILAM or ManLAM (each at a final concentration of 30 µg/mL) was added to the incubation solution. A fluorescence-labeled detection antibody (10 µg/mL in 20 mM HEPES, 150 mM NaCl, 1 mM $CaCl_2$, pH 7.4; Invitrogen) was incubated on the slide in a similar fashion. Afterwards, slides were scanned using a fluorescence microarray scanner (GenePix 4300A, Molecular Devices).

METHODS REFERENCES 1. de Haard, H. J. W (2001) Construction of large naïve Fab libraries. *Methods Mol Biol* 178, 87-100
2. Adams, E. W., Ratner, D. M., Bokesch, H. R., McMahon, J. B., O'Keefe, B. R., and Seeberger, P. H. (2004) Oligosaccharide and glycoprotein microarrays as tools in HIV glycobiology; glycan-dependent gp120/protein interactions, *Chem Biol* 11, 875-881.
3. Ratner, D. M., Plante, O. J., and Seeberger, P. H. (2002) A linear synthesis of branched high-mannose oligosaccharides from the HIV-1 viral surface envelope glycoprotein gp120, *European Journal of Organic Chemistry*, 826-833.
4. Holemann, A., Stocker, B. L., and Seeberger, P. H. (2006) Synthesis of a core arabinomannan oligosaccharide of Mycobacterium tuberculosis, *J Org Chem* 71, 8071-8088.

Example 1

Phage Display Screening and Antibody Characterization

Figure 1:
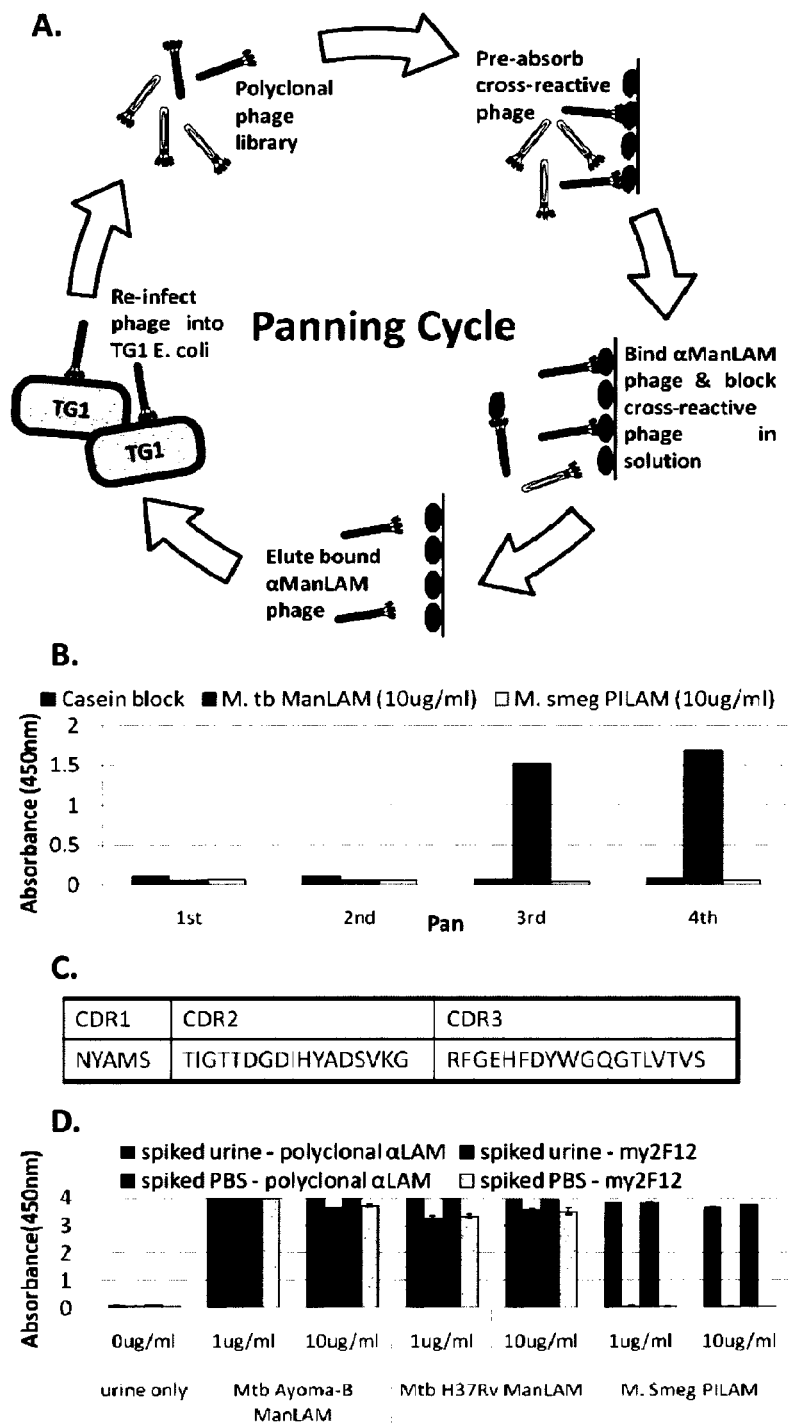
FIG. 1 shows (A) Procedure for phage panning with negative selection (B) Selective enrichment of Humanyx library for ManLAM-specific binders as indicated by direct binding polyclonal phage ELISA (C) CDR amino acid sequence of isolated unique clone my2F12 (SEQ ID NOS 7-9, respectively, in order of appearance) (D) Specificity of my2F12 for *M. tuberculosis* ManLAM over *M. smegmatis* PILAM as compared to commercial polyclonal anti-LAM as indicated by sandwich ELISA on spiked PBS and urine samples.

We have developed a novel method of phage display screening that uses a related antigen, phosphoinositol-capped lipoarabinomannan (PILAM), to deplete cross-reactive epitopes from a non-immune human antibody phage display library in order to enhance specificity for the targeted unique region of the desired antigen, the α1-2 mannose caps of ManLAM (FIG. 1A). Using this method, we were able to demonstrate ManLAM-specific enrichment of the phage library from Pan 1 to Pan 4 polyclonals as measured by direct binding polyclonal phage ELISA (FIG. 1B). No increase in binding for PILAM was observed from Pan 1 to Pan 4, indicating that there was no enrichment for cross-reactive or PILAM-specific antibodies.

Analysis of the antibody repertoire of the enriched Pan 4 library by restriction fragment length polymorphism analysis and sequencing of selected monoclonals indicated that that there was only one unique clone present (FIG. 1B). This clone, named my2F12, was cloned into a mammalian expression vector carrying the huG1 constant region and transiently expressed in cell culture. This full length IgG was tested for ManLAM specificity and was able to distinguish ManLAM from two different Mtb strains from PILAM from M. smegmatis in sandwich ELISA on both spiked PBS and urine samples (FIG. 1C-D) (Heavy Chain CDRs: CDR1-NYAMS (SEQ ID NO:7); CDR2-TIGTTDGDIHYADSVKG (SEQ ID NO:8); CDR3-RFGEHFDYWGQGTLVTVS (SEQ ID NO:9)). See also, Table 1. The my2F12 vector has been deposited with ATCC Patent Depository in Manassas, Va. on Feb. 21, 2012 under the number PTA-12554, which is herein incorporated by reference for all purposes.

To further confirm the specificity of this antibody for the mannose capping motifs, the antibody was tested for binding to various synthetic carbohydrates printed onto microarray slides (FIG. 2). The antibody was found to bind only mannose oligosaccharides containing α1-2 mannose linkages and did not bind mannose oligosaccharides or phosphoinositol mannosides (PIMs) with only α1-4 or α1-6 mannose linkages. No binding was observed to other saccharides consisting of other hexose or pentose monomers, such as maltotriose, fucose, rhamnose, lactose, galactose, and di- & hexa-arabinan (FIG. 5). This specificity of my2F12 for α1-2 mannose linkage thus clarifies and confirms our earlier result showing specificity for the mannose-caps of ManLAM.

Example 2

My2F12 Specificity on Confocal IF Microscopy

In order to determine the utility of this antibody for immunofluorescence (IF) detection of intact tuberculosis bacteria on sputum smears, we evaluated the specificity of my2F12 for various mycobacterial and actinomycete species on slides of fixed bacterial culture via confocal IF microscopy. A chimeric antibody consisting of a human light chain and heavy variable region and a mouse G2a constant region was used instead as the original fully human antibodies are likely to give significant background if used in a sputum sample, due to detection of endogenous antibodies in the sample by the secondary antibody. See Table 1. In this case an anti-mouse fluorescently labeled secondary antibody was used. The non-mycobacterial actinomycete species chosen were two that have been isolated from clinical sputum samples and previously shown to cross react with polyclonal αLAM antibodies and hence could potentially give false positives; *Nocardia cyriacigeorgica* and *Tsukumurella paurometabolum*. The Gram negative bacteria *Escherichia coli* was also included as a negative control. As a comparison, a commercial rabbit polyclonal αLAM IF and the traditional Ziehl-Neelsen acid-fast stain was also carried out on duplicates of these slides. A classification of the species used, their pathogenicity and IF and acid-fast stain results is given in FIG. 3A.

Slow-growing mycobacterial species such as *M. bovis* BCG were positive for both my2F12 and polyclonal αLAM IF as well as the acid-fast stain, as expected from previous studies indicating that ManLAM was expressed in mycobacteria exclusively by the slow-growing species (FIG. 3B). On the other hand, all fast growing mycobacterial species such as *M. smegmatis* could not be detected by my2F12 IF but were uniformly positive for polyclonal αLAM IF as well as the acid-fast stain (FIG. 3C). For the non-mycobacterial actinomycete species, all were negative for the acid-fast stain but positive for polyclonal αLAM IF, confirming earlier studies of LAM antibody cross-reactivity (FIG. 3D). Interestingly however, *T. paurometabolum* could also be visualized by my2F12 IF. Although this result suggests a potential for false positives on samples containing this bacterium, it nevertheless correlates with a report that the LAM-related glycolipid produced by this species contains α1-2 mannose linkages.

Example 3

Avidity of My2F12 Chimeric IgG

Another diagnostic option is to use the antibody in an ELISA-type assay. This class of immunoassay is particularly useful as it can rapidly adapted into a lateral-flow type test suitable for rapid point-of-care screening. However, in this type of assay, antibody avidity is key in determining the detection limit. As modification of constant regions and antibody isotype is known to affect avidity, we analyzed the effect of isotype changes on my2F12 from human G1 to mouse G2a as well as human G3. See Table 1. We theorized that the increased flexibility of the human G3 hinge region might reduce steric hindrance of binding to a large branched LAM molecule and hence increase avidity, while a switch from the native human to a mouse constant region might negatively impact the correct structure of the variable regions and reduce avidity. The mouse equivalent of human G3 (mouse G1) was not used as its hinge is not significantly longer than mouse G2a. We therefore tested the mouse G2a chimeric antibody (moG2a) used earlier for the confocal IF microscopy along with human G1 and G3 isotypes of my2F12 (huG1full and huG3full respectively). A mouse chimeric version in which the human light chain constant region was replaced with the equivalent mouse kappa light chain (moG2afull) was also made in case the mismatched pairing of human light chain with mouse CH1 constant region resulted in reduced avidity. As fully human antibodies cannot be used due to the potential for high background from human clinical samples, we made an additional two chimerics of human G1 and G3 isotypes in which only the Fc region was replaced with an equivalent mouse was made. If switching the constant region from human to mouse indeed reduces avidity, switching only the Fc region should have a lesser effect as the impact on the Fab domain is mitigated by the flexible hinge. The construction of these six chimerics is illustrated in FIG. 4A. See also Table 1.

The Kd values were also determined for each of the my2F12 antibodies. See Table 2. To determine the Kd values, ELISA plates were coated overnight with 1 μg/ml of mannose-capped lipoarabinomannan at 4° C., washed twice with phosphate buffered saline (PBS) and blocked with 360 μl/well Casein (Thermo Scientific) for 2 hours at room temperature (app. 25° C.). Plates were washed twice with PBS and incubated with antibody in Casein block at concentrations from 100 to 0.0001 nM at half-log serial dilution and incubated 1 hour at 37° C. Plates were then washed four times with PBS and incubated with anti-HuFc secondary antibody (Thermo Scientific) in Casein block at 1:5000 dilution for 1 hour at 37° C., washed again four times with PBS and color developed with TMB (Thermo Scientific) and stopped after 10 minutes at 37° C. with 2M sulphuric acid. Raw absorbance values were plotted and relative Kd value calculated using GraphPad Prism 5 with the one-site specific binding model. All volumes were at 100 μl/well, unless indicated otherwise. The Kd value determined for each antibody is shown in Table 2.

TABLE 2

| Antibody Name | Kd Value |
|---|---|
| huG3full | 2.268e-010M |
| huG1full | 4.388e-010M |
| hG3mG2a | 6.380e-010M |
| hG1mG2a | 1.464e-009M |
| moG2a | 3.134e-009M |
| moG2a full | 5.133e-009M |

Figure 4:
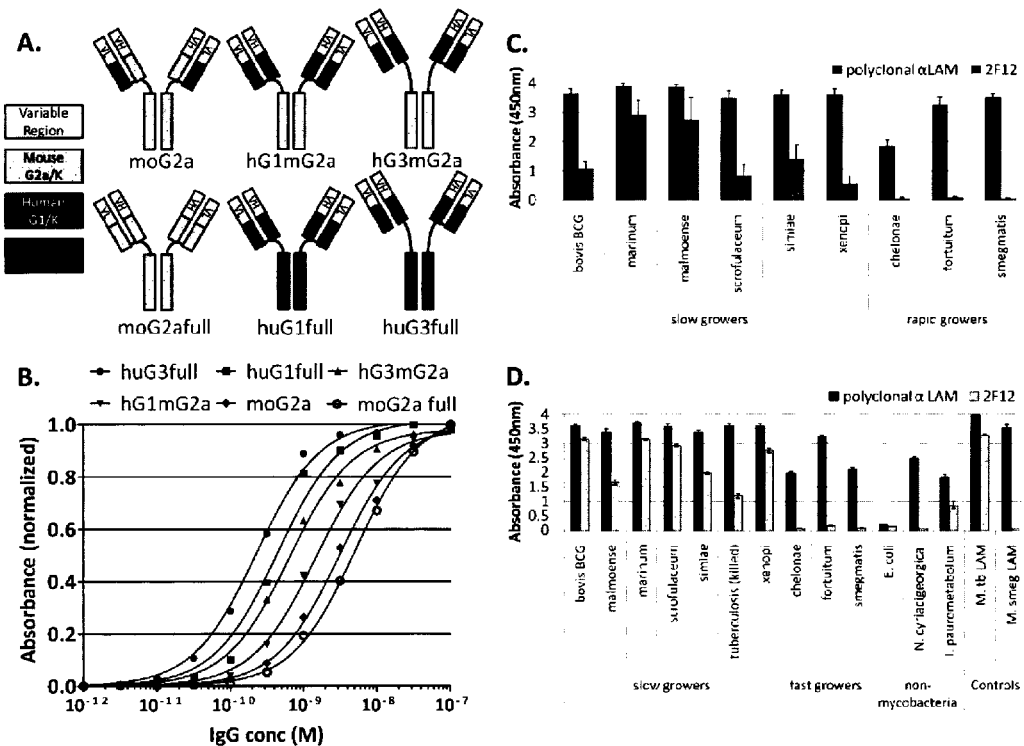
FIG. 4 shows (A) Construction of mouse-human chimeric antibodies indicating isotype and species origin of CH1, Fc and variable regions. (B) Serial dilution of IgG against ManLAM on direct binding ELISA showing relative affinities of different chimeric constructs. (C) Sandwich ELISA with 2F12 huG1 isotype as detector and 2F12 Fab fragment as capture against mycobacterial culture supernatants indicating specificity of original human construct for slow-growing mycobacteria A commercial polyclonal αLAM kit was used as a comparison. (D) Sandwich ELISA with hG3mG2a mouse-human chimeric as detector and HuG1 as capture against whole bacteria indicating similar specificity for mycobacteria and nonspecificity for majority of non-mycobacterial species.

The relative avidities of these antibodies were analyzed by direct binding of serially diluted antibody to a fixed concentration of ManLAM by ELISA (FIG. 4B). As expected, native fully human G1 and G3 antibodies had the highest avidity with G3 isotype having slightly better avidity. Switching either the heavy constant or both heavy and light constant regions to mouse significantly affected avidity with a greater than one-log shift in the dilution curve for the fully mouse constant region antibody (moG2afull). Interestingly, the chimeric antibodies having only the Fc region replaced i.e. CH1 and hinge region still human, had intermediate avidities. This suggests that the flexible hinge cannot completely isolate the Fab region from changes in the Fc structure. The Fc intermediate with the G3 CH1 and hinge had slightly better avidity than that with the G1 isotype (hG3mG2a and hG1mG2a respectively), which correlates with the earlier finding that the native G3 isotype has slightly better avidity. As such, we decided to use that antibody (hG3mG2a) for subsequent analysis of my2F12 specificity by ELISA.

Example 4

My2F12 Specificity by ELISA

Initially, we tested the specificity of my2F12 for the LAM of various mycobacterial species on secreted LAM present in culture supernatant with the human G1 isotype variant as detector and Fab fragment of the same antibody as capture (FIG. 4C). As expected, my2F12 bound only detected LAM from slow-growing mycobacteria while the polyclonal αLAM used as a positive control bound all mycobacterial species. However, variability in signal for my2F12 binding was observed between the various slow-growing species, potentially due to variation in levels of secreted LAM because of length of time in culture and other factors. The higher signal of polyclonal αLAM is probably due to multiplicity of binding sites on the complex LAM molecule for the various antibodies present in a polyclonal preparation.

Previous results indicated that hG3mG2a would be a candidate antibody for use in a diagnostic test and we therefore tested that antibody in the same sandwich ELISA format using huG1 my2F12 as the capture. For this assay we used whole bacteria re-suspended in buffered saline (PBS) as the test antigen as we expected less variability in LAM amounts as length of time in culture is not a factor. The hG3mG2a variant showed no difference in specificity as compared to the native human isotype and the moG2a isotype used earlier for confocal IF microscopy, binding only the slow-growing mycobacteria as well as the actinomycete *T. paurometabolum* (FIG. 4D). No binding was observed to fast-growing mycobacteria as well as *E. coli* and the actinomycete *N. cyriacigeorgica*.

Example 5

Treatment of a Subject with an ABP

A subject (e.g., a human) is treated with an ABP (e.g., a my2F12 antibody disclosed herein, e.g., a monoclonal antibody comprising one or more amino acid sequences shown in Table 1) to treat a condition such as a pathogenic mycobacteria infection. In some instances, one or more additional agents are co-administered with the ABP. A subject in need of treatment can be selected or identified based on, e.g., the presence of ManLAM or mycobacteria. The identification of the subject can occur in a clinical setting, or elsewhere, e.g., in the subject's home through the subject's own use of a self-testing kit or by a third party. At time zero, a suitable first dose of ABP is administered to the subject. The ABP is formulated as described herein. After a period of time following the first dose, e.g., 7 days, 14 days, and 21 days, the subject's condition is evaluated. This measurement can be accompanied by a measurement of infection level in said subject. Other relevant criteria can also be measured. The number and strength of doses are adjusted according to the subject's needs.

While the invention has been particularly shown and described with reference to a preferred embodiment and various alternate embodiments, it will be understood by persons skilled in the relevant art that various changes in form and details can be made therein without departing from the spirit and scope of the invention.

All references, issued patents and patent applications cited within the body of the instant specification are hereby incorporated by reference in their entirety, for all purposes.

REFERENCES

1. *Global Tuberculosis Control.* 2009, WHO.
2. Boehme, C., et al., *Detection of mycobacterial lipoarabinomannan with an antigen-capture ELISA in unprocessed urine of Tanzanian patients with suspected tuberculosis.* Trans R Soc Trop Med Hyg, 2005. 99(12): p. 893-900.
3. Tessema, T. A., et al., *Diagnostic evaluation of urinary lipoarabinomannan at an Ethiopian tuberculosis centre.* Scand J Infect Dis, 2001. 33(4): p. 279-84.
4. Nigou, J., M. Gilleron, and G. Puzo, *Lipoarabinomannans: from structure to biosynthesis.* Biochimie, 2003. 85(1-2): p. 153-66.
5. *Diagnostics for Tuberculosis: Global demand and market potential.* 2006, WHO
6. Kambashi, B., et al., *Utility of nucleic acid amplification techniques for the diagnosis of pulmonary tuberculosis in sub-Saharan Africa.* Int J Tuberc Lung Dis, 2001. 5(4): p. 364-9.
7. Pai, M., et al., *Nucleic acid amplification tests in the diagnosis of tuberculous pleuritis: a systematic review and meta-analysis.* BMC Infect Dis, 2004. 4: p. 6.
8. Steingart, K. R., et al., *Sputum processing methods to improve the sensitivity of smear microscopy for tuberculosis: a systematic review.* Lancet Infect Dis, 2006. 6(10): p. 664-74.
9. Elliott, A. M., et al., *Negative sputum smear results in HIV-positive patients with pulmonary tuberculosis in Lusaka, Zambia.* Tuber Lung Dis, 1993. 74(3): p. 191-4.

10. Steingart, K. R., et al., *Commercial serological antibody detection tests for the diagnosis of pulmonary tuberculosis: a systematic review*. PLoS Med, 2007. 4(6): p. e202.
11. Pai, M., A. Zwerling, and D. Menzies, *Systematic review: T-cell-based assays for the diagnosis of latent tuberculosis infection: an update*. Ann Intern Med, 2008. 149(3): p. 177-84.
12. Cho, S. N., et al., *Production of monoclonal antibodies to lipoarabinomannan-B and use in the detection of mycobacterial antigens in sputum*. Yonsei Med J, 1990. 31(4): p. 333-8.
13. Pereira Arias-Bouda, L. M., et al., *Development of antigen detection assay for diagnosis of tuberculosis using sputum samples*. J Clin Microbiol, 2000. 38(6): p. 2278-83.
14. Araj, G. F., et al., *Improved detection of mycobacterial antigens in clinical specimens by combined enzyme-linked immunosorbent assay*. Diagn Microbiol Infect Dis, 1993. 17(2): p. 119-27.
15. Purohit, M. R., et al., *Immunohistochemical diagnosis of abdominal and lymph node tuberculosis by detecting Mycobacterium tuberculosis complex specific antigen MPT64*. Diagn Pathol, 2007. 2: p. 36.
16. Baba, K., et al., *Rapid and specific diagnosis of tuberculous pleuritis with immunohistochemistry by detecting Mycobacterium tuberculosis complex specific antigen MPT64 in patients from a HIV endemic area*. Appl Immunohistochem Mol Morphol, 2008. 16(6): p. 554-61.
17. Hamasur, B., et al., *Rapid diagnosis of tuberculosis by detection of mycobacterial lipoarabinomannan in urine*. J Microbiol Methods, 2001. 45(1): p. 41-52.
18. Ben-Selma, W., et al., *Rapid detection of Mycobacterium tuberculosis in sputum by Patho-TB kit in comparison with direct microscopy and culture*. Diagn Microbiol Infect Dis, 2009. 65(3): p. 232-5.
19. Chakraborty, N., et al., *A rapid immunochromatographic assay for the detection of Mycobacterium tuberculosis antigens in pulmonary samples from HIV seropositive patients and its comparison with conventional methods*. J Microbiol Methods, 2009. 76(1): p. 12-7.
20. Shah, M., et al., *Diagnostic accuracy of a urine lipoarabinomannan test for tuberculosis in hospitalized patients in a High HIV prevalence setting*. J Acquir Immune Defic Syndr, 2009. 52(2): p. 145-51.
21. Reither, K., et al., *Low sensitivity of a urine LAM-ELISA in the diagnosis of pulmonary tuberculosis*. BMC Infect Dis, 2009. 9: p. 141.
22. Lawn, S. D., et al., *Urine lipoarabinomannan assay for tuberculosis screening before antiretroviral therapy diagnostic yield and association with immune reconstitution disease*. Aids, 2009. 23(14): p. 1875-80.
23. Dheda, K., et al., *Clinical utility of a commercial LAM-ELISA assay for TB diagnosis in HIV-infected patients using urine and sputum samples*. PLoS One, 2010. 5(3): p. e9848.
24. Chatterjee, D., *The mycobacterial cell wall: structure, biosynthesis and sites of drug action*. Curr Opin Chem Biol, 1997. 1(4): p. 579-88.
25. Schlesinger, L. S., S. R. Hull, and T. M. Kaufman, *Binding of the terminal mannosyl units of lipoarabinomannan from a virulent strain of Mycobacterium tuberculosis to human macrophages*. J Immunol, 1994. 152(8): p. 4070-9.
26. Kang, P. B., et al., *The human macrophage mannose receptor directs Mycobacterium tuberculosis lipoarabinomannan-mediated phagosome biogenesis*. J Exp Med, 2005. 202(7): p. 987-99.
27. Torrelles, J. B., et al., *Identification of Mycobacterium tuberculosis clinical isolates with altered phagocytosis by human macrophages due to a truncated lipoarabinomannan*. J Biol Chem, 2008. 283(46): p. 31417-28.
28. Malik, Z. A., et al., *Cutting edge: Mycobacterium tuberculosis blocks Ca2+ signaling and phagosome maturation in human macrophages via specific inhibition of sphingosine kinase*. J Immunol, 2003. 170(6): p. 2811-5.
29. Thompson, C. R., et al., *Sphingosine kinase 1 (SK1) is recruited to nascent phagosomes in human macrophages: inhibition of SK1 translocation by Mycobacterium tuberculosis*. J Immunol, 2005. 174(6): p. 3551-61.
30. Vergne, I., J. Chua, and V. Deretic, *Tuberculosis toxin blocking phagosome maturation inhibits a novel Ca2+/calmodulin-PI3K hVPS34 cascade*. J Exp Med, 2003. 198 (4): p. 653-9.
31. Welin, A., et al., *Incorporation of Mycobacterium tuberculosis lipoarabinomannan into macrophage membrane rafts is a prerequisite for the phagosomal maturation block*. Infect Immun, 2008. 76(7): p. 2882-7.
32. Geijtenbeek, T. B., et al., *Mycobacteria target DC-SIGN to suppress dendritic cell function*. J Exp Med, 2003. 197 (1): p. 7-17.
33. Pathak, S. K., et al., *Mycobacterium tuberculosis lipoarabinomannan-mediated IRAK-M induction negatively regulates Toll-like receptor-dependent interleukin-12 p 40 production in macrophages*. J Biol Chem, 2005. 280(52): p. 42794-800.
34. Fujiwara, N., et al., *Production and partial characterization of anti-cord factor (trehalose-6,6'-dimycolate) IgG antibody in rabbits recognizing mycolic acid subclasses of Mycobacterium tuberculosis or Mycobacterium avium*. FEMS Immunol Med Microbiol, 1999. 24(2): p. 141-9.
35. Hamasur, B., et al., *A mycobacterial lipoarabinomannan specific monoclonal antibody and its F(ab') fragment prolong survival of mice infected with Mycobacterium tuberculosis*. Clin Exp Immunol, 2004. 138(1): p. 30-8.
36. Mehta, P. K. and G. K. Khuller, *Protective immunity to experimental tuberculosis by mannophosphoinositides of mycobacteria*. Med Microbiol Immunol, 1988. 177(5): p. 265-84.
37. Hamasur, B., et al., *Mycobacterium tuberculosis arabinomannan-protein conjugates protect against tuberculosis*. Vaccine, 2003. 21(25-26): p. 4081-93.
38. Hoogenboom, H. R., *Selecting and screening recombinant antibody libraries*. Nat Biotechnol, 2005. 23(9): p. 1105-16.

TABLE 1

| SEQ ID NO | DESCRIPTION | SEQUENCE (5'-3' FOR NUCLEOTIDE SEQUENCES) |
|---|---|---|
| 7 | my2F12 Heavy Chain CDR1 | NYAMS |
| 8 | my2F12 Heavy Chain CDR2 | TIGTTDGDIHYADSVKG |

TABLE 1 -continued

| SEQ ID NO | DESCRIPTION | SEQUENCE (5'-3' FOR NUCLEOTIDE SEQUENCES) |
|---|---|---|
| 9 | my2F12 Heavy Chain CDR3 | RFGEHFDYWGQGTLVTVS |
| 10 | Constant Heavy Chain-moG2a/moG2afull (36389.4 Da) | AKTTAPSVYPLAPVCGDTTGSSVTLGCLVKGYFPEPVTLTWNSGS LSSGVHTFPAVLQSDLYTLSSSVTVTSSTWPSQSITCNVAHPASS TKVDKKIEPRGPTIKPCPPCKCPAPNLLGGPSVFIFPPKIKDVLM ISLSPIVTCVVVDVSEDDPDVQISWFVNNVEVHTAQTQTHREDYN STLRVVSALPIQHQDWMSGKEFKCKVNNKDLPAPIERTISKPKGS VRAPQVYVLPPPEEEMTKKQVTLTCMVTDFMPEDIYVEWTNNGKT ELNYKNTEPVLDSDGSYFMYSKLRVEKKNWVERNSYSCSVVHEGL HNHHTTKSFSRTPGK |
| 11 | Constant Heavy Chain-hG1mG2a (36319.2 Da) | ASTKGPSVFPLAPSSKSTSGGTAALGCLVKDYFPEPVTVSWNSGA LTSGVHTFPAVLQSSGLYSLSSVVTVPSSSLGTQTYICNVNHKPS NTKVDKKVEPKSCDKTHTCPPCPAPNLLGGPSVFIFPPKIKDVLM ISLSPIVTCVVVDVSEDDPDVQISWFVNNVEVHTAQTQTHREDYN STLRVVSALPIQHQDWMSGKEFKCKVNNKDLPAPIERTISKPKGS VRAPQVYVLPPPEEEMTKKQVTLTCMVTDFMPEDIYVEWTNNGKT ELNYKNTEPVLDSDGSYFMYSKLRVEKKNWVERNSYSCSVVHEGL HNHHTTKSFSRTPGK |
| 12 | Constant Heavy Chain-hG3mG2a (41492.1 Da) | ASTKGPSVFPLAPCSRSTSGGTAALGCLVKDYFPEPVTVSWNSGA LTSGVHTFPAVLQSSGLYSLSSVVTVPSSSLGTQTYTCNVNHKPS NTKVDKRVELKTPLGDTTHTCPRCPEPKSCDTPPPYPRCPEPKSC DTPPPCPRCPEPKSCDTPPPCPRCPAPNLLGGPSVFIFPPKIKDV LMISLSPIVTCVVVDVSEDDPDVQISWFVNNVEVHTAQTQTHRED YNSTLRVVSALPIQHQDWMSGKEFKCKVNNKDLPAPIERTISKPK GSVRAPQVYVLPPPEEEMTKKQVTLTCMVTDFMPEDIYVEWTNNG KTELNYKNTEPVLDSDGSYFMYSKLRVEKKNWVERNSYSCSVVHE GLHNHHTTKSFSRTPGK |
| 13 | Constant Heavy Chain-huG1full (36105.9 Da) | ASTKGPSVFPLAPSSKSTSGGTAALGCLVKDYFPEPVTVSWNSGA LTSGVHTFPAVLQSSGLYSLSSVVTVPSSSLGTQTYICNVNHKPS NTKVDKKVEPKSCDKTHTCPPCPAPELLGGPSVFLFPPKPKDTLM ISRTPEVTCVVVDVSHEDPEVKFNWYVDGVEVHNAKTKPREEQYN STYRVVSVLTVLHQDWLNGKEYKCKVSNKALPAPIEKTISKAKGQ PREPQVYTLPPSRDELTKNQVSLTCLVKGFYPSDIAVEWESNGQP ENNYKTTPPVLDSDGSFFLYSKLTVDKSRWQQGNVFSCSVMHEAL HNHYTQKSLSLSPGK |
| 14 | Constant Heavy Chain-huG3full (41330.9 Da) | ASTKGPSVFPLAPCSRSTSGGTAALGCLVKDYFPEPVTVSWNSGA LTSGVHTFPAVLQSSGLYSLSSVVTVPSSSLGTQTYTCNVNHKPS NTKVDKRVELKTPLGDTTHTCPRCPEPKSCDTPPPYPRCPEPKSC DTPPPCPRCPEPKSCDTPPPCPRCPAPELLGGPSVFLFPPKPKDT LMISRTPEVTCVVVDVSHEDPEVQFKWYVDGVEVHNAKTKPREEQ FNSTFRVVSVLTVLHQDWLNGKEYKCKVSNKALPAPIEKTISKTK GQPREPQVYTLPPSREEMTKNQVSLTCLVKGFYPSDIAVEWESSG QPENNYNTTPPMLDSDGSFFLYSKLTVDKSRWQQGNIFSCSVMHE ALHNRFTQKSLSLSPGK |
| 15 | Variable Heavy Chain-VH (12823.3 Da)- for all 2F12 IgGs | QVQLVESGGGLVQPGGSLRLSCAASGFTFSNYAMSWVRQAPRRGL EWVSTIGTTDGDIHYADSVKGRFTISRDNAKNTLYLQMSSLRAED TAVYFCALRFGEHFDYWGQGTLVTVSS |
| 16 | Constant Light Chain-HuCK (11608.8 Da)- for all 2F12 IgGs except moG2afull | TVAAPSVFIFPPSDEQLKSGTASVVCLLNNFYPREAKVQWKVDNA LQSGNSQESVTEQDSKDSTYSLSSTLTLSKADYEKHKVYACEVTH QGLSSPVTKSFNRGEC |
| 17 | Constant Light Chain-MoCK (11777.8 Da)- for moG2afull IgG only | ADAAPTVSIFPPSSEQLTSGGASVVCFLNNFYPKDINVKWKIDGS ERQNGVLNSWTDQDSKDSTYSMSSTLTLTKDEYERHNSYTCEATH KTSTSPIVKSFNRNEC |
| 18 | Variable Light Chain-VL (12482.1 Da)-for for all 2F12 IgGs | DIVMTHTPLSSPVTLGQPASISCRSSQSLVHSDGNTYLSWLQQRP GQPPRLLIYKISNRFSGVPDRFSGSGAGTDFTLKISRVEAEDVGV YYCMQATQFPWTFGQGTKVEIKR |
| 19 | my2F12 Heavy Chain Variable Gene Sequence | GTGCAGCTGGTGGAGTCTGGGGGAGGCTTGGTACAGCCTGGGGGG TCCCTGAGACTCTCCTGTGCAGCCTCTGGATTCACCTTTAGCAAC TATGCCATGAGCTGGGTCCGCCAGGCTCCACGGAGGGGCCTGGAG TGGGTCTCCACTATTGGTACTACTGATGGTGACATACACTACGCA GACTCCGTTAAGGGCCGGTTCACCATCTCCAGAGACAACGCCAAG AACACACTGTATCTGCAAATGAGCAGCCTGAGAGCCGAGGACACG GCCGTATATTTCTGTGCGTTACGGTTCGGGGAGCATTTCGACTAC TGGGGCCAGGGAACCCTGGTCACCGTCTCA |

TABLE 1 -continued

| SEQ ID NO | DESCRIPTION | SEQUENCE (5'-3' FOR NUCLEOTIDE SEQUENCES) |
|---|---|---|
| 20 | my2F12 Heavy Chain CDR1 | AACTATGCCATGAGC |
| 21 | my2F12 Heavy Chain CDR2 | ACTATTGGTACTACTGATGGTGACATACACTACGCAGACTCCGTT AAGGGC |
| 22 | my2F12 Heavy Chain CDR3 | CGGTTCGGGGAGCATTTCGACTACTGGGGCCAGGGAACCCTGGTC ACCGTCTCC |
| 23 | my2F12 Light Chain Variable Gene Sequence | GATATTGTGATGACCCACACTCCACTCTCCTCACCTGTCACCCTT GGACAGCCGGCCTCCATCTCCTGCAGGTCTAGTCAAAGCCTCGTA CACAGTGATGGAAACACCTACTTGAGTTGGCTTCAGCAGAGGCCA GGCCAGCCTCCAAGACTCCTAATTTATAAGATTTCTAACCGGTTC TCTGGGGTCCCAGACAGATTCAGTGGCAGTGGGGCAGGGACAGAT TTCACACTGAAAATCAGCAGGGTGGAAGCTGAGGATGTCGGGGTT TATTACTGCATGCAAGCTACACAATTTCCGTGGACGTTCGGCCAA GGGACCAAGGTGGAAATCAAAC |
| 24 | my2F12 Light Chain CDR1 | AGGTCTAGTCAAAGCCTCGTACACAGTGATGGAAACACCTACTTG AGT |
| 25 | my2F12 Light Chain CDR2 | AAGATTTCTAACCGGTTCTCT |
| 26 | my2F12 Light Chain CDR3 | ATGCAAGCTACACAATTTCCGTGGACGTTCGGCCAAGGGACCAAG GTGGAAATCAAA |
| 27 | my2F12 Light Chain CDR1 | RSSQSLVHSDGNTYLS |
| 28 | my2F12 Light Chain CDR2 | KISNRFS |
| 29 | my2F12 Light Chain CDR3 | MQATQFPWTFGQGTKVEIK |
| 30 | my2F12 Human Light Chain Sequence-used in for all 2F12 IgGs except moG2afull DNA (663 bp) | GATATTGTGATGACCCACACTCCACTCTCCTCACCTGTCACCCTT GGACAGCCGGCCTCCATCTCCTGCAGGTCTAGTCAAAGCCTCGTA CACAGTGATGGAAACACCTACTTGAGTTGGCTTCAGCAGAGGCCA GGCCAGCCTCCAAGACTCCTAATTTATAAGATTTCTAACCGGTTC TCTGGGGTCCCAGACAGATTCAGTGGCAGTGGGGCAGGGACAGAT TTCACACTGAAAATCAGCAGGGTGGAAGCTGAGGATGTCGGGGTT TATTACTGCATGCAAGCTACACAATTTCCGTGGACGTTCGGCCAA GGGACCAAGGTGGAAATCAAACGAACTGTGGCTGCACCATCTGTC TTCATCTTCCCGCCATCTGATGAGCAGTTGAAATCTGGAACTGCC TCTGTTGTGTGCCTGCTGAATAACTTCTATCCCAGAGAGGCCAAA GTACAGTGGAAGGTGGATAACGCCCTCCAATCGGGTAACTCCCAG GAGAGTGTCACAGAGCAGGACAGCAAGGACAGCACCTACAGCCTC AGCAGCACCCTGACGCTGAGCAAAGCAGACTACGAGAAACACAAA GTCTACGCCTGCGAAGTCACCCATCAGGGCCTGAGCTCGCCCGTC ACAAAGAGCTTCAACAGGGGAGAGTGTTAATAA |
| 31 | my2F12 Human Light Chain Sequence- used in for all 2F12 IgGs except moG2afull Protein (219 a.a.) | DIVMTHTPLSSPVTLGQPASISCRSSQSLVHSDGNTYLSWLQQRP GQPPRLLIYKISNRFSGVPDRFSGSGAGTDFTLKISRVEAEDVGV YYCMQATQFPWTFGQGTKVEIKRTVAAPSVFIFPPSDEQLKSGTA SVVCLLNNFYPREAKVQWKVDNALQSGNSQESVTEQDSKDSTYSL SSTLTLSKADYEKHKVYACEVTHQGLSSPVTKSFNRGEC |
| 32 | my2F12 Human- Mouse Chimeric Light Chain Sequence-used in MOG2afull IgG only DNA (663 bp) | GATATTGTGATGACCCACACTCCACTCTCCTCACCTGTCACCCTT GGACAGCCGGCCTCCATCTCCTGCAGGTCTAGTCAAAGCCTCGTA CACAGTGATGGAAACACCTACTTGAGTTGGCTTCAGCAGAGGCCA GGCCAGCCTCCAAGACTCCTAATTTATAAGATTTCTAACCGGTTC TCTGGGGTCCCAGACAGATTCAGTGGCAGTGGGGCAGGGACAGAT TTCACACTGAAAATCAGCAGGGTGGAAGCTGAGGATGTCGGGGTT TATTACTGCATGCAAGCTACACAATTTCCGTGGACGTTCGGCCAA GGGACCAAGGTGGAAATCAAACGGGCTGATGCTGCACCAACTGTA TCCATCTTCCCACCATCCAGTGAGCAGTTAACATCTGGAGGTGCC TCAGTCGTGTGCTTCTTGAACAACTTCTACCCCAAAGACATCAAT GTCAAGTGGAAGATTGATGGCAGTGAACGACAAAATGGCGTCCTG AACAGTTGGACTGATCAGGACAGCAAAGACAGCACCTACAGCATG AGCAGCACCCTCACGTTGACCAAGGACGAGTATGAACGACATAAC AGCTATACCTGTGAGGCCACTCACAAGACATCAACTTCACCCATT GTCAAGAGCTTCAACAGGAATGAGTGTTAGTAG |

| SEQ ID NO | DESCRIPTION | SEQUENCE (5'-3' FOR NUCLEOTIDE SEQUENCES) |
|---|---|---|
| 33 | my2F12 Human-Mouse Chimeric Light Chain Sequence-used in moG2afull IgG only Protein (219 a.a.) | DIVMTHTPLSSPVTLGQPASISCRSSQSLVHSDGNTYLSWLQQRP GQPPRLLIYKISNRFSGVPDRFSGSGAGTDFTLKISRVEAEDVGV YYCMQATQFPWTFGQGTKVEIKRADAAPTVSIFPPSSEQLTSGGA SVVCFLNNFYPKDINVKWKIDGSERQNGVLNSWTDQDSKDSTYSM SSTLTLTKDEYERHNSYTCEATHKTSTSPIVKSFNRNEC |
| 34 | my2F12 Human G1 Heavy Chain sequence-used in HuG1full IgG DNA (1347 bp) | CAGGTGCAGCTGGTGGAGTCTGGGGGAGGCTTGGTACAGCCTGGG GGGTCCCTGAGACTCTCCTGTGCAGCCTCTGGATTCACCTTTAGC AACTATGCCATGAGCTGGGTCCGCCAGGCTCCACGGAGGGGGCTG GAGTGGGTCTCCACTATTGGTACTACTGATGGTGACATACACTAC GCAGACTCCGTTAAGGGCCGGTTCACCATCTCCAGAGACAACGCC AAGAACACACTGTATCTGCAAATGAGCAGCCTGAGAGCCGAGGAC ACGGCCGTATATTTCTGTGCGTTACGGTTCGGGGAGCATTTCGAC TACTGGGGCCAGGGAACCCTGGTCACCGTCTCAAGCGCCTCCACC AAGGGCCCATCGGTCTTCCCGCTAGCACCCTCCTCCAAGAGCACC TCTGGGGGCACAGCGGCCCTGGGCTGCCTGGTCAAGGACTACTTC CCCGAACCGGTGACGGTGTCGTGGAACTCAGGCGCCCTGACCAGC GGCGTCCACACCTTCCCGGCTGTCCTACAGTCCTCCGGACTCTAC TCCCTCAGCAGCGTAGTGACCGTGCCCTCCAGCAGCTTGGGCACC CAGACCTACATCTGCAACGTGAATCACAAGCCCAGCAACACCAAG GTGGACAAGAAAGTTGAGCCCAAATCTTGTGACAAAACTCACACA TGCCCACCGTGCCCAGCACCTGAACTCCTGGGGGGACCGTCAGTC TTCCTCTTCCCCCCAAAACCCAAGGACACCCTCATGATCTCCCGG ACCCCTGAGGTCACATGCGTGGTGGTGGACGTGAGCCACGAAGAC CCTGAGGTCAAGTTCAACTGGTACGTGGACGGCGTGGAGGTGCAT AATGCCAAGACAAAGCCGCGGGAGGAGCAGTACAACAGCACGTAC CGTGTGGTCAGCGTCCTCACCGTCCTGCACCAGGACTGGCTGAAT GGCAAGGAGTACAAGTGCAAGGTCTCCAACAAAGCCCTCCCAGCC CCCATCGAGAAAACCATCTCCAAAGCCAAAGGGCAGCCCCGAGAA CCACAGGTGTACACCCTGCCCCCATCCCGGGATGAGCTGACCAAG AACCAGGTCAGCCTGACCTGCCTGGTCAAAGGCTTCTATCCCAGC GACATCGCCGTGGAGTGGGAGAGCAATGGGCAGCCGGAGAACAAC TACAAGACCACGCCTCCCGTGCTGGACTCCGACGGCTCCTTCTTC CTCTACAGCAAGCTCACCGTGGACAAGAGCAGGTGGCAGCAGGGG AACGTCTTCTCATGCTCCGTGATGCATGAGGCTCTGCACAACCAC TACACGCAGAAGAGCCTCTCCCTGTCTCCGGGTAAATGATAA |
| 35 | my2F12 Human G1 Heavy Chain sequence-used in HuG1full IgG Protein (447 a.a.) | QVQLVESGGGLVQPGGSLRLSCAASGFTFSNYAMSWVRQAPRRGL EWVSTIGTTDGDIHYADSVKGRFTISRDNAKNTLYLQMSSLRAED TAVYFCALRFGEHFDYWGQGTLVTVSSASTKGPSVFPLAPSSKST SGGTAALGCLVKDYFPEPVTVSWNSGALTSGVHTFPAVLQSSGLY SLSSVVTVPSSSLGTQTYICNVNHKPSNTKVDKKVEPKSCDKTHT CPPCPAPELLGGPSVFLFPPKPKDTLMISRTPEVTCVVVDVSHED PEVKFNWYVDGVEVHNAKTKPREEQYNSTYRVVSVLTVLHQDWLN GKEYKCKVSNKALPAPIEKTISKAKGQPREPQVYTLPPSRDELTK NQVSLTCLVKGFYPSDIAVEWESNGQPENNYKTTPPVLDSDGSFF LYSICLTVDKSRWQQGNVFSCSVMHEALHNHYTQKSLSLSPGK |
| 36 | my2F12 Human G3 Heavy Chain sequence-used in HuG3full IgG DNA (1485 bp) | CAGGTGCAGCTGGTGGAGTCTGGGGGAGGCTTGGTACAGCCTGGG GGGTCCCTGAGACTCTCCTGTGCAGCCTCTGGATTCACCTTTAGC AACTATGCCATGAGCTGGGTCCGCCAGGCTCCACGGAGGGGGCTG GAGTGGGTCTCCACTATTGGTACTACTGATGGTGACATACACTAC GCAGACTCCGTTAAGGGCCGGTTCACCATCTCCAGAGACAACGCC AAGAACACACTGTATCTGCAAATGAGCAGCCTGAGAGCCGAGGAC ACGGCCGTATATTTCTGTGCGTTACGGTTCGGGGAGCATTTCGAC TACTGGGGCCAGGGAACCCTGGTCACCGTCTCAAGCGCCTCCACC AAGGGCCCATCGGTCTTCCCCCTGGCGCCCTGCTCCAGGAGCACC TCTGGGGGCACAGCGGCCCTGGGCTGCCTGGTCAAGGACTACTTC CCCGAACCGGTGACGGTGTCGTGGAACTCAGGCGCCCTGACCAGC GGCGTCCATACCTTCCCGGCTGTCCTACAGTCCTCAGGACTCTAC TCCCTCAGCAGCGTGGTGACAGTGCCCTCCAGCAGCTTGGGCACC CAGACCTACACCTGCAACGTGAATCACAAGCCCAGCAACACCAAG GTGGACAAGAGAGTTGAGCTCAAAACCCCACTTGGTGACACAACT CACACATGCCCACGGTGCCCAGAGCCCAAATCTTGTGACACACCT CCCCCGTACCCACGGTGCCCAGAGCCCAAATCTTGTGACACACCT CCCCCATGCCCACGGTGCCCAGAGCCCAAATCTTGTGACACACCT CCCCCATGCCCACGGTGCCCAGCACCTGAACTCCTGGGAGGACCG TCAGTCTTCCTCTTCCCCCCAAAACCCAAGGATACCCTTATGATT TCCCGGACCCCTGAGGTCACGTGCGTGGTGGTGGACGTGAGCCAC GAAGACCCCGAGGTCCAGTTCAAGTGGTACGTGGACGGCGTGGAG GTGCATAATGCCAAGACAAAGCCGCGGGAGGAGCAGTTCAACAGC ACGTTCCGTGTGGTCAGCGTCCTCACCGTCCTGCACCAGGACTGG CTGAACGGCAAGGAGTACAAGTGCAAGGTCTCCAACAAAGCCCTC CCAGCCCCCATCGAGAAAACCATCTCCAAAACCAAAGGACAGCCC CGAGAACCACAGGTGTACACCCTGCCCCCATCCCGGGAGGAGATG |

TABLE 1 -continued

| SEQ ID NO | DESCRIPTION | SEQUENCE (5'-3' FOR NUCLEOTIDE SEQUENCES) |
|---|---|---|
| | | ACCAAGAACCAGGTCAGCCTGACCTGCCTGGTCAAAGGCTTCTAC<br>CCCAGCGACATCGCCGTGGAGTGGGAGAGCAGCGGGCAGCCGGAG<br>AACAACTACAACACCACGCCTCCCATGCTGGACTCCGACGGCTCC<br>TTCTTCCTCTACAGCAAGCTCACCGTGGACAAGAGCAGGTGGCAG<br>CAGGGGAACATCTTCTCATGCTCCGTGATGCATGAGGCTCTGCAC<br>AACCGCTTCACGCAGAAGAGCCTCTCCCTGTCTCCGGGTAAATAG |
| 37 | my2F12 Human G3<br>Heavy Chain sequence-<br>used in HuG3full<br>IgG<br>Protein (494 a.a.) | QVQLVESGGGLVQPGGSLRLSCAASGFTFSNYAMSWVRQAPRRGL<br>EWVSTIGTTDGDIHYADSVKGRFTISRDNAKNTLYLQMSSLRAED<br>TAVYFCALRFGEHFDYWGQGTLVTVSSASTKGPSVFPLAPCSRST<br>SGGTAALGCLVKDYFPEPVTVSWNSGALTSGVHTFPAVLQSSGLY<br>SLSSVVTVPSSSLGTQTYTCNVNHKPSNTKVDKRVELKTPLGDTT<br>HTCPRCPEPKSCDTPPPYPRCPEPKSCDTPPPCPRCPEPKSCDTP<br>PPCPRCPAPELLGGPSVFLFPPKPKDTLMISRTPEVTCVVVDVSH<br>EDPEVQFKWYVDGVEVHNAKTKPREEQFNSTFRVVSVLTVLHQDW<br>LNGKEYKCKVSNKALPAPIEKTISKTKGQPREPQVYTLPPSREEM<br>TKNQVSLTCLVKGFYPSDIAVEWESSGQPENNYNTTPPMLDSDGS<br>FFLYSKLTVDKSRWQQGNIFSCSVMHEALHNRFTQKSLSLSPGK |
| 38 | my2F12 Human-<br>Mouse Chimera<br>MoG2a Heavy<br>Chain sequence<br>Type I-used in<br>MoG2a &<br>MoG2afull IgGs<br>DNA (1344 bp) | CAGGTGCAGCTGGTGGAGTCTGGGGGAGGCTTGGTACAGCCTGGG<br>GGGTCCCTGAGACTCTCCTGTGCAGCCTCTGGATTCACCTTTAGC<br>AACTATGCCATGAGCTGGGTCCGCCAGGCTCCACGGAGGGGGCTG<br>GAGTGGGTCTCCACTATTGGTACTACTGATGGTGACATACACTAC<br>GCAGACTCCGTTAAGGGCCGGTTCACCATCTCCAGAGACAACGCC<br>AAGAACACACTGTATCTGCAAATGAGCAGCCTGAGAGCCGAGGAC<br>ACGGCCGTATATTTCTGTGCGTTACGGTTCGGGGAGCATTTCGAC<br>TACTGGGGCCAGGGAACCCTGGTCACCGTCTCAAGCGCCTCCACC<br>AAGGGCCCATCGGTCTTCCCGCTAGCCCCTGTGTGTGGAGATACA<br>ACTGGCTCCTCGGTGACTCTAGGATGCCTGGTCAAGGGTTATTTC<br>CCTGAGCCAGTGACCTTGACCTGGAACTCTGGATCCCTGTCCAGT<br>GGTGTCCACACCTTCCCAGCTGTCCTGCAGTCTGACCTCTACACC<br>CTCAGCAGCTCAGTGACTGTAACCTCGAGCACCTGGCCCAGCCAG<br>TCCATCACCTGCAATGTGGCCCACCCGGCAAGCAGCACCAAGGTG<br>GACAAGAAAATTGAGCCCAGAGGGCCCACAATCAAGCCCTGTCCT<br>CCATGCAAATGCCCAGCACCTAACCTCTTGGGTGGACCATCCGTC<br>TTCATCTTCCCTCCAAAGATCAAGGATGTACTCATGATCTCCCTG<br>AGCCCCATAGTCACATGTGTGGTGGTGGATGTGAGCGAGGATGAC<br>CCAGATGTCCAGATCAGCTGGTTTGTGAACAACGTGGAAGTACAC<br>ACAGCTCAGACACAAACCCATAGAGAGGATTACAACAGTACTCTC<br>CGGGTGGTCAGTGCCCTCCCCATCCAGCACCAGGACTGGATGAGT<br>GGCAAGGAGTTCAAATGCAAGGTCAACAACAAAGACCTCCCAGCG<br>CCCATCGAGAGAACCATCTCAAAACCCAAAGGGTCAGTAAGAGCT<br>CCACAGGTATATGTCTTGCCTCCACCAGAAGAAGAGATGACTAAG<br>AAACAGGTCACTCTGACCTGCATGGTCACAGACTTCATGCCTGAA<br>GACATTTACGTGGAGTGGACCAACAACGGGAAAACAGAGCTAAAC<br>TACAAGAACACTGAACCAGTCCTGGACTCTGATGGTTCTTACTTC<br>ATGTACAGCAAGCTGAGAGTGGAAAAGAAGAACTGGGTGGAAAGA<br>AATAGCTACTCCTGTTCAGTGGTCCACGAGGGTCTGCACAATCAC<br>CACACGACTAAGAGCTTCTCCCGGACTCCGGGTAAATGA |
| 39 | my2F12 Human-<br>Mouse Chimera<br>MoG2a Heavy<br>Chain sequence<br>Type I-used in<br>MoG2a &<br>MoG2afull IgGs<br>Protein (447 a.a.) | QVQLVESGGGLVQPGGSLRLSCAASGFTFSNYAMSWVRQAPRRGL<br>EWVSTIGTTDGDIHYADSVKGRFTISRDNAKNTLYLQMSSLRAED<br>TAVYFCALRFGEHFDYWGQGTLVTVSSASTKGPSVFPLAPVCGDT<br>TGSSVTLGCLVKGYFPEPVTLTWNSGSLSSGVHTFPAVLQSDLYT<br>LSSSVTVTSSTWPSQSITCNVAHPASSTKVDKKIEPRGPTIKPCP<br>PCKCPAPNLLGGPSVFIFPPKIKDVLMISLSPIVTCVVVDVSEDD<br>PDVQISWFVNNVEVHTAQTQTHREDYNSTLRVVSALPIQHQDWMS<br>GKEFKCKVNNKDLPAPIERTISKPKGSVRAPQVYVLPPPEEEMTK<br>KQVTLTCMVTDFMPEDIYVEWTNNGKTELNYKNTEPVLDSDGSYF<br>MYSKLRVEKKNWVERNSYSCSVVHEGLHNHHTTKSFSRTPGK |
| 40 | my2F12 Human-<br>Mouse Chimera<br>MoG2a Heavy Chain<br>sequence Type II-<br>alternative usable<br>sequence for MoG2a<br>& MoG2a full IgGs<br>DNA (1344 bp) | CAGGTGCAGCTGGTGGAGTCTGGGGGAGGCTTGGTACAGCCTGGG<br>GGGTCCCTGAGACTCTCCTGTGCAGCCTCTGGATTCACCTTTAGC<br>AACTATGCCATGAGCTGGGTCCGCCAGGCTCCACGGAGGGGGCTG<br>GAGTGGGTCTCCACTATTGGTACTACTGATGGTGACATACACTAC<br>GCAGACTCCGTTAAGGGCCGGTTCACCATCTCCAGAGACAACGCC<br>AAGAACACACTGTATCTGCAAATGAGCAGCCTGAGAGCCGAGGAC<br>ACGGCCGTATATTTCTGTGCGTTACGGTTCGGGGAGCATTTCGAC<br>TACTGGGGCCAGGGAACCCTGGTCACCGTCTCAAGCGCCAAAACA<br>ACAGCCCCATCGGTCTATCCACTAGCCCCTGTGTGTGGAGATACA<br>ACTGGCTCCTCGGTGACTCTAGGATGCCTGGTCAAGGGTTATTTC<br>CCTGAGCCAGTGACCTTGACCTGGAACTCTGGATCCCTGTCCAGT<br>GGTGTCCACACCTTCCCAGCTGTCCTGCAGTCTGACCTCTACACC<br>CTCAGCAGCTCAGTGACTGTAACCTCGAGCACCTGGCCCAGCCAG<br>TCCATCACCTGCAATGTGGCCCACCCGGCAAGCAGCACCAAGGTG<br>GACAAGAAAATTGAGCCCAGAGGGCCCACAATCAAGCCCTGTCCT<br>CCATGCAAATGCCCAGCACCTAACCTCTTGGGTGGACCATCCGTC<br>TTCATCTTCCCTCCAAAGATCAAGGATGTACTCATGATCTCCCTG |

TABLE 1 -continued

| SEQ ID NO | DESCRIPTION | SEQUENCE (5'-3' FOR NUCLEOTIDE SEQUENCES) |
|---|---|---|
| | | AGCCCCATAGTCACATGTGTGGTGGTGGATGTGAGCGAGGATGAC<br>CCAGATGTCCAGATCAGCTGGTTTGTGAACAACGTGGAAGTACAC<br>ACAGCTCAGACACAAACCCATAGAGAGGATTACAACAGTACTCTC<br>CGGGTGGTCAGTGCCCTCCCCATCCAGCACCAGGACTGGATGAGT<br>GGCAAGGAGTTCAAATGCAAGGTCAACAACAAAGACCTCCCAGCG<br>CCCATCGAGAGAACCATCTCAAAACCCAAAGGGTCAGTAAGAGCT<br>CCACAGGTATATGTCTTGCCTCCACCAGAAGAAGAGATGACTAAG<br>AAACAGGTCACTCTGACCTGCATGGTCACAGACTTCATGCCTGAA<br>GACATTTACGTGGAGTGGACCAACAACGGGAAAACAGAGCTAAAC<br>TACAAGAACACTGAACCAGTCCTGGACTCTGATGGTTCTTACTTC<br>ATGTACAGCAAGCTGAGAGTGGAAAAGAAGAACTGGGTGGAAAGA<br>AATAGCTACTCCTGTTCAGTGGTCCACGAGGGTCTGCACAATCAC<br>ACACGACTAAGAGCTTCTCCCGGACTCCGGGTAAATAG |
| 41 | my2F12 Human-Mouse Chimera MoG2a Heavy Chain sequence Type II-alternative usable sequence for MoG2a & MoG2a full IgGs Protein (447 a.a.) | QVQLVESGGGLVQPGGSLRLSCAASGFTFSNYAMSWVRQAPRRGL<br>EWVSTIGTTDGDIHYADSVKGRFTISRDNAKNTLYLQMSSLRAED<br>TAVYFCALRFGEHFDYWGQGTLVTVSSAKTTAPSVYPLAPVCGDT<br>TGSSVTLGCLVKGYFPEPVTLTWNSGSLSSGVHTFPAVLQSDLYT<br>LSSSVTVTSSTWPSQSITCNVAHPASSTKVDKKIEPRGPTIKPCP<br>PCKCPAPNLLGGPSVFIFPPKIKDVLMISLSPIVTCVVVDVSEDD<br>PDVQISWFVNNVEVHTAQTQTHREDYNSTLRVVSALPIQHQDWMS<br>GKEFKCKVNNKDLPAPIERTISKPKGSVRAPQVYVLPPPEEEMTK<br>KQVTLTCMVTDFMPEDIYVEWTNNGKTELNYKNTEPVLDSDGSYF<br>MYSKLRVEKKNWVERNSYSCSVVHEGLHNHHTTKSFSRTPGK |
| 42 | my2F12 Human-Mouse Chimera hG1mG2a Heavy Chain sequence-used in hG1mG2a IgG DNA (1344 bp) | CAGGTGCAGCTGGTGGAGTCTGGGGGAGGCTTGGTACAGCCTGGG<br>GGGTCCCTGAGACTCTCCTGTGCAGCCTCTGGATTCACCTTTAGC<br>AACTATGCCATGAGCTGGGTCCGCCAGGCTCCACGGAGGGGGCTG<br>GAGTGGGTCTCCACTATTGGTACTACTGATGGTGACATACACTAC<br>GCAGACTCCGTTAAGGGCCGGTTCACCATCTCCAGAGACAACGCC<br>AAGAACACACTGTATCTGCAAATGAGCAGCCTGAGAGCCGAGGAC<br>ACGGCCGTATATTTCTGTGCGTTACGGTTCGGGGAGCATTTCGAC<br>TACTGGGGCCAGGGAACCCTGGTCACCGTCTCAAGCGCCTCCACC<br>AAGGGCCCATCGGTCTTCCCCCTGGCACCCTCCTCCAAGAGCACC<br>TCTGGGGGCACAGCGGCCCTGGGCTGCCTGGTCAAGGACTACTTC<br>CCCGAACCGGTGACGGTGTCGTGGAACTCAGGCGCCCTGACCAGC<br>GGCGTCCATACCTTCCCGGCTGTCCTACAGTCCTCAGGACTCTAC<br>TCCCTCAGCAGCGTGGTcACaGTGCCCTCCAGCAGCTTGGGCACC<br>CAGACCTACATCTGCAACGTGAATCACAAGCCCAGCAACACCAAG<br>GTGGACAAGAAAGTTGAGCCCAAATCTTGTGACAAAACTCACACA<br>TGCCCACCGTGCCCAGCACCTAACCTCTTGGGTGGACCATCCGTC<br>TTCATCTTCCCTCCAAAGATCAAGGATGTACTCATGATCTCCCTG<br>AGCCCCATAGTCACATGTGTGGTGGTGGATGTGAGCGAGGATGAC<br>CCAGATGTCCAGATCAGCTGGTTTGTGAACAACGTGGAAGTACAC<br>ACAGCTCAGACACAAACCCATAGAGAGGATTACAACAGTACTCTC<br>CGGGTGGTCAGTGCCCTCCCCATCCAGCACCAGGACTGGATGAGT<br>GGCAAGGAGTTCAAATGCAAGGTCAACAACAAAGACCTCCCAGCG<br>CCCATCGAGAGAACCATCTCAAAACCCAAAGGGTCAGTAAGAGCT<br>CCACAGGTATATGTCTTGCCTCCACCAGAAGAAGAGATGACTAAG<br>AAACAGGTCACTCTGACCTGCATGGTCACAGACTTCATGCCTGAA<br>GACATTTACGTGGAGTGGACCAACAACGGGAAAACAGAGCTAAAC<br>TACAAGAACACTGAACCAGTCCTGGACTCTGATGGTTCTTACTTC<br>ATGTACAGCAAGCTGAGAGTGGAAAAGAAGAACTGGGTGGAAAGA<br>AATAGCTACTCCTGTTCAGTGGTCCACGAGGGTCTGCACAATCAC<br>ACACGACTAAGAGCTTCTCCCGGACTCCGGGTAAATAG |
| 43 | my2F12 Human-Mouse Chimera hG1mG2a Heavy Chain sequence-used in hG1mG2a IgG Protein (447 a.a.) | QVQLVESGGGLVQPGGSLRLSCAASGFTFSNYAMSWVRQAPRRGL<br>EWVSTIGTTDGDIHYADSVKGRFTISRDNAKNTLYLQMSSLRAED<br>TAVYFCALRFGEHFDYWGQGTLVTVSSASTKGPSVFPLAPSSKST<br>SGGTAALGCLVKDYFPEPVTVSWNSGALTSGVHTFPAVLQSSGLY<br>SLSSVVTVPSSSLGTQTYICNVNHKPSNTKVDKKVEPKSCDKTHT<br>CPPCPAPNLLGGPSVFIFPPKIKDVLMISLSPIVTCVVVDVSEDD<br>PDVQISWFVNNVEVHTAQTQTHREDYNSTLRVVSALPIQHQDWMS<br>GKEFKCKVNNKDLPAPIERTISKPKGSVRAPQVYVLPPPEEEMTK<br>KQVTLTCMVTDFMPEDIYVEWTNNGKTELNYKNTEPVLDSDGSYF<br>MYSKLRVEKICNWVERNSYSCSVVHEGLHNHHTTKSFSRTPGK |
| 44 | my2F12 Human-Mouse Chimera hG3mG2a Heavy Chain sequence-used in hG3mG2aIgG DNA (1485 bp) | CAGGTGCAGCTGGTGGAGTCTGGGGGAGGCTTGGTACAGCCTGGG<br>GGGTCCCTGAGACTCTCCTGTGCAGCCTCTGGATTCACCTTTAGC<br>AACTATGCCATGAGCTGGGTCCGCCAGGCTCCACGGAGGGGGCTG<br>GAGTGGGTCTCCACTATTGGTACTACTGATGGTGACATACACTAC<br>GCAGACTCCGTTAAGGGCCGGTTCACCATCTCCAGAGACAACGCC<br>AAGAACACACTGTATCTGCAAATGAGCAGCCTGAGAGCCGAGGAC<br>ACGGCCGTATATTTCTGTGCGTTACGGTTCGGGGAGCATTTCGAC<br>TACTGGGGCCAGGGAACCCTGGTCACCGTCTCAAGCGCCTCCACC<br>AAGGGCCCATCGGTCTTCCCCCTGGCGCCCTGCTCCAGGAGCACC<br>TCTGGGGGCACAGCGGCCCTGGGCTGCCTGGTCAAGGACTACTTC<br>CCCGAACCGGTGACGGTGTCGTGGAACTCAGGCGCCCTGACCAGC |

TABLE 1 -continued

| SEQ ID NO | DESCRIPTION | SEQUENCE (5'-3' FOR NUCLEOTIDE SEQUENCES) |
|---|---|---|
| | | GGCGTCCATACCTTCCCGGCTGTCCTACAGTCCTCAGGACTCTAC<br>TCCCTCAGCAGCGTGGTCACAGTGCCCTCCAGCAGCTTGGGCACC<br>CAGACCTACACCTGCAACGTGAATCACAAGCCCAGCAACACCAAG<br>GTGGACAAGAGAGTTGAGCTCAAAACCCCACTTGGTGACACAACT<br>CACACATGCCCACGGTGCCCAGAGCCCAAATCTTGTGACACACCT<br>CCCCCGTACCCACGGTGCCCAGAGCCCAAATCTTGTGACACACCT<br>CCCCCATGCCCACGGTGCCCAGAGCCCAAATCTTGTGACACACCT<br>CCCCCATGCCCACGGTGCCCAGCACCTAACCTCTTGGGTGGACCA<br>TCCGTCTTCATCTTCCCTCCAAAGATCAAGGATGTACTCATGATC<br>TCCCTGAGCCCCATAGTCACATGTGTGGTGGTGGATGTGAGCGAG<br>GATGACCCAGATGTCCAGATCAGCTGGTTTGTGAACAACGTGGAA<br>GTACACAGCTCAGACACAAACCCATAGAGAGGATTACAACAGT<br>ACTCTCCGGGTGGTCAGTGCCCTCCCCATCCAGCACCAGGACTGG<br>ATGAGTGGCAAGGAGTTCAAATGCAAGGTCAACAACAAAGACCTC<br>CCAGCGCCCATCGAGAGAACCATCTCAAAACCCAAAGGGTCAGTA<br>AGAGCTCCACAGGTATATGTCTTGCCTCCACCAGAAGAAGAGATG<br>ACTAAGAAACAGGTCACTCTGACCTGCATGGTCACAGACTTCATG<br>CCTGAAGACATTTACGTGGAGTGGACCAACAACGGGAAAACAGAG<br>CTAAACTACAAGAACACTGAACCAGTCCTGGACTCTGATGGTTCT<br>TACTTCATGTACAGCAAGCTGAGAGTGGAAAAGAAGAACTGGGTG<br>GAAAGAAATAGCTACTCCTGTTCAGTGGTCCACGAGGGTCTGCAC<br>AATCACCACACGACTAAGAGCTTCTCCCGGACTCCGGGTAAATAG |
| 45 | my2F12 Human-<br>Mouse Chimera<br>hG3mG2a HeaVY<br>Chain sequence-<br>used in<br>hG3mG2aIgG<br>Protein (494 a.a.) | QVQLVESGGGLVQPGGSLRLSCAASGFTFSNYAMSWVRQAPRRGL<br>EWVSTIGTTDGDIHYADSVKGRFTISRDNAKNTLYLQMSSLRAED<br>TAVYFCALRFGEHFDYWGQGTLVTVSSASTKGPSVFPLAPCSRST<br>SGGTAALGCLVKDYFPEPVTVSWNSGALTSGVHTFPAVLQSSGLY<br>SLSSVVTVPSSSLGTQTYTCNVNHKPSNTKVDKRVELKTPLGDTT<br>HTCPRCPEPKSCDTPPPYPRCPEPKSCDTPPPCPRCPEPKSCDTP<br>PPCPRCPAPNLLGGPSVFIFPPKIKDVLMISLSPIVTCVVVDVSE<br>DDPDVQISWFVNNVEVHTAQTQTHREDYNSTLRVVSALPIQHQDW<br>MSGKEFKCKVNNKDLPAPIERTISKPKGSVRAPQVYVLPPPEEEM<br>TKKQVTLTCMVTDFMPEDIYVEWTNNGKTELNYKNTEPVLDSDGS<br>YFMYSICLRVEKKNWVERNSYSCSVVHEGLHNHHTTKSFSRTPGK |

Note:
For SEQ ID Nos 30-45 the DNA sequences include stop codons and bold indicates the variable region sequence.

---

The invention claimed is:

1. An isolated antigen binding protein (ABP) or fragment thereof that specifically binds to an alpha 1-2 linkage mannose cap of Mannose-Capped Lipoarabinomannan (ManLAM), wherein the ABP or fragment thereof is a recombinant chimeric ABP and comprises SEQ ID NOs: 7, 8, 9, 27, a sequence having at least 71.4% identity to SEQ ID NO:28, and a sequence having at least 94.7% identity to SEQ ID NO:29.

2. The ABP or fragment thereof of claim 1, wherein the ABP or fragment thereof comprises an amino acid sequence at least 97.4% identical to SEQ ID NO: 15 and an amino acid sequence at least 96.4% identical to SEQ ID NO: 18.

3. The ABP of claim 1, wherein the ABP or fragment thereof is produced from a cell that expresses the ABP.

4. The ABP of claim 1, wherein the ABP or fragment thereof binds to a region of ManLAM recognised by a monoclonal antibody expressed from an expression vector having ATCC deposit number PTA-12554.

5. The ABP of claim 1, wherein the ABP or fragment thereof has a binding specificity for the alpha 1-2 linkage mannose cap of ManLAM, and exhibits an equilibrium dissociation constant (Kd) of between about 2.268e-10 M and 5.133e-9 M for the alpha 1-2 linkage mannose cap of ManLAM or a Kd selected from about 2.268e-010 M, about 4.388e-010 M, about 6.380e-010 M, about 1.464e-009 M, 3.134e-009 M, or about 5.133e-009 M.

6. The ABP of claim 1, wherein:
the antigen binding protein does not substantially bind a mannose oligosaccharide, a phosphoinositol mannoside (PIM), hexose, a pentose monomer, maltotriose, fucose, rhamnose, lactose, galactose, di-arabinan, hexa-arabinan, and/or *Nocardia cyriacigeorgica;*
the cap comprises a plurality of alpha 1-2 linkages, two or more alpha 1-2 linkages, or three or more alpha 1-2 linkages; and/or
the ABP binds to an epitope Within the alpha 1-2 linkage mannose cap, optionally wherein the epitope:
(a) comprises a region within the alpha 1-2 linkage mannose cap,
(b) consists of a region within the alpha 1-2 linkage mannose cap,
(c) comprises a plurality of regions within the alpha 1-2 linkage mannose cap,
(d) consists of a plurality of regions within the alpha 1-2 linkage mannose cap,
(e) comprises the alpha 1-2 linkage mannose cap,
(f) comprises one alpha 1-2 linkage mannose cap,
(g) comprises a plurality of alpha 1-2 linkage mannose caps,
(h) comprises the alpha 1-2 linkage mannose cap and one or more additional alpha 1-2 linkage mannose caps,
(i) comprises the alpha 1-2 linkage mannose cap and two or more additional alpha 1-2 linkage mannose caps,
(j) comprises the alpha 1-2 linkage mannose cap and three or more additional alpha linkage mannose caps, and/or
(k) consists of the alpha 1-2 linkage mannose cap.

7. The ABP of claim 1, wherein:
the antigen binding protein is an antibody or fragment thereof, wherein the antigen binding protein is any of: a monoclonal antibody, a veneered antibody, a CDR-grafted antibody, a variable region fragment, a single domain antibody, a single-chain Fv antibody, a Fab antibody, a Fab' antibody, a (Fab')$_2$, antibody; the isotype is IgG1, IgG2, or IgG3; and/or
the antigen binding protein is an antibody comprising at least one mutation in the constant region.

8. A pharmaceutical composition comprising at least one ABP according to claim 1, and a pharmaceutically acceptable excipient.

9. An immunoassay device for detecting the presence or absence of a pathogenic mycobacteria in a sample, the device comprising: the ABP according to claim 1 immobilized on a solid support.

10. A kit for detecting a pathogenic mycobacteria infection in a sample, the kit comprising the ABP of claim 1 in an amount effective to diagnose the infection, optionally
(a) further comprising a container containing the antigen binding protein in a formulation and instructions for use;
(b) wherein the ABP consists of the ABP of claim 1;
(c) wherein the formulation is present in a vial or an injectable syringe;
(d) wherein the antigen binding protein is bound to an array;
(e) wherein the antigen binding protein is bound to a lateral-flow type test;
(f) wherein the kit is used in an enzyme-linked immunosorbent assay (ELISA);
(g) wherein the kit comprises instructions for determining whether the sample contains pathogenic mycobacteria;
(h) wherein the kit comprises an agent suitable for detecting the binding between the antigen binding protein and ManLAM;
(i) wherein the ABP is immobilized on a solid support; and/or
(j) wherein the kit comprises a detectable label.

11. A solid support linked to the ABP of claim 1.

12. The ABP of claim 1, wherein the ABP or fragment thereof is capable of competitively inhibiting specific binding to the alpha 1-2 linkage mannose cap of ManLAM, or binding by the ABP of claim 4.

13. An isolated antigen binding protein (ABP) or fragment thereof that specifically binds to an alpha 1-2 linkage mannose cap of Mannose-Capped Lipoarabinomannan (ManLAM), wherein the ABP or fragment thereof is a recombinant chimeric ABP and comprises a polypeptide having an amino acid sequence at least 97.4% identical to SEQ ID NO: 15 and an amino acid sequence at least 96.4% identical to SEQ ID NO: 18.

* * * * *

SEQUENCE LISTING

<160> NUMBER OF SEQ ID NOS: 45

<210> SEQ ID NO 1
<211> LENGTH: 19
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 1
cggatctcta gcgaattcc                                                    19

<210> SEQ ID NO 2
<211> LENGTH: 39
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 2
ccacccaaga ggttaggtgc tgggcacggt gggcatgtg                              39

<210> SEQ ID NO 3
<211> LENGTH: 41
<212> TYPE: DNA
<213> ORGANISM: Artificial Sequence

```
<220> FEATURE:
<223> OTHER INFORMATION: Description of Artificial Sequence: Synthetic
      primer

<400> SEQUENCE: 3
ccacccaaga ggttaggtgc tgggcaccgt gggcatgggg g                    41

<210> SEQ ID NO 4
<211> LENGTH: 39
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 4
cacatgccca ccgtgcccag cacctaacct cttgggtgg                      39

<210> SEQ ID NO 5
<211> LENGTH: 41
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 5
cccccatgcc cacggtgccc agcacctaac ctcttgggtg g                   41

<210> SEQ ID NO 6
<211> LENGTH: 39
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 6
atccagcttc tagactattt acccggagtc cgggagaag                      39

<210> SEQ ID NO 7
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 7

Asn Tyr Ala Met Ser
1               5

<210> SEQ ID NO 8
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 8

Thr Ile Gly Thr Thr Asp Gly Asp Ile His Tyr Ala Asp Ser Val Lys
1               5                   10                  15

Gly
```

```
<210> SEQ ID NO 9
<211> LENGTH: 18
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 9

Arg Phe Gly Glu His Phe Asp Tyr Trp Gly Gln Gly Thr Leu Val Thr
1               5                   10                  15

Val Ser

<210> SEQ ID NO 10
<211> LENGTH: 330
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 10

Ala Lys Thr Thr Ala Pro Ser Val Tyr Pro Leu Ala Pro Val Cys Gly
1               5                   10                  15

Asp Thr Thr Gly Ser Ser Val Thr Leu Gly Cys Leu Val Lys Gly Tyr
                20                  25                  30

Phe Pro Glu Pro Val Thr Leu Thr Trp Asn Ser Gly Ser Leu Ser Ser
            35                  40                  45

Gly Val His Thr Phe Pro Ala Val Leu Gln Ser Asp Leu Tyr Thr Leu
        50                  55                  60

Ser Ser Ser Val Thr Val Thr Ser Ser Thr Trp Pro Ser Gln Ser Ile
65                  70                  75                  80

Thr Cys Asn Val Ala His Pro Ala Ser Ser Thr Lys Val Asp Lys Lys
                85                  90                  95

Ile Glu Pro Arg Gly Pro Thr Ile Lys Pro Cys Pro Pro Cys Lys Cys
                100                 105                 110

Pro Ala Pro Asn Leu Leu Gly Gly Pro Ser Val Phe Ile Phe Pro Pro
            115                 120                 125

Lys Ile Lys Asp Val Leu Met Ile Ser Leu Ser Pro Ile Val Thr Cys
130                 135                 140

Val Val Val Asp Val Ser Glu Asp Asp Pro Asp Val Gln Ile Ser Trp
145                 150                 155                 160

Phe Val Asn Asn Val Glu Val His Thr Ala Gln Thr Gln Thr His Arg
                165                 170                 175

Glu Asp Tyr Asn Ser Thr Leu Arg Val Val Ser Ala Leu Pro Ile Gln
            180                 185                 190

His Gln Asp Trp Met Ser Gly Lys Glu Phe Lys Cys Lys Val Asn Asn
        195                 200                 205

Lys Asp Leu Pro Ala Pro Ile Glu Arg Thr Ile Ser Lys Pro Lys Gly
    210                 215                 220

Ser Val Arg Ala Pro Gln Val Tyr Val Leu Pro Pro Pro Glu Glu Glu
225                 230                 235                 240

Met Thr Lys Lys Gln Val Thr Leu Thr Cys Met Val Thr Asp Phe Met
                245                 250                 255

Pro Glu Asp Ile Tyr Val Glu Trp Thr Asn Asn Gly Lys Thr Glu Leu
            260                 265                 270

Asn Tyr Lys Asn Thr Glu Pro Val Leu Asp Ser Asp Gly Ser Tyr Phe
        275                 280                 285
```

Met Tyr Ser Lys Leu Arg Val Glu Lys Lys Asn Trp Val Glu Arg Asn
            290                 295                 300

Ser Tyr Ser Cys Ser Val Val His Glu Gly Leu His Asn His His Thr
305                 310                 315                 320

Thr Lys Ser Phe Ser Arg Thr Pro Gly Lys
                325                 330

<210> SEQ ID NO 11
<211> LENGTH: 330
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 11

Ala Ser Thr Lys Gly Pro Ser Val Phe Pro Leu Ala Pro Ser Ser Lys
1               5                   10                  15

Ser Thr Ser Gly Gly Thr Ala Ala Leu Gly Cys Leu Val Lys Asp Tyr
                20                  25                  30

Phe Pro Glu Pro Val Thr Val Ser Trp Asn Ser Gly Ala Leu Thr Ser
            35                  40                  45

Gly Val His Thr Phe Pro Ala Val Leu Gln Ser Ser Gly Leu Tyr Ser
        50                  55                  60

Leu Ser Ser Val Val Thr Val Pro Ser Ser Leu Gly Thr Gln Thr
65                  70                  75                  80

Tyr Ile Cys Asn Val Asn His Lys Pro Ser Asn Thr Lys Val Asp Lys
                85                  90                  95

Lys Val Glu Pro Lys Ser Cys Asp Lys Thr His Thr Cys Pro Pro Cys
            100                 105                 110

Pro Ala Pro Asn Leu Leu Gly Gly Pro Ser Val Phe Ile Phe Pro Pro
        115                 120                 125

Lys Ile Lys Asp Val Leu Met Ile Ser Leu Ser Pro Ile Val Thr Cys
130                 135                 140

Val Val Val Asp Val Ser Glu Asp Asp Pro Asp Val Gln Ile Ser Trp
145                 150                 155                 160

Phe Val Asn Asn Val Glu Val His Thr Ala Gln Thr Gln Thr His Arg
                165                 170                 175

Glu Asp Tyr Asn Ser Thr Leu Arg Val Val Ser Ala Leu Pro Ile Gln
            180                 185                 190

His Gln Asp Trp Met Ser Gly Lys Glu Phe Lys Cys Lys Val Asn Asn
        195                 200                 205

Lys Asp Leu Pro Ala Pro Ile Glu Arg Thr Ile Ser Lys Pro Lys Gly
    210                 215                 220

Ser Val Arg Ala Pro Gln Val Tyr Val Leu Pro Pro Pro Glu Glu Glu
225                 230                 235                 240

Met Thr Lys Lys Gln Val Thr Leu Thr Cys Met Val Thr Asp Phe Met
                245                 250                 255

Pro Glu Asp Ile Tyr Val Glu Trp Thr Asn Asn Gly Lys Thr Glu Leu
            260                 265                 270

Asn Tyr Lys Asn Thr Glu Pro Val Leu Asp Ser Asp Gly Ser Tyr Phe
        275                 280                 285

Met Tyr Ser Lys Leu Arg Val Glu Lys Lys Asn Trp Val Glu Arg Asn
    290                 295                 300

```
Ser Tyr Ser Cys Ser Val Val His Glu Gly Leu His Asn His His Thr
305                 310                 315                 320

Thr Lys Ser Phe Ser Arg Thr Pro Gly Lys
                325                 330

<210> SEQ ID NO 12
<211> LENGTH: 377
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 12

Ala Ser Thr Lys Gly Pro Ser Val Phe Pro Leu Ala Pro Cys Ser Arg
1               5                   10                  15

Ser Thr Ser Gly Gly Thr Ala Ala Leu Gly Cys Leu Val Lys Asp Tyr
                20                  25                  30

Phe Pro Glu Pro Val Thr Val Ser Trp Asn Ser Gly Ala Leu Thr Ser
            35                  40                  45

Gly Val His Thr Phe Pro Ala Val Leu Gln Ser Ser Gly Leu Tyr Ser
    50                  55                  60

Leu Ser Ser Val Val Thr Val Pro Ser Ser Ser Leu Gly Thr Gln Thr
65                  70                  75                  80

Tyr Thr Cys Asn Val Asn His Lys Pro Ser Asn Thr Lys Val Asp Lys
                85                  90                  95

Arg Val Glu Leu Lys Thr Pro Leu Gly Asp Thr Thr His Thr Cys Pro
            100                 105                 110

Arg Cys Pro Glu Pro Lys Ser Cys Asp Thr Pro Pro Pro Tyr Pro Arg
    115                 120                 125

Cys Pro Glu Pro Lys Ser Cys Asp Thr Pro Pro Pro Cys Pro Arg Cys
130                 135                 140

Pro Glu Pro Lys Ser Cys Asp Thr Pro Pro Pro Cys Pro Arg Cys Pro
145                 150                 155                 160

Ala Pro Asn Leu Leu Gly Gly Pro Ser Val Phe Ile Phe Pro Pro Lys
                165                 170                 175

Ile Lys Asp Val Leu Met Ile Ser Leu Ser Pro Ile Val Thr Cys Val
            180                 185                 190

Val Val Asp Val Ser Glu Asp Asp Pro Asp Val Gln Ile Ser Trp Phe
    195                 200                 205

Val Asn Asn Val Glu Val His Thr Ala Gln Thr Gln Thr His Arg Glu
210                 215                 220

Asp Tyr Asn Ser Thr Leu Arg Val Val Ser Ala Leu Pro Ile Gln His
225                 230                 235                 240

Gln Asp Trp Met Ser Gly Lys Glu Phe Lys Cys Lys Val Asn Asn Lys
                245                 250                 255

Asp Leu Pro Ala Pro Ile Glu Arg Thr Ile Ser Lys Pro Lys Gly Ser
            260                 265                 270

Val Arg Ala Pro Gln Val Tyr Val Leu Pro Pro Pro Glu Glu Glu Met
    275                 280                 285

Thr Lys Lys Gln Val Thr Leu Thr Cys Met Val Thr Asp Phe Met Pro
290                 295                 300

Glu Asp Ile Tyr Val Glu Trp Thr Asn Asn Gly Lys Thr Glu Leu Asn
305                 310                 315                 320
```

Tyr Lys Asn Thr Glu Pro Val Leu Asp Ser Asp Gly Ser Tyr Phe Met
                325                 330                 335

Tyr Ser Lys Leu Arg Val Glu Lys Lys Asn Trp Val Glu Arg Asn Ser
            340                 345                 350

Tyr Ser Cys Ser Val Val His Glu Gly Leu His Asn His His Thr Thr
            355                 360                 365

Lys Ser Phe Ser Arg Thr Pro Gly Lys
    370                 375

<210> SEQ ID NO 13
<211> LENGTH: 330
<212> TYPE: PRT
<213> ORGANISM: Homo sapiens

<400> SEQUENCE: 13

Ala Ser Thr Lys Gly Pro Ser Val Phe Pro Leu Ala Pro Ser Ser Lys
1               5                   10                  15

Ser Thr Ser Gly Gly Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Ser
    50                  55                  60

Leu Ser Ser Val Val Thr Val Pro Ser Ser Ser Leu Gly Thr Gln Thr
65                  70                  75                  80

Tyr Ile Cys Asn Val Asn His Lys Pro Ser Asn Thr Lys Val Asp Lys
                85                  90                  95

Lys Val Glu Pro Lys Ser Cys Asp Lys Thr His Thr Cys Pro Pro Cys
            100                 105                 110

Pro Ala Pro Glu Leu Leu Gly Gly Pro Ser Val Phe Leu Phe Pro Pro
        115                 120                 125

Lys Pro Lys Asp Thr Leu Met Ile Ser Arg Thr Pro Glu Val Thr Cys
    130                 135                 140

Val Val Val Asp Val Ser His Glu Asp Pro Glu Val Lys Phe Asn Trp
145                 150                 155                 160

Tyr Val Asp Gly Val Glu Val His Asn Ala Lys Thr Lys Pro Arg Glu
                165                 170                 175

Glu Gln Tyr Asn Ser Thr Tyr Arg Val Val Ser Val Leu Thr Val Leu
            180                 185                 190

His Gln Asp Trp Leu Asn Gly Lys Glu Tyr Lys Cys Lys Val Ser Asn
        195                 200                 205

Lys Ala Leu Pro Ala Pro Ile Glu Lys Thr Ile Ser Lys Ala Lys Gly
    210                 215                 220

Gln Pro Arg Glu Pro Gln Val Tyr Thr Leu Pro Pro Ser Arg Asp Glu
225                 230                 235                 240

Leu Thr Lys Asn Gln Val Ser Leu Thr Cys Leu Val Lys Gly Phe Tyr
                245                 250                 255

Pro Ser Asp Ile Ala Val Glu Trp Glu Ser Asn Gly Gln Pro Glu Asn
            260                 265                 270

Asn Tyr Lys Thr Thr Pro Pro Val Leu Asp Ser Asp Gly Ser Phe Phe
        275                 280                 285

Leu Tyr Ser Lys Leu Thr Val Asp Lys Ser Arg Trp Gln Gln Gly Asn
    290                 295                 300

Val Phe Ser Cys Ser Val Met His Glu Ala Leu His Asn His Tyr Thr

```
                    305                 310                 315                 320
Gln Lys Ser Leu Ser Leu Ser Pro Gly Lys
                325                 330

<210> SEQ ID NO 14
<211> LENGTH: 377
<212> TYPE: PRT
<213> ORGANISM: Homo sapiens

<400> SEQUENCE: 14

Ala Ser Thr Lys Gly Pro Ser Val Phe Pro Leu Ala Pro Cys Ser Arg
1               5                   10                  15

Ser Thr Ser Gly Gly Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Ser
    50                  55                  60

Leu Ser Ser Val Val Thr Val Pro Ser Ser Ser Leu Gly Thr Gln Thr
65                  70                  75                  80

Tyr Thr Cys Asn Val Asn His Lys Pro Ser Asn Thr Lys Val Asp Lys
                85                  90                  95

Arg Val Glu Leu Lys Thr Pro Leu Gly Asp Thr Thr His Thr Cys Pro
            100                 105                 110

Arg Cys Pro Glu Pro Lys Ser Cys Asp Thr Pro Pro Pro Cys Pro Arg
        115                 120                 125

Cys Pro Glu Pro Lys Ser Cys Asp Thr Pro Pro Pro Cys Pro Arg Cys
    130                 135                 140

Pro Glu Pro Lys Ser Cys Asp Thr Pro Pro Pro Cys Pro Arg Cys Pro
145                 150                 155                 160

Ala Pro Glu Leu Leu Gly Gly Pro Ser Val Phe Leu Phe Pro Pro Lys
                165                 170                 175

Pro Lys Asp Thr Leu Met Ile Ser Arg Thr Pro Glu Val Thr Cys Val
            180                 185                 190

Val Val Asp Val Ser His Glu Asp Pro Glu Val Gln Phe Lys Trp Tyr
        195                 200                 205

Val Asp Gly Val Glu Val His Asn Ala Lys Thr Lys Pro Arg Glu Glu
    210                 215                 220

Gln Phe Asn Ser Thr Phe Arg Val Val Ser Val Leu Thr Val Leu His
225                 230                 235                 240

Gln Asp Trp Leu Asn Gly Lys Glu Tyr Lys Cys Lys Val Ser Asn Lys
                245                 250                 255

Ala Leu Pro Ala Pro Ile Glu Lys Thr Ile Ser Lys Thr Lys Gly Gln
            260                 265                 270

Pro Arg Glu Pro Gln Val Tyr Thr Leu Pro Pro Ser Arg Glu Glu Met
        275                 280                 285

Thr Lys Asn Gln Val Ser Leu Thr Cys Leu Val Lys Gly Phe Tyr Pro
    290                 295                 300

Ser Asp Ile Ala Val Glu Trp Glu Ser Ser Gly Gln Pro Glu Asn Asn
305                 310                 315                 320

Tyr Asn Thr Thr Pro Pro Met Leu Asp Ser Asp Gly Ser Phe Phe Leu
                325                 330                 335

Tyr Ser Lys Leu Thr Val Asp Lys Ser Arg Trp Gln Gln Gly Asn Ile
            340                 345                 350
```

```
Phe Ser Cys Ser Val Met His Glu Ala Leu His Asn Arg Phe Thr Gln
            355                 360                 365
Lys Ser Leu Ser Leu Ser Pro Gly Lys
    370                 375

<210> SEQ ID NO 15
<211> LENGTH: 117
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 15

Gln Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Asn Tyr
            20                  25                  30

Ala Met Ser Trp Val Arg Gln Ala Pro Arg Arg Gly Leu Glu Trp Val
        35                  40                  45

Ser Thr Ile Gly Thr Thr Asp Gly Asp Ile His Tyr Ala Asp Ser Val
    50                  55                  60

Lys Gly Arg Phe Thr Ile Ser Arg Asp Asn Ala Lys Asn Thr Leu Tyr
65                  70                  75                  80

Leu Gln Met Ser Ser Leu Arg Ala Glu Asp Thr Ala Val Tyr Phe Cys
                85                  90                  95

Ala Leu Arg Phe Gly Glu His Phe Asp Tyr Trp Gly Gln Gly Thr Leu
            100                 105                 110

Val Thr Val Ser Ser
        115

<210> SEQ ID NO 16
<211> LENGTH: 106
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 16

Thr Val Ala Ala Pro Ser Val Phe Ile Phe Pro Pro Ser Asp Glu Gln
1               5                   10                  15

Leu Lys Ser Gly Thr Ala Ser Val Val Cys Leu Leu Asn Asn Phe Tyr
            20                  25                  30

Pro Arg Glu Ala Lys Val Gln Trp Lys Val Asp Asn Ala Leu Gln Ser
        35                  40                  45

Gly Asn Ser Gln Glu Ser Val Thr Glu Gln Asp Ser Lys Asp Ser Thr
    50                  55                  60

Tyr Ser Leu Ser Ser Thr Leu Thr Leu Ser Lys Ala Asp Tyr Glu Lys
65                  70                  75                  80

His Lys Val Tyr Ala Cys Glu Val Thr His Gln Gly Leu Ser Ser Pro
                85                  90                  95

Val Thr Lys Ser Phe Asn Arg Gly Glu Cys
            100                 105

<210> SEQ ID NO 17
<211> LENGTH: 106
<212> TYPE: PRT
<213> ORGANISM: Artificial Sequence
<220> FEATURE:
```

<223> OTHER INFORMATION: Description of Artificial Sequence: Synthetic
polypeptide

<400> SEQUENCE: 17

```
Ala Asp Ala Ala Pro Thr Val Ser Ile Phe Pro Pro Ser Ser Glu Gln
1               5                   10                  15

Leu Thr Ser Gly Gly Ala Ser Val Val Cys Phe Leu Asn Asn Phe Tyr
            20                  25                  30

Pro Lys Asp Ile Asn Val Lys Trp Lys Ile Asp Gly Ser Glu Arg Gln
        35                  40                  45

Asn Gly Val Leu Asn Ser Trp Thr Asp Gln Asp Ser Lys Asp Ser Thr
    50                  55                  60

Tyr Ser Met Ser Ser Thr Leu Thr Leu Thr Lys Asp Glu Tyr Glu Arg
65                  70                  75                  80

His Asn Ser Tyr Thr Cys Glu Ala Thr His Lys Thr Ser Thr Ser Pro
                85                  90                  95

Ile Val Lys Ser Phe Asn Arg Asn Glu Cys
            100                 105
```

<210> SEQ ID NO 18
<211> LENGTH: 113
<212> TYPE: PRT
<213> ORGANISM: Artificial Sequence
<220> FEATURE:
<223> OTHER INFORMATION: Description of Artificial Sequence: Synthetic
polypeptide

<400> SEQUENCE: 18

```
Asp Ile Val Met Thr His Thr Pro Leu Ser Ser Pro Val Thr Leu Gly
1               5                   10                  15

Gln Pro Ala Ser Ile Ser Cys Arg Ser Ser Gln Ser Leu Val His Ser
            20                  25                  30

Asp Gly Asn Thr Tyr Leu Ser Trp Leu Gln Gln Arg Pro Gly Gln Pro
        35                  40                  45

Pro Arg Leu Leu Ile Tyr Lys Ile Ser Asn Arg Phe Ser Gly Val Pro
    50                  55                  60

Asp Arg Phe Ser Gly Ser Gly Ala Gly Thr Asp Phe Thr Leu Lys Ile
65                  70                  75                  80

Ser Arg Val Glu Ala Glu Asp Val Gly Val Tyr Tyr Cys Met Gln Ala
                85                  90                  95

Thr Gln Phe Pro Trp Thr Phe Gly Gln Gly Thr Lys Val Glu Ile Lys
            100                 105                 110

Arg
```

<210> SEQ ID NO 19
<211> LENGTH: 345
<212> TYPE: DNA
<213> ORGANISM: Artificial Sequence
<220> FEATURE:
<223> OTHER INFORMATION: Description of Artificial Sequence: Synthetic
polynucleotide

<400> SEQUENCE: 19

```
gtgcagctgg tggagtctgg gggaggcttg gtacagcctg ggggtccct gagactctcc      60 tgtgcagcct ctggattcac ctttagcaac tatgccatga gctgggtccg ccaggctcca    120 cggaggggc tggagtgggt ctccactatt ggtactactg atggtgacat acactacgca    180
gactccgtta agggccggtt caccatctcc agagacaacg ccaagaacac actgtatctg    240
```
caaatgagca gcctgagagc cgaggacacg gccgtatatt tctgtgcgtt acggttcggg    300
gagcatttcg actactgggg ccagggaacc ctggtcaccg tctca    345

<210> SEQ ID NO 20
<211> LENGTH: 15
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 20
aactatgcca tgagc    15

<210> SEQ ID NO 21
<211> LENGTH: 51
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 21
actattggta ctactgatgg tgacatacac tacgcagact ccgttaaggg c    51

<210> SEQ ID NO 22
<211> LENGTH: 54
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 22
cggttcgggg agcatttcga ctactggggc cagggaaccc tggtcaccgt ctcc    54

<210> SEQ ID NO 23
<211> LENGTH: 337
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 23
gatattgtga tgacccacac tccactctcc tcacctgtca cccttggaca gccggcctcc    60
atctcctgca ggtctagtca aagcctcgta cacagtgatg gaaacaccta cttgagttgg    120
cttcagcaga ggccaggcca gcctccaaga ctcctaattt ataagatttc taaccggttc    180
tctggggtcc cagacagatt cagtggcagt ggggcaggga cagatttcac actgaaaatc    240
agcagggtgg aagctgagga tgtcggggtt tattactgca tgcaagctac acaatttccg    300
tggacgttcg gccaagggac caaggtggaa atcaaac    337

<210> SEQ ID NO 24
<211> LENGTH: 48
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 24
aggtctagtc aaagcctcgt acacagtgat ggaaacacct acttgagt    48

<210> SEQ ID NO 25
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 25
aagatttcta accggttctc t                                              21

<210> SEQ ID NO 26
<211> LENGTH: 57
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 26
atgcaagcta cacaatttcc gtggacgttc ggccaaggga ccaaggtgga aatcaaa       57

<210> SEQ ID NO 27
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 27

Arg Ser Ser Gln Ser Leu Val His Ser Asp Gly Asn Thr Tyr Leu Ser
1               5                   10                  15

<210> SEQ ID NO 28
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 28

Lys Ile Ser Asn Arg Phe Ser
1               5

<210> SEQ ID NO 29
<211> LENGTH: 19
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 29

Met Gln Ala Thr Gln Phe Pro Trp Thr Phe Gly Gln Gly Thr Lys Val
1               5                   10                  15

Glu Ile Lys

<210> SEQ ID NO 30
<211> LENGTH: 663
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 30

```
gatattgtga tgacccacac tccactctcc tcacctgtca cccttggaca gccggcctcc      60
atctcctgca ggtctagtca aagcctcgta cacagtgatg gaaacaccta cttgagttgg     120
cttcagcaga ggccaggcca gcctccaaga ctcctaattt ataagatttc taaccggttc     180
tctggggtcc cagacagatt cagtggcagt ggggcaggga cagatttcac actgaaaatc     240
agcagggtgg aagctgagga tgtcggggtt tattactgca tgcaagctac acaatttccg     300
tggacgttcg gccaagggac caaggtggaa atcaaacgaa ctgtggctgc accatctgtc     360
ttcatcttcc cgccatctga tgagcagttg aaatctggaa ctgcctctgt tgtgtgcctg     420
ctgaataact tctatcccag agaggccaaa gtacagtgga aggtggataa cgccctccaa     480
tcgggtaact cccaggagag tgtcacagag caggacagca aggacagcac ctacagcctc     540
agcagcaccc tgacgctgag caaagcagac tacgagaaac acaaagtcta cgcctgcgaa     600
gtcacccatc agggcctgag ctcgcccgtc acaaagagct tcaacagggg agagtgttaa     660
taa                                                                    663
```

<210> SEQ ID NO 31
<211> LENGTH: 219
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 31

```
Asp Ile Val Met Thr His Thr Pro Leu Ser Ser Pro Val Thr Leu Gly
1               5                   10                  15

Gln Pro Ala Ser Ile Ser Cys Arg Ser Ser Gln Ser Leu Val His Ser
            20                  25                  30

Asp Gly Asn Thr Tyr Leu Ser Trp Leu Gln Gln Arg Pro Gly Gln Pro
        35                  40                  45

Pro Arg Leu Leu Ile Tyr Lys Ile Ser Asn Arg Phe Ser Gly Val Pro
    50                  55                  60

Asp Arg Phe Ser Gly Ser Gly Ala Gly Thr Asp Phe Thr Leu Lys Ile
65                  70                  75                  80

Ser Arg Val Glu Ala Glu Asp Val Gly Val Tyr Tyr Cys Met Gln Ala
                85                  90                  95

Thr Gln Phe Pro Trp Thr Phe Gly Gln Gly Thr Lys Val Glu Ile Lys
            100                 105                 110

Arg Thr Val Ala Ala Pro Ser Val Phe Ile Phe Pro Pro Ser Asp Glu
        115                 120                 125

Gln Leu Lys Ser Gly Thr Ala Ser Val Val Cys Leu Leu Asn Asn Phe
    130                 135                 140

Tyr Pro Arg Glu Ala Lys Val Gln Trp Lys Val Asp Asn Ala Leu Gln
145                 150                 155                 160

Ser Gly Asn Ser Gln Glu Ser Val Thr Glu Gln Asp Ser Lys Asp Ser
                165                 170                 175

Thr Tyr Ser Leu Ser Ser Thr Leu Thr Leu Ser Lys Ala Asp Tyr Glu
            180                 185                 190

Lys His Lys Val Tyr Ala Cys Glu Val Thr His Gln Gly Leu Ser Ser
        195                 200                 205

Pro Val Thr Lys Ser Phe Asn Arg Gly Glu Cys
    210                 215
```

<210> SEQ ID NO 32
<211> LENGTH: 663
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 32

```
gatattgtga tgacccacac tccactctcc tcacctgtca cccttggaca gccggcctcc      60
atctcctgca ggtctagtca aagcctcgta cacagtgatg aaacaccta cttgagttgg     120
cttcagcaga ggccaggcca gcctccaaga ctcctaattt ataagatttc taaccggttc     180
tctggggtcc cagacagatt cagtggcagt ggggcaggga cagatttcac actgaaaatc     240
agcagggtgg aagctgagga tgtcggggtt tattactgca tgcaagctac acaatttccg     300
tggacgttcg gccaagggac caaggtggaa atcaaacggg ctgatgctgc accaactgta     360
tccatcttcc caccatccag tgagcagtta acatctggag gtgcctcagt cgtgtgcttc     420
ttgaacaact tctacccaaa agacatcaat gtcaagtgga gattgatgg cagtgaacga     480
caaaatggcg tcctgaacag ttggactgat caggacagca agacagcac ctacagcatg     540
agcagcaccc tcacgttgac caaggacgag tatgaacgac ataacagcta cctgtgag     600
gccactcaca gacatcaac ttcacccatt gtcaagagct caacaggaa tgagtgttag     660
tag                                                                 663
```

<210> SEQ ID NO 33
<211> LENGTH: 219
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 33

```
Asp Ile Val Met Thr His Thr Pro Leu Ser Ser Pro Val Thr Leu Gly
  1               5                  10                  15

Gln Pro Ala Ser Ile Ser Cys Arg Ser Ser Gln Ser Leu Val His Ser
             20                  25                  30

Asp Gly Asn Thr Tyr Leu Ser Trp Leu Gln Gln Arg Pro Gly Gln Pro
         35                  40                  45

Pro Arg Leu Leu Ile Tyr Lys Ile Ser Asn Arg Phe Ser Gly Val Pro
     50                  55                  60

Asp Arg Phe Ser Gly Ser Gly Ala Gly Thr Asp Phe Thr Leu Lys Ile
 65                  70                  75                  80

Ser Arg Val Glu Ala Glu Asp Val Gly Val Tyr Tyr Cys Met Gln Ala
                 85                  90                  95

Thr Gln Phe Pro Trp Thr Phe Gly Gln Gly Thr Lys Val Glu Ile Lys
            100                 105                 110

Arg Ala Asp Ala Ala Pro Thr Val Ser Ile Phe Pro Pro Ser Ser Glu
        115                 120                 125

Gln Leu Thr Ser Gly Gly Ala Ser Val Val Cys Phe Leu Asn Asn Phe
    130                 135                 140

Tyr Pro Lys Asp Ile Asn Val Lys Trp Lys Ile Asp Gly Ser Glu Arg
145                 150                 155                 160

Gln Asn Gly Val Leu Asn Ser Trp Thr Asp Gln Asp Ser Lys Asp Ser
                165                 170                 175
```

Thr Tyr Ser Met Ser Ser Thr Leu Thr Leu Thr Lys Asp Glu Tyr Glu
            180                 185                 190

Arg His Asn Ser Tyr Thr Cys Glu Ala Thr His Lys Thr Ser Thr Ser
        195                 200                 205

Pro Ile Val Lys Ser Phe Asn Arg Asn Glu Cys
    210                 215

<210> SEQ ID NO 34
<211> LENGTH: 1347
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 34
caggtgcagc tggtggagtc tgggggaggc ttggtacagc ctggggggtc cctgagactc      60
tcctgtgcag cctctggatt cacctttagc aactatgcca tgagctgggt ccgccaggct     120
ccacggaggg ggctggagtg ggtctccact attggtacta ctgatggtga catacactac     180
gcagactccg ttaagggccg gttcaccatc tccagagaca acgccaagaa cacactgtat     240
ctgcaaatga gcagcctgag agccgaggac acggccgtat atttctgtgc gttacggttc     300
ggggagcatt tcgactactg ggccaggga accctggtca ccgtctcaag cgcctccacc     360
aagggcccat cggtcttccc gctagcaccc tcctccaaga gcacctctgg ggcacagcg      420 gccctgggct gcctggtcaa ggactacttc cccgaaccgg tgacggtgtc gtggaactca     480
ggcgccctga ccagcggcgt ccacaccttc ccggctgtcc tacagtcctc cggactctac     540
tccctcagca gcgtagtgac cgtgccctcc agcagcttgg gcacccagac ctacatctgc     600
aacgtgaatc acaagcccag caacaccaag gtggacaaga agttgagcc caaatcttgt      660 gacaaaactc acacatgccc accgtgccca gcacctgaac tcctgggggg accgtcagtc     720
ttcctcttcc ccccaaaacc caaggacacc ctcatgatct cccggacccc tgaggtcaca     780
tgcgtggtgg tggacgtgag ccacgaagac cctgaggtca agttcaactg gtacgtggac     840
ggcgtggagg tgcataatgc caagacaaag ccgcgggagg agcagtacaa cagcacgtac     900
cgtgtggtca gcgtcctcac cgtcctgcac caggactggc tgaatggcaa ggagtacaag     960
tgcaaggtct ccaacaaagc cctcccagcc cccatcgaga aaaccatctc caaagccaaa    1020
gggcagcccc gagaaccaca ggtgtacacc ctgcccccat cccgggatga gctgaccaag    1080
aaccaggtca gcctgacctg cctggtcaaa ggcttctatc ccagcgacat cgccgtggag    1140
tgggagagca atgggcagcc ggagaacaac tacaagacca cgcctcccgt gctggactcc    1200
gacggctcct tcttcctcta cagcaagctc accgtggaca agagcaggtg gcagcagggg    1260
aacgtcttct catgctccgt gatgcatgag gctctgcaca accactacac gcagaagagc    1320
ctctccctgt ctccgggtaa atgataa                                        1347

<210> SEQ ID NO 35
<211> LENGTH: 447
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 35

Gln Val Gln Leu Val Glu Ser Gly Gly Gly Leu Val Gln Pro Gly Gly
1               5                   10                  15

```
Ser Leu Arg Leu Ser Cys Ala Ala Ser Gly Phe Thr Phe Ser Asn Tyr
        20                  25                  30

Ala Met Ser Trp Val Arg Gln Ala Pro Arg Gly Leu Glu Trp Val
            35                  40                  45

Ser Thr Ile Gly Thr Thr Asp Gly Asp Ile His Tyr Ala Asp Ser Val
    50                  55                  60

Lys Gly Arg Phe Thr Ile Ser Arg Asp Asn Ala Lys Asn Thr Leu Tyr
65                  70                  75                  80

Leu Gln Met Ser Ser Leu Arg Ala Glu Asp Thr Ala Val Tyr Phe Cys
                85                  90                  95

Ala Leu Arg Phe Gly Glu His Phe Asp Tyr Trp Gly Gln Gly Thr Leu
            100                 105                 110

Val Thr Val Ser Ser Ala Ser Thr Lys Gly Pro Ser Val Phe Pro Leu
            115                 120                 125

Ala Pro Ser Ser Lys Ser Thr Ser Gly Gly Thr Ala Ala Leu Gly Cys
130                 135                 140

Leu Val Lys Asp Tyr Phe Pro Glu Pro Val Thr Val Ser Trp Asn Ser
145                 150                 155                 160

Gly Ala Leu Thr Ser Gly Val His Thr Phe Pro Ala Val Leu Gln Ser
            165                 170                 175

Ser Gly Leu Tyr Ser Leu Ser Ser Val Val Thr Val Pro Ser Ser Ser
            180                 185                 190

Leu Gly Thr Gln Thr Tyr Ile Cys Asn Val Asn His Lys Pro Ser Asn
            195                 200                 205

Thr Lys Val Asp Lys Lys Val Glu Pro Lys Ser Cys Asp Lys Thr His
210                 215                 220

Thr Cys Pro Pro Cys Pro Ala Pro Glu Leu Leu Gly Gly Pro Ser Val
225                 230                 235                 240

Phe Leu Phe Pro Pro Lys Pro Lys Asp Thr Leu Met Ile Ser Arg Thr
            245                 250                 255

Pro Glu Val Thr Cys Val Val Val Asp Val Ser His Glu Asp Pro Glu
            260                 265                 270

Val Lys Phe Asn Trp Tyr Val Asp Gly Val Glu Val His Asn Ala Lys
            275                 280                 285

Thr Lys Pro Arg Glu Glu Gln Tyr Asn Ser Thr Tyr Arg Val Val Ser
290                 295                 300

Val Leu Thr Val Leu His Gln Asp Trp Leu Asn Gly Lys Glu Tyr Lys
305                 310                 315                 320

Cys Lys Val Ser Asn Lys Ala Leu Pro Ala Pro Ile Glu Lys Thr Ile
            325                 330                 335

Ser Lys Ala Lys Gly Gln Pro Arg Glu Pro Gln Val Tyr Thr Leu Pro
            340                 345                 350

Pro Ser Arg Asp Glu Leu Thr Lys Asn Gln Val Ser Leu Thr Cys Leu
            355                 360                 365

Val Lys Gly Phe Tyr Pro Ser Asp Ile Ala Val Glu Trp Glu Ser Asn
            370                 375                 380

Gly Gln Pro Glu Asn Asn Tyr Lys Thr Thr Pro Pro Val Leu Asp Ser
385                 390                 395                 400

Asp Gly Ser Phe Phe Leu Tyr Ser Lys Leu Thr Val Asp Lys Ser Arg
                405                 410                 415

Trp Gln Gln Gly Asn Val Phe Ser Cys Ser Val Met His Glu Ala Leu
            420                 425                 430
```

His Asn His Tyr Thr Gln Lys Ser Leu Ser Leu Ser Pro Gly Lys
            435                 440                 445

<210> SEQ ID NO 36
<211> LENGTH: 1485
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 36
caggtgcagc tggtggagtc tgggggaggc ttggtacagc ctggggggtc cctgagactc      60
tcctgtgcag cctctggatt cacctttagc aactatgcca tgagctgggt ccgccaggct     120
ccacggaggg gctggagtg gtctccact attggtacta ctgatggtga catacactac       180
gcagactccg ttaagggccg gttcaccatc tccagagaca acgccaagaa cacactgtat     240
ctgcaaatga gcagcctgag agccgaggac acggccgtat atttctgtgc gttacggttc     300
ggggagcatt tcgactactg gggccaggga accctggtca ccgtctcaag cgcctccacc     360
aagggcccat cggtcttccc cctggcgccc tgctccagga gcacctctgg gggcacagcg     420
gccctgggct gcctggtcaa ggactacttc cccgaaccgg tgacggtgtc gtggaactca     480
ggcgccctga ccagcggcgt ccataccttc ccggctgtcc tacagtcctc aggactctac     540
tccctcagca gcgtggtcac agtgccctcc agcagcttgg gcacccagac ctacacctgc     600
aacgtgaatc acaagcccag caacaccaag gtggacaaga gagttgagct caaaaccca     660 cttggtgaca caactcacac atgcccacgg tgcccagagc ccaaatcttg tgacacacct     720
cccccgtacc cacggtgccc agagcccaaa tcttgtgaca cacctccccc atgcccacgg     780
tgcccagagc ccaaatcttg tgacacacct cccccatgcc acggtgccc agcacctgaa      840 ctcctgggag gaccgtcagt cttcctcttc ccccaaaac ccaaggatac ccttatgatt      900
tcccggaccc ctgaggtcac gtgcgtggtg gtggacgtga gccacgaaga ccccgaggtc     960
cagttcaagt ggtacgtgga cggcgtggag gtgcataatg ccaagacaaa gccgcgggag    1020
gagcagttca acagcacgtt ccgtgtggtc agcgtcctca ccgtcctgca ccaggactgg    1080
ctgaacggca aggagtacaa gtgcaaggtc tccaacaaag ccctcccagc ccccatcgag    1140
aaaaccatct ccaaaaccaa aggacagccc cgagaaccac aggtgtacac cctgccccca    1200
tcccgggagg agatgaccaa gaaccaggtc agcctgacct gcctggtcaa aggcttctac    1260
cccagcgaca tcgccgtgga gtgggagagc agcgggcagc cggagaacaa ctacaacacc    1320
acgcctccca tgctggactc cgacggctcc ttcttcctct acagcaagct caccgtggac    1380
aagagcaggt ggcagcaggg gaacatcttc tcatgctccg tgatgcatga ggctctgcac    1440
aaccgcttca cgcagaagag cctctccctg tctccgggta aatag                    1485

<210> SEQ ID NO 37
<211> LENGTH: 494
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 37

Gln Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Asn Tyr

-continued

```
                20                  25                  30
Ala Met Ser Trp Val Arg Gln Ala Pro Arg Gly Leu Glu Trp Val
            35                  40                  45
Ser Thr Ile Gly Thr Thr Asp Gly Asp Ile His Tyr Ala Asp Ser Val
50                  55                  60
Lys Gly Arg Phe Thr Ile Ser Arg Asp Asn Ala Lys Asn Thr Leu Tyr
65                  70                  75                  80
Leu Gln Met Ser Ser Leu Arg Ala Glu Asp Thr Ala Val Tyr Phe Cys
                85                  90                  95
Ala Leu Arg Phe Gly Glu His Phe Asp Tyr Trp Gly Gln Gly Thr Leu
            100                 105                 110
Val Thr Val Ser Ser Ala Ser Thr Lys Gly Pro Ser Val Phe Pro Leu
        115                 120                 125
Ala Pro Cys Ser Arg Ser Thr Ser Gly Gly Thr Ala Ala Leu Gly Cys
    130                 135                 140
Leu Val Lys Asp Tyr Phe Pro Glu Pro Val Thr Val Ser Trp Asn Ser
145                 150                 155                 160
Gly Ala Leu Thr Ser Gly Val His Thr Phe Pro Ala Val Leu Gln Ser
                165                 170                 175
Ser Gly Leu Tyr Ser Leu Ser Ser Val Val Thr Val Pro Ser Ser Ser
            180                 185                 190
Leu Gly Thr Gln Thr Tyr Thr Cys Asn Val Asn His Lys Pro Ser Asn
        195                 200                 205
Thr Lys Val Asp Lys Arg Val Glu Leu Lys Thr Pro Leu Gly Asp Thr
    210                 215                 220
Thr His Thr Cys Pro Arg Cys Pro Glu Pro Lys Ser Cys Asp Thr Pro
225                 230                 235                 240
Pro Pro Tyr Pro Arg Cys Pro Glu Pro Lys Ser Cys Asp Thr Pro Pro
                245                 250                 255
Pro Cys Pro Arg Cys Pro Glu Pro Lys Ser Cys Asp Thr Pro Pro Pro
            260                 265                 270
Cys Pro Arg Cys Pro Ala Pro Glu Leu Leu Gly Gly Pro Ser Val Phe
        275                 280                 285
Leu Phe Pro Pro Lys Pro Lys Asp Thr Leu Met Ile Ser Arg Thr Pro
    290                 295                 300
Glu Val Thr Cys Val Val Val Asp Val Ser His Glu Asp Pro Glu Val
305                 310                 315                 320
Gln Phe Lys Trp Tyr Val Asp Gly Val Glu Val His Asn Ala Lys Thr
                325                 330                 335
Lys Pro Arg Glu Glu Gln Phe Asn Ser Thr Phe Arg Val Val Ser Val
            340                 345                 350
Leu Thr Val Leu His Gln Asp Trp Leu Asn Gly Lys Glu Tyr Lys Cys
        355                 360                 365
Lys Val Ser Asn Lys Ala Leu Pro Ala Pro Ile Glu Lys Thr Ile Ser
    370                 375                 380
Lys Thr Lys Gly Gln Pro Arg Glu Pro Gln Val Tyr Thr Leu Pro Pro
385                 390                 395                 400
Ser Arg Glu Glu Met Thr Lys Asn Gln Val Ser Leu Thr Cys Leu Val
                405                 410                 415
Lys Gly Phe Tyr Pro Ser Asp Ile Ala Val Glu Trp Glu Ser Ser Gly
            420                 425                 430
Gln Pro Glu Asn Asn Tyr Asn Thr Thr Pro Pro Met Leu Asp Ser Asp
        435                 440                 445
```

Gly Ser Phe Phe Leu Tyr Ser Lys Leu Thr Val Asp Lys Ser Arg Trp
            450                 455                 460

Gln Gln Gly Asn Ile Phe Ser Cys Ser Val Met His Glu Ala Leu His
465                 470                 475                 480

Asn Arg Phe Thr Gln Lys Ser Leu Ser Leu Ser Pro Gly Lys
                485                 490

<210> SEQ ID NO 38
<211> LENGTH: 1344
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 38

| | | | | | |
|---|---|---|---|---|---|
| caggtgcagc | tggtggagtc | tgggggaggc | ttggtacagc | ctggggggtc | cctgagactc | 60 |
| tcctgtgcag | cctctggatt | cacctttagc | aactatgcca | tgagctgggt | ccgccaggct | 120 |
| ccacggaggg | ggctggagtg | ggtctccact | attggtacta | ctgatggtga | catacactac | 180 |
| gcagactccg | ttaagggccg | gttcaccatc | tccagagaca | acgccaagaa | cacactgtat | 240 |
| ctgcaaatga | gcagcctgag | agccgaggac | acggccgtat | atttctgtgc | gttacggttc | 300 |
| ggggagcatt | tcgactactg | gggccaggga | accctggtca | ccgtctcaag | cgcctccacc | 360 |
| aagggcccat | cggtcttccc | gctagcccct | gtgtgtggag | atacaactgg | ctcctcggtg | 420 |
| actctaggat | gcctggtcaa | gggttatttc | cctgagccag | tgaccttgac | ctggaactct | 480 |
| ggatccctgt | ccagtggtgt | ccacaccttc | ccagctgtcc | tgcagtctga | cctctacacc | 540 |
| ctcagcagct | cagtgactgt | aacctcgagc | acctggccca | gccagtccat | cacctgcaat | 600 |
| gtggcccacc | cggcaagcag | caccaaggtg | gacaagaaaa | ttgagcccag | agggcccaca | 660 |
| atcaagccct | gtcctccatg | caaatgccca | gcacctaacc | tcttgggtgg | accatccgtc | 720 |
| ttcatcttcc | ctccaaagat | caaggatgta | ctcatgatct | ccctgagccc | catagtcaca | 780 |
| tgtgtggtgg | tggatgtgag | cgaggatgac | ccagatgtcc | agatcagctg | gtttgtgaac | 840 |
| aacgtggaag | tacacacagc | tcagacacaa | acccatagag | aggattacaa | cagtactctc | 900 |
| cgggtggtca | gtgccctccc | catccagcac | caggactgga | tgagtggcaa | ggagttcaaa | 960 |
| tgcaaggtca | caacaaaga | cctcccagcg | cccatcgaga | gaaccatctc | aaaacccaaa | 1020 |
| gggtcagtaa | gagctccaca | ggtatatgtc | ttgcctccac | cagaagaaga | gatgactaag | 1080 |
| aaacaggtca | ctctgacctg | catggtcaca | gacttcatgc | ctgaagacat | ttacgtggag | 1140 |
| tggaccaaca | acgggaaaac | agagctaaac | tacaagaaca | ctgaaccagt | cctggactct | 1200 |
| gatggttctt | acttcatgta | cagcaagctg | agagtggaaa | agaagaactg | ggtggaaaga | 1260 |
| aatagctact | cctgttcagt | ggtccacgag | ggtctgcaca | atcaccacac | gactaagagc | 1320 |
| ttctcccgga | ctccgggtaa | atga | | | | 1344 |

<210> SEQ ID NO 39
<211> LENGTH: 447
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 39

Gln Val Gln Leu Val Glu Ser Gly Gly Gly Leu Val Gln Pro Gly Gly

-continued

```
1               5                   10                  15
Ser Leu Arg Leu Ser Cys Ala Ala Ser Gly Phe Thr Phe Ser Asn Tyr
            20                  25                  30

Ala Met Ser Trp Val Arg Gln Ala Pro Arg Arg Gly Leu Glu Trp Val
            35                  40                  45

Ser Thr Ile Gly Thr Thr Asp Gly Asp Ile His Tyr Ala Asp Ser Val
            50                  55                  60

Lys Gly Arg Phe Thr Ile Ser Arg Asp Asn Ala Lys Asn Thr Leu Tyr
65                  70                  75                  80

Leu Gln Met Ser Ser Leu Arg Ala Glu Asp Thr Ala Val Tyr Phe Cys
            85                  90                  95

Ala Leu Arg Phe Gly Glu His Phe Asp Tyr Trp Gly Gln Gly Thr Leu
            100                 105                 110

Val Thr Val Ser Ser Ala Ser Thr Lys Gly Pro Ser Val Phe Pro Leu
            115                 120                 125

Ala Pro Val Cys Gly Asp Thr Thr Gly Ser Ser Val Thr Leu Gly Cys
            130                 135                 140

Leu Val Lys Gly Tyr Phe Pro Glu Pro Val Thr Leu Thr Trp Asn Ser
145                 150                 155                 160

Gly Ser Leu Ser Ser Gly Val His Thr Phe Pro Ala Val Leu Gln Ser
            165                 170                 175

Asp Leu Tyr Thr Leu Ser Ser Ser Val Thr Val Thr Ser Ser Thr Trp
            180                 185                 190

Pro Ser Gln Ser Ile Thr Cys Asn Val Ala His Pro Ala Ser Ser Thr
            195                 200                 205

Lys Val Asp Lys Lys Ile Glu Pro Arg Gly Pro Thr Ile Lys Pro Cys
210                 215                 220

Pro Pro Cys Lys Cys Pro Ala Pro Asn Leu Leu Gly Gly Pro Ser Val
225                 230                 235                 240

Phe Ile Phe Pro Pro Lys Ile Lys Asp Val Leu Met Ile Ser Leu Ser
            245                 250                 255

Pro Ile Val Thr Cys Val Val Val Asp Val Ser Glu Asp Asp Pro Asp
            260                 265                 270

Val Gln Ile Ser Trp Phe Val Asn Asn Val Glu Val His Thr Ala Gln
            275                 280                 285

Thr Gln Thr His Arg Glu Asp Tyr Asn Ser Thr Leu Arg Val Val Ser
            290                 295                 300

Ala Leu Pro Ile Gln His Gln Asp Trp Met Ser Gly Lys Glu Phe Lys
305                 310                 315                 320

Cys Lys Val Asn Asn Lys Asp Leu Pro Ala Pro Ile Glu Arg Thr Ile
            325                 330                 335

Ser Lys Pro Lys Gly Ser Val Arg Ala Pro Gln Val Tyr Val Leu Pro
            340                 345                 350

Pro Pro Glu Glu Glu Met Thr Lys Lys Gln Val Thr Leu Thr Cys Met
            355                 360                 365

Val Thr Asp Phe Met Pro Glu Asp Ile Tyr Val Glu Trp Thr Asn Asn
            370                 375                 380

Gly Lys Thr Glu Leu Asn Tyr Lys Asn Thr Glu Pro Val Leu Asp Ser
385                 390                 395                 400

Asp Gly Ser Tyr Phe Met Tyr Ser Lys Leu Arg Val Glu Lys Lys Asn
            405                 410                 415

Trp Val Glu Arg Asn Ser Tyr Ser Cys Ser Val Val His Glu Gly Leu
            420                 425                 430
```

His Asn His His Thr Thr Lys Ser Phe Ser Arg Thr Pro Gly Lys
          435                 440                 445

<210> SEQ ID NO 40
<211> LENGTH: 1343
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 40

```
caggtgcagc tggtggagtc tgggggaggc ttggtacagc ctgggggtc cctgagactc      60
tcctgtgcag cctctggatt cacctttagc aactatgcca tgagctgggt ccgccaggct    120
ccacggaggg gctggagtg gtctccact attggtacta ctgatggtga catacactac      180
gcagactccg ttaagggccg gttcaccatc tccagagaca acgccaagaa cacactgtat    240
ctgcaaatga gcagcctgag agccgaggac acggccgtat atttctgtgc gttacggttc    300
ggggagcatt tcgactactg gggccaggga accctggtca ccgtctcaag cgccaaaaca    360
acagccccat cggtctatcc actagcccct gtgtgtggag atacaactgg ctcctcggtg    420
actctaggat gcctggtcaa gggttatttc cctgagccag tgaccttgac ctggaactct    480
ggatccctgt ccagtggtgt ccacaccttc ccagctgtcc tgcagtctga cctctacacc    540
ctcagcagct cagtgactgt aacctcgagc acctggccca gccagtccat cacctgcaat    600
gtggcccacc cggcaagcag caccaaggtg gacaagaaaa ttgagcccag agggcccaca    660
atcaagccct gtcctccatg caaatgccca gcacctaacc tcttgggtgg accatccgtc    720
ttcatcttcc ctccaaagat caaggatgta ctcatgatct ccctgagccc catagtcaca    780
tgtgtggtgg tggatgtgag cgaggatgac ccagatgtcc agatcagctg gtttgtgaac    840
aacgtggaag tacacacagc tcagacacaa acccatagag aggattacaa cagtactctc    900
cgggtggtca gtgccctccc catccagcac caggactgga tgagtggcaa ggagttcaaa    960
tgcaaggtca acaacaaaga cctcccagcg cccatcgaga gaaccatctc aaaacccaaa   1020
gggtcagtaa gagctccaca ggtatatgtc ttgcctccac cagaagaaga gatgactaag   1080
aaacaggtca ctctgacctg catggtcaca gacttcatgc ctgaagacat ttacgtggag   1140
tggaccaaca cgggaaaac agagctaaac tacaagaaca ctgaaccagt cctggactct   1200
gatggttctt acttcatgta cagcaagctg agagtggaaa agaagaactg ggtggaaaga   1260
aatagctact cctgttcagt ggtccacgag ggtctgcaca tcacacacg actaagagct   1320
tctcccggac tccgggtaaa tag                                            1343
```

<210> SEQ ID NO 41
<211> LENGTH: 447
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 41

Gln Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Asn Tyr
            20                  25                  30

Ala Met Ser Trp Val Arg Gln Ala Pro Arg Arg Gly Leu Glu Trp Val

```
            35                  40                  45
Ser Thr Ile Gly Thr Thr Asp Gly Asp Ile His Tyr Ala Asp Ser Val
 50                  55                  60

Lys Gly Arg Phe Thr Ile Ser Arg Asp Asn Ala Lys Asn Thr Leu Tyr
 65                  70                  75                  80

Leu Gln Met Ser Ser Leu Arg Ala Glu Asp Thr Ala Val Tyr Phe Cys
                 85                  90                  95

Ala Leu Arg Phe Gly Glu His Phe Asp Tyr Trp Gly Gln Gly Thr Leu
            100                 105                 110

Val Thr Val Ser Ser Ala Lys Thr Thr Ala Pro Ser Val Tyr Pro Leu
        115                 120                 125

Ala Pro Val Cys Gly Asp Thr Thr Gly Ser Ser Val Thr Leu Gly Cys
    130                 135                 140

Leu Val Lys Gly Tyr Phe Pro Glu Pro Val Thr Leu Thr Trp Asn Ser
145                 150                 155                 160

Gly Ser Leu Ser Ser Gly Val His Thr Phe Pro Ala Val Leu Gln Ser
                165                 170                 175

Asp Leu Tyr Thr Leu Ser Ser Ser Val Thr Val Thr Ser Ser Thr Trp
            180                 185                 190

Pro Ser Gln Ser Ile Thr Cys Asn Val Ala His Pro Ala Ser Ser Thr
        195                 200                 205

Lys Val Asp Lys Lys Ile Glu Pro Arg Gly Pro Thr Ile Lys Pro Cys
    210                 215                 220

Pro Pro Cys Lys Cys Pro Ala Pro Asn Leu Leu Gly Gly Pro Ser Val
225                 230                 235                 240

Phe Ile Phe Pro Pro Lys Ile Lys Asp Val Leu Met Ile Ser Leu Ser
                245                 250                 255

Pro Ile Val Thr Cys Val Val Asp Val Ser Glu Asp Asp Pro Asp
            260                 265                 270

Val Gln Ile Ser Trp Phe Val Asn Asn Val Glu Val His Thr Ala Gln
        275                 280                 285

Thr Gln Thr His Arg Glu Asp Tyr Asn Ser Thr Leu Arg Val Val Ser
    290                 295                 300

Ala Leu Pro Ile Gln His Gln Asp Trp Met Ser Gly Lys Glu Phe Lys
305                 310                 315                 320

Cys Lys Val Asn Asn Lys Asp Leu Pro Ala Pro Ile Glu Arg Thr Ile
                325                 330                 335

Ser Lys Pro Lys Gly Ser Val Arg Ala Pro Gln Val Tyr Val Leu Pro
            340                 345                 350

Pro Pro Glu Glu Glu Met Thr Lys Lys Gln Val Thr Leu Thr Cys Met
        355                 360                 365

Val Thr Asp Phe Met Pro Glu Asp Ile Tyr Val Glu Trp Thr Asn Asn
    370                 375                 380

Gly Lys Thr Glu Leu Asn Tyr Lys Asn Thr Glu Pro Val Leu Asp Ser
385                 390                 395                 400

Asp Gly Ser Tyr Phe Met Tyr Ser Lys Leu Arg Val Glu Lys Lys Asn
                405                 410                 415

Trp Val Glu Arg Asn Ser Tyr Ser Cys Ser Val Val His Glu Gly Leu
            420                 425                 430

His Asn His His Thr Thr Lys Ser Phe Ser Arg Thr Pro Gly Lys
        435                 440                 445

<210> SEQ ID NO 42
```

<211> LENGTH: 1344
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 42

```
caggtgcagc tggtggagtc tgggggaggc ttggtacagc ctgggggtc cctgagactc      60
tcctgtgcag cctctggatt cacctttagc aactatgcca tgagctgggt ccgccaggct     120
ccacggaggg ggctggagtg ggtctccact attggtacta ctgatggtga catacactac     180
gcagactccg ttaagggccg gttcaccatc tccagagaca cgccaagaa cacactgtat     240
ctgcaaatga gcagcctgag agccgaggac acggccgtat atttctgtgc gttacggttc     300
ggggagcatt tcgactactg gggccaggga accctggtca ccgtctcaag cgcctccacc     360
aagggcccat cggtcttccc cctggcaccc tcctccaaga gcacctctgg gggcacagcg     420
gccctgggct gcctggtcaa ggactacttc cccgaaccgg tgacggtgtc gtggaactca     480
ggcgccctga ccagcggcgt ccataccttc ccggctgtcc tacagtcctc aggactctac     540
tccctcagca gcgtggtcac agtgccctcc agcagcttgg gcacccagac ctacatctgc     600
aacgtgaatc acaagcccag caacaccaag gtggacaaga agttgagcc caaatcttgt     660
gacaaaactc acacatgccc accgtgccca gcacctaacc tcttgggtgg accatccgtc     720
ttcatcttcc ctccaaagat caaggatgta ctcatgatct ccctgagccc catagtcaca     780
tgtgtggtgg tggatgtgag cgaggatgac ccagatgtcc agatcagctg gtttgtgaac     840
aacgtggaag tacacacagc tcagacacaa acccatagag aggattacaa cagtactctc     900
cgggtggtca gtgccctccc catccagcac caggactgga tgagtggcaa ggagttcaaa     960
tgcaaggtca acaacaaaga cctcccagcg cccatcgaga gaaccatctc aaaacccaaa    1020
gggtcagtaa gagctccaca ggtatatgtc ttgcctccac cagaagaaga tgactaag     1080
aaacaggtca ctctgacctg catggtcaca gacttcatgc ctgaagacat ttacgtggag    1140
tggaccaaca acgggaaaac agagctaaac tacaagaaca ctgaaccagt cctggactct    1200
gatggttctt acttcatgta cagcaagctg agagtggaaa agaagaactg gtggaagaga    1260
aatagctact cctgttcagt ggtccacgag ggtctgcaca atcaccacac gactaagagc    1320
ttctcccgga ctccgggtaa atag                                           1344
```

<210> SEQ ID NO 43
<211> LENGTH: 447
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 43

```
Gln Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Asn Tyr
            20                  25                  30

Ala Met Ser Trp Val Arg Gln Ala Pro Arg Arg Gly Leu Glu Trp Val
        35                  40                  45

Ser Thr Ile Gly Thr Thr Asp Gly Asp Ile His Tyr Ala Asp Ser Val
    50                  55                  60

Lys Gly Arg Phe Thr Ile Ser Arg Asp Asn Ala Lys Asn Thr Leu Tyr
```

```
                65                  70                  75                  80
        Leu Gln Met Ser Ser Leu Arg Ala Glu Asp Thr Ala Val Tyr Phe Cys
                        85                  90                  95

Ala Leu Arg Phe Gly Glu His Phe Asp Tyr Trp Gly Gln Gly Thr Leu
                    100                 105                 110

Val Thr Val Ser Ser Ala Ser Thr Lys Gly Pro Ser Val Phe Pro Leu
                    115                 120                 125

Ala Pro Ser Ser Lys Ser Thr Ser Gly Gly Thr Ala Ala Leu Gly Cys
        130                 135                 140

Leu Val Lys Asp Tyr Phe Pro Glu Pro Val Thr Val Ser Trp Asn Ser
        145                 150                 155                 160

Gly Ala Leu Thr Ser Gly Val His Thr Phe Pro Ala Val Leu Gln Ser
                        165                 170                 175

Ser Gly Leu Tyr Ser Leu Ser Ser Val Val Thr Val Pro Ser Ser Ser
                    180                 185                 190

Leu Gly Thr Gln Thr Tyr Ile Cys Asn Val Asn His Lys Pro Ser Asn
                    195                 200                 205

Thr Lys Val Asp Lys Lys Val Glu Pro Lys Ser Cys Asp Lys Thr His
                210                 215                 220

Thr Cys Pro Pro Cys Pro Ala Pro Asn Leu Leu Gly Gly Pro Ser Val
        225                 230                 235                 240

Phe Ile Phe Pro Pro Lys Ile Lys Asp Val Leu Met Ile Ser Leu Ser
                        245                 250                 255

Pro Ile Val Thr Cys Val Val Val Asp Val Ser Glu Asp Asp Pro Asp
                    260                 265                 270

Val Gln Ile Ser Trp Phe Val Asn Asn Val Glu Val His Thr Ala Gln
                    275                 280                 285

Thr Gln Thr His Arg Glu Asp Tyr Asn Ser Thr Leu Arg Val Val Ser
                290                 295                 300

Ala Leu Pro Ile Gln His Gln Asp Trp Met Ser Gly Lys Glu Phe Lys
        305                 310                 315                 320

Cys Lys Val Asn Asn Lys Asp Leu Pro Ala Pro Ile Glu Arg Thr Ile
                        325                 330                 335

Ser Lys Pro Lys Gly Ser Val Arg Ala Pro Gln Val Tyr Val Leu Pro
                    340                 345                 350

Pro Pro Glu Glu Glu Met Thr Lys Lys Gln Val Thr Leu Thr Cys Met
                    355                 360                 365

Val Thr Asp Phe Met Pro Glu Asp Ile Tyr Val Glu Trp Thr Asn Asn
        370                 375                 380

Gly Lys Thr Glu Leu Asn Tyr Lys Asn Thr Glu Pro Val Leu Asp Ser
        385                 390                 395                 400

Asp Gly Ser Tyr Phe Met Tyr Ser Lys Leu Arg Val Glu Lys Lys Asn
                        405                 410                 415

Trp Val Glu Arg Asn Ser Tyr Ser Cys Ser Val Val His Glu Gly Leu
                    420                 425                 430

His Asn His His Thr Thr Lys Ser Phe Ser Arg Thr Pro Gly Lys
                    435                 440                 445

<210> SEQ ID NO 44
<211> LENGTH: 1485
<212> TYPE: DNA
<213> ORGANISM: Artificial Sequence
<220> FEATURE:
<223> OTHER INFORMATION: Description of Artificial Sequence: Synthetic
      polynucleotide
```

<400> SEQUENCE: 44

```
caggtgcagc tggtggagtc tgggggaggc ttggtacagc ctgggggtc cctgagactc       60
tcctgtgcag cctctggatt caccttagc aactatgcca tgagctgggt ccgccaggct      120
ccacggaggg ggctggagtg ggtctccact attggtacta ctgatggtga catacactac     180
gcagactccg ttaagggccg gttcaccatc tccagagaca acgccaagaa cacactgtat     240
ctgcaaatga gcagcctgag agccgaggac acggccgtat atttctgtgc gttacggttc     300
ggggagcatt tcgactactg gggccaggga accctggtca ccgtctcaag cgcctccacc     360
aagggcccat cggtcttccc cctggcgccc tgctccagga gcacctctgg ggcacagcg      420
gccctgggct gcctggtcaa ggactacttc cccgaaccgg tgacggtgtc gtggaactca     480
ggcgccctga ccagcggcgt ccatacctc ccggctgtcc tacagtcctc aggactctac      540
tccctcagca gcgtggtcac agtgccctcc agcagcttgg gcacccagac ctacacctgc     600
aacgtgaatc acaagcccag caacaccaag gtggacaaga gagttgagct caaaacccca     660
cttggtgaca caactcacac atgcccacgg tgcccagagc ccaaatcttg tgacacacct     720
cccccgtacc cacggtgccc agagcccaaa tcttgtgaca cacctccccc atgcccacgg     780
tgcccagagc ccaaatcttg tgacacacct cccccatgcc cacggtgccc agcacctaac     840
ctcttgggtg gaccatccgt cttcatcttc cctccaaaga tcaaggatgt actcatgatc     900
tccctgagcc ccatagtcac atgtgtggtg gtggatgtga gcgaggatga cccagatgtc     960
cagatcagct ggtttgtgaa caacgtgaa gtacacacag ctcagacaca aacccataga    1020
gaggattaca acagtactct ccgggtggtc agtgccctcc ccatccagca ccaggactgg    1080
atgagtggca aggagttcaa atgcaaggtc aacaacaaag acctcccagc gcccatcgag    1140
agaaccatct caaacccaa agggtcagta agagctccac aggtatatgt cttgcctcca    1200
ccagaagaag atgactaa gaaacaggtc actctgacct gcatggtcac agacttcatg    1260
cctgaagaca tttacgtgga gtggaccaac aacgggaaaa cagagctaaa ctacaagaac    1320
actgaaccag tcctggactc tgatggttct tacttcatgt acagcaagct gagagtggaa    1380
aagaagaact gggtggaaag aaatagctac tcctgttcag tggtccacga gggtctgcac    1440
aatcaccaca cgactaagag cttctcccgg actccgggta aatag                    1485
```

<210> SEQ ID NO 45
<211> LENGTH: 494
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 45

```
Gln Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Asn Tyr
            20                  25                  30

Ala Met Ser Trp Val Arg Gln Ala Pro Arg Arg Gly Leu Glu Trp Val
        35                  40                  45

Ser Thr Ile Gly Thr Thr Asp Gly Asp Ile His Tyr Ala Asp Ser Val
    50                  55                  60

Lys Gly Arg Phe Thr Ile Ser Arg Asp Asn Ala Lys Asn Thr Leu Tyr
65                  70                  75                  80
```

```
Leu Gln Met Ser Ser Leu Arg Ala Glu Asp Thr Ala Val Tyr Phe Cys
                85                  90                  95
Ala Leu Arg Phe Gly Glu His Phe Asp Tyr Trp Gly Gln Gly Thr Leu
            100                 105                 110
Val Thr Val Ser Ser Ala Ser Thr Lys Gly Pro Ser Val Phe Pro Leu
        115                 120                 125
Ala Pro Cys Ser Arg Ser Thr Ser Gly Gly Thr Ala Ala Leu Gly Cys
    130                 135                 140
Leu Val Lys Asp Tyr Phe Pro Glu Pro Val Thr Val Ser Trp Asn Ser
145                 150                 155                 160
Gly Ala Leu Thr Ser Gly Val His Thr Phe Pro Ala Val Leu Gln Ser
                165                 170                 175
Ser Gly Leu Tyr Ser Leu Ser Ser Val Val Thr Val Pro Ser Ser Ser
            180                 185                 190
Leu Gly Thr Gln Thr Tyr Thr Cys Asn Val Asn His Lys Pro Ser Asn
        195                 200                 205
Thr Lys Val Asp Lys Arg Val Glu Leu Lys Thr Pro Leu Gly Asp Thr
    210                 215                 220
Thr His Thr Cys Pro Arg Cys Pro Glu Pro Lys Ser Cys Asp Thr Pro
225                 230                 235                 240
Pro Pro Tyr Pro Arg Cys Pro Glu Pro Lys Ser Cys Asp Thr Pro Pro
                245                 250                 255
Pro Cys Pro Arg Cys Pro Glu Pro Lys Ser Cys Asp Thr Pro Pro Pro
            260                 265                 270
Cys Pro Arg Cys Pro Ala Pro Asn Leu Leu Gly Gly Pro Ser Val Phe
        275                 280                 285
Ile Phe Pro Pro Lys Ile Lys Asp Val Leu Met Ile Ser Leu Ser Pro
    290                 295                 300
Ile Val Thr Cys Val Val Val Asp Val Ser Glu Asp Asp Pro Asp Val
305                 310                 315                 320
Gln Ile Ser Trp Phe Val Asn Asn Val Glu Val His Thr Ala Gln Thr
                325                 330                 335
Gln Thr His Arg Glu Asp Tyr Asn Ser Thr Leu Arg Val Val Ser Ala
            340                 345                 350
Leu Pro Ile Gln His Gln Asp Trp Met Ser Gly Lys Glu Phe Lys Cys
        355                 360                 365
Lys Val Asn Asn Lys Asp Leu Pro Ala Pro Ile Glu Arg Thr Ile Ser
    370                 375                 380
Lys Pro Lys Gly Ser Val Arg Ala Pro Gln Val Tyr Val Leu Pro Pro
385                 390                 395                 400
Pro Glu Glu Glu Met Thr Lys Lys Gln Val Thr Leu Thr Cys Met Val
                405                 410                 415
Thr Asp Phe Met Pro Glu Asp Ile Tyr Val Glu Trp Thr Asn Asn Gly
            420                 425                 430
Lys Thr Glu Leu Asn Tyr Lys Asn Thr Glu Pro Val Leu Asp Ser Asp
        435                 440                 445
Gly Ser Tyr Phe Met Tyr Ser Lys Leu Arg Val Glu Lys Lys Asn Trp
    450                 455                 460
Val Glu Arg Asn Ser Tyr Ser Cys Ser Val Val His Glu Gly Leu His
465                 470                 475                 480
Asn His His Thr Thr Lys Ser Phe Ser Arg Thr Pro Gly Lys
                485                 490
```